United States Patent
Barbas, III

(10) Patent No.: US 8,518,927 B2
(45) Date of Patent: Aug. 27, 2013

(54) CHEMICALLY PROGRAMMED VACCINATION

(75) Inventor: Carlos F. Barbas, III, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/148,658

(22) PCT Filed: Feb. 10, 2010

(86) PCT No.: PCT/US2010/023770
§ 371 (c)(1),
(2), (4) Date: Aug. 18, 2011

(87) PCT Pub. No.: WO2010/093706
PCT Pub. Date: Aug. 19, 2010

(65) Prior Publication Data
US 2011/0311516 A1    Dec. 22, 2011

Related U.S. Application Data

(60) Provisional application No. 61/151,454, filed on Feb. 10, 2009.

(51) Int. Cl.
*A01N 43/00* (2006.01)
*A61K 31/33* (2006.01)

(52) U.S. Cl.
USPC ........................................................ 514/183

(58) Field of Classification Search
None
See application file for complete search history.

(56) References Cited

FOREIGN PATENT DOCUMENTS

| WO | WO 03/034995 A2 | 5/2003 |
|---|---|---|
| WO | WO 2004/091542 A2 | 10/2004 |
| WO | WO 2006/094269 A2 | 9/2006 |
| WO | WO 2008/006102 A2 | 1/2008 |
| WO | WO 2009/139863 A2 | 11/2009 |
| WO | WO 2009/148554 A1 | 12/2009 |

OTHER PUBLICATIONS

Doppalapudi et al., "Chemically Programmed Antibodies: Endothelin Receptor Targeting CovX-Bodies™," *Bioorganic & Medicinal Chemistty Letters* (2007), 17(2):501-506, Elsevier Ltd.
Guo et al., "Breaking the One Antibody—One Target Axiom," *PNAS* (2006), 103(29):11009-11014, Suppl. (6 pages), The National Academy of Sciences of the USA.
Li et al., "Chemical Adaptor Immunotherapy: Design, Synthesis, and Evaluation of Novel Integrin-Targeting Devices," *J. Med. Chem.* (2004), 47(23):5630-5640, Suppl. (16 pages), American Chemical Society.
Popkov et al., "Small Molecule Drug Activity in Melanoma Models May Be Dramatically Enhanced with an Antibody Effector," *Int. J. Cancer* (2006), 119(5):1194-1207, Wiley-Liss, Inc.
Rader et al., "A Humanized Aldolase Antibody for Selective Chemotherapy and Adaptor Immunotherapy," *J. Mol. Biol.* (2003) 332(4):889-899, Elsevier Ltd.

*Primary Examiner* — Craig Ricci
*Assistant Examiner* — Jared D Barsky
(74) *Attorney, Agent, or Firm* — DLA Piper LLP (US)

(57) ABSTRACT

Provided herein is a method for chemically programmed vaccination. Methods include inducing a covalent-binding polyclonal antibody response in a subject and programming the polyclonal response with a targeting compound.

2 Claims, 18 Drawing Sheets

CT26/BALBC

HIV-1 viral envelope targeting agent based on BMS-378806

CHEMICALLY PROGRAMMED VACCINATION

CROSS REFERENCE TO RELATED APPLICATIONS

This application is a 35 USC §371 National Stage application of International Application No. PCT/US2010/023770 filed Feb. 10, 2010, now pending; which claims the benefit under 35 USC §119(e) to U.S. Application Ser. No. 61/151,454 filed Feb. 10, 2009, now expired. The disclosure of each of the prior applications is considered part of and is incorporated by reference in the disclosure of this application.

GRANT INFORMATION

This invention was made with government support under Contract No. CA104045 awarded by the National Institutes of Health. The government has certain rights in this invention.

BACKGROUND OF THE DISCLOSURE

1. Field of the Disclosure

The present disclosure relates generally to immune responses and more specifically to inducing a covalent polyclonal antibody response in a subject, wherein the polyclonal response can be programmed to bind a diverse range of target antigens following administration or addition of a targeting compound designed to covalently engage the induced polyclonal response.

2. Background Information

Despite certain limitations, the time-honored tradition of vaccination has been extraordinarily successful. Typically, a disease relevant immune response is achieved following one or more immunizations and the level of response wherein a prophylactic or therapeutic effect is observed takes days or weeks to build. Thus, vaccination is anticipatory by nature and the kinetics of the immune response limits the efficacy of vaccine-based strategies against aggressive pathogens or rapidly acting toxins wherein one would desire the ability to instantly create an immune state. Ideally, immunity could be specifically and rapidly directed against a non-self antigen like a virus or bacterium or a self-antigen related to cancer or a viral entry receptor like CCR5. The later class of antigens involves breaking tolerance and presents inherent challenges that have only recently begun to be addressed. The most commonly employed vaccination strategies use whole proteins, viruses, or other complex immunogens and induce antibodies reactive against both non-functional and functional epitopes; the ideal approach would direct immunity only against functional or neutralizing epitopes, for example the conserved neutralizing epitopes on HIV-1. Ideally, one would like to circumvent the age-related declines in immune function. Thus, there remains a need in the art for new and improved vaccination methods.

SUMMARY OF THE DISCLOSURE

The present disclosure is based on the seminal discovery that pre-immunization of a subject with KLH coupled with a designed reactive hapten followed by administration of an targeting agent designed to react with induced polyclonal antibodies, results in a programmed covalent polyclonal antibody response with the specificity of the targeting agent.

In one embodiment, the disclosure provides a method of generating covalent polyclonal antibodies including preimmunizing a subject with an immunizing effective amount of a carrier protein-hapten complex; and administering a targeting compound to the subject; thereby generating a covalent polyclonal antibody response to a target antigen.

The target antigen can be any antigen such as a tumor antigen, a cancer antigen, a self antigen, a toxin, a bacterial antigen, a viral antigen, or an integrin. For example, the integrin can be $\alpha_v\beta_3$ or $\alpha_v\beta_5$. In certain instances, when the antigen is a cancer antigen, the cancer is melanoma, colon cancer, glioma, ovarian cancer, cervical cancer, breast cancer, prostate cancer, lung cancer, a hematopoietic cancer, or head and neck cancer.

In one aspect, the carrier protein is selected from KLH, BSA and ovalbumin.

The disclosure provides an enriched population of covalent polyclonal antibodies produced by the subject following the methods of the disclosure.

In another embodiment, the disclosure provides a method of treating or preventing a disease or condition in a subject wherein the disease or condition involves cells, tissue or fluid that expresses a target molecule. The method includes preimmunizing a subject with an immunizing effective amount of a carrier protein-hapten complex; and administering an targeting compound molecule to the subject; thereby inducing a covalent polyclonal antibody response in the subject and treating or preventing the disease or condition.

In one aspect, the disease or condition is an infection and the target molecule is expressed by a microbial agent or virus.

In yet another embodiment, the disclosure provides a method of treating or preventing a disease or condition in a subject wherein the disease or condition involves cells, tissue or fluid that expresses a target molecule. The method includes administering to a subject in need thereof, an antibody produced by the method of the disclosure in combination with a targeting compound.

The disclosure includes administration topically, orally or other means known in the art.

BRIEF DESCRIPTION OF THE DRAWINGS

FIG. 16 illustrates an HIV-1 viral envelope targeting agent based on BMS-378806 (AIDS, 2004 Nov. 19; 18:2327-30; Antivir Ther—2002; 7 (Suppl 1):S1-251).

FIG. 17 illustrates a chemically programmed vaccine approach that blocks HIV-1 transmission.

DETAILED DESCRIPTION OF THE DISCLOSURE

Figure 1A:
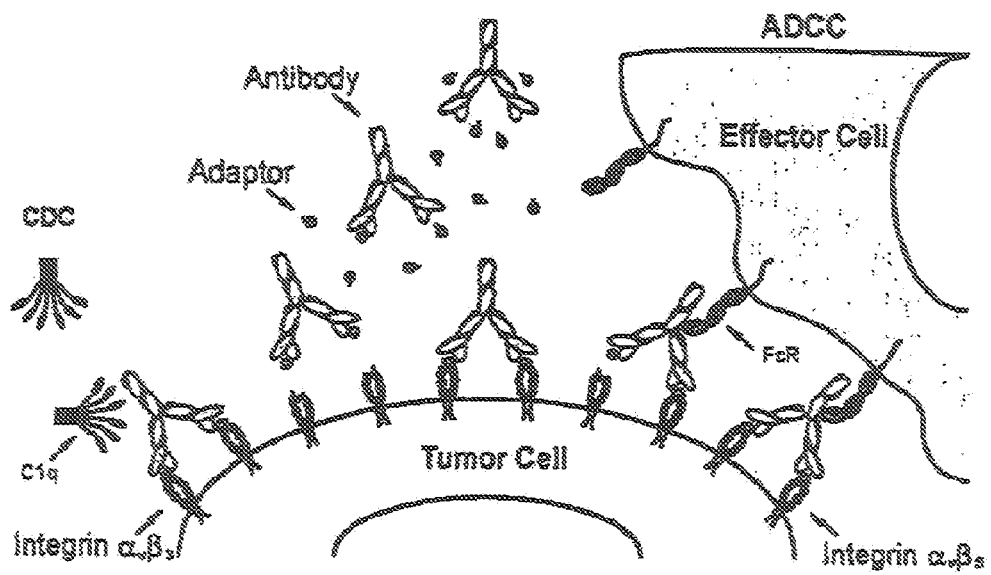
FIG. 1 illustrates antibody redirection by chemical programming: (A) After programming with a chemical adaptor, the anti-JW hapten antibodies recognize $\alpha_v\beta_3$ and $\alpha_v\beta_5$ on cancer cell surfaces. (B) Structure of the JW hapten, SCS-873 and cRGD-dk chemical adaptors, and SCS-397 and cRGD control ligands that lack diketone tags.

In order to address the challenges in vaccine development, reactive immunization was developed as an approach for inducing a covalent-binding antibody response. Reactive immunization was originally designed for the generation of catalytic monoclonal antibodies and differs from the usual immunization approaches in that reactive chemicals designed to elicit covalent antibodies are used as immunogens. It has previously been shown that immunization with β-diketone immunogens allows for the reproducible induction of covalent antibodies that can be utilized to catalyze enamine- and iminium-based transformations like the Aldol reaction. It has also been shown that covalent monoclonal antibodies can be programmed via their covalent reaction with designed ligands of a variety of specificities and that such chemically programmed antibodies possess potent biological activities in a variety of animal models of disease. Indeed, several human trials are ongoing to explore the efficacy of chemically programmed monoclonal antibodies in treatment of human disease. Given these successes, covalent polyclonal responses might be efficiently induced in vivo to produce a therapeutic outcome. It is demonstrated herein that the induced polyclonal response can be programmed by injection of a suitably designed programming compound to provide treated animals with 'instant immunity.'

The ability to instantly create a state of immunity as achieved in the passive transfer of hyperimmune globulin has had a tremendous impact on public health. Unlike passive immunization, active immunization, which is the foundation of vaccinology, is an anticipatory strategy with inherent limitations. Elements of active and passive immunization, however, can be combined to create an effective chemistry-driven approach to vaccinology. Reactive immunization was used to create a reservoir of covalent polyclonal antibodies in three mouse strains that were subsequently engrafted with syngeneic CT26 colon or B16F10 melanoma tumors. Upon administration of designed integrin αvβ3 and αvβ5 adapter ligands, the induced covalent polyclonal antibodies self-assembled with the adapter ligands and the animals mounted an instant, chemically programmed, polyclonal response against the implanted tumors. Significant therapeutic responses were observed without recourse to adjuvant therapy. The chemically programmed immune responses were driven by antibody-dependent cellular cytotoxicity and complement-directed cytotoxicity. This type of chemistry-driven approach to vaccinology may provide routes to vaccines to protect against diseases that have proven intractable to biology-driven vaccine approaches.

Thus, in one aspect the present disclosure provides an immunization approach for inducing a covalent binding antibody response in a subject.

Keyhole limpet hemocyanin (KLH) is used extensively as a carrier protein in the production of antibodies for research, biotechnology and therapeutic applications. Haptens are substances with a low molecular weight such as peptides, small proteins and drug molecules that are generally not immunogenic and require the aid of a carrier protein to stimulate a response from the immune system in the form of antibody production. KLH is the most widely employed carrier proteins for this purpose. KLH is an effective carrier protein for several reasons. Its large size and distinct/foreign epitopes generate a substantial immune response, and its abundance of lysine residues available for coupling haptens allows a high hapten:carrier protein ratio, which increases the likelihood of generating hapten-specific antibodies.

Haptens can be coupled to KLH using several methods. A simple one-step coupling can be performed using the crosslinker EDC to covalently attach carboxyls to primary amines. This method is the simplest to perform and the "random" orientation allows for antibody generation against all possible epitopes. This procedure, however, generally results in some degree of polymerization, which decreases solubility making the conjugate more difficult to handle.

KLH can be activated with the crosslinker Sulfo-SMCC, which converts lysine residues to sulfhydryl-reactive maleimide groups. A sulfhydryl-containing hapten can then be reacted with KLH to complete the immunogen without causing polymerization. The specificity of this reaction is ideal for situations where the cysteine is located away from the desired epitope (e.g. in peptides where a terminal cysteine can be added to either end of the peptide). Maleimide activated KLH, where the first part of this two step procedure has been completed, is commercially available. While KLH is used as an exemplary molecule in the present disclosure, it should be understood that other carrier proteins, including Concholepas concholepas hemocyanin (marketed as Blue Carrier); Bovine serum albumin (BSA); Cationized BSA (cBSA); Ovalbumin and others are also included in the disclosed methods.

The present disclosure provides various antibody targeting compounds in which targeting agents and/or biological agents are covalently linked to the combining site of an antibody. When one or more targeting agents are linked, at least one of the targeting agents may be linked so that it can bind its target. This may be achieved by linking the targeting agent in a manner that does effect its binding specificity for the target and by sufficiently distancing the targeting agent from the antibody combining site so that it can bind its target without steric hindrance by the antibody.

Targeting agents include, but are not limited to, small molecule organic compounds of 5,000 daltons or less such as drugs, proteins, peptides, peptidomimetics, glycoproteins, proteoglycans, lipids glycolipids, phospholipids, lipopolysaccharide, nucleic acids, proteoglycans, carbohydrates, and the like. Targeting agents may include well known therapeutic compounds including anti-neoplastic agents. Anti-neoplastic targeting agents may include targpaclitaxel, daunorubicin, doxorubicin, caminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthalen-eacetate, vinblastine, vincristine, mitomycin C, N-methyl mitomycin C, bleomycin $A_2$, dideazatetrahydrofolic acid, aminopterin, methotrexate, cholchicine and cisplatin, and the like. Antimicrobial agents include aminoglycosides including gentamicin, antiviral compounds such as rifampicin, 3'-azido-3'-deoxythymidine (AZT) and acylovir, antifungal agents such as azoles including fluconazole, plyre macrolides such as amphotericin B, and candicidin, anti-parasitic compounds such as antimonials, and the like. Hormone targeting agents include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, and hormone receptors such as the estrogen receptor.

In some embodiments, the targeting agent is not an antibody. In other embodiments, the targeting agent is not a metal chelate. The targeting agent may be a small molecule as compared with a native immunoglobulin. The targeting agent, including any linking moiety necessary for covalently linking the targeting agent to an amino acid residue of the antibody combining site, may be at least about 300 daltons in size, and may be at least about 400, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500 or even 5,000 daltons in size, with even larger sizes possible.

Suitable targeting agents in targeting compounds of the disclosure can be a protein or peptide. "Polypeptide", "peptide," and "protein" are used interchangeably to refer to a polymer of amino acid residues. As used herein, these terms apply to amino acid polymers in which one or more amino acid residue is an artificial chemical analogue of a corresponding naturally occurring amino acid. These terms also apply to naturally occurring amino acid polymers. Amino acids can be in the L or D form as long as the binding function of the peptide is maintained. Peptides can be of variable length, but are generally between about 4 and 200 amino acids in length. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well know in the art, for example, see e.g., U.S. Pat. No. 6,013,625.

Protein or peptide targeting agents that exhibit binding activity for a target molecule are well known in the art. For example, a targeting agent may be a viral peptide cell fusion inhibitor. This may include the T-20 HIV-1 gp41 fusion inhibitor which targets fusion receptors on HIV infected cells (for T-20, see U.S. Pat. Nos. 6,281,331 and 6,015,881 to Kang et al.; Nagashima et al. J. Infectious Diseases 183:1121, 2001; for other HIV inhibitors see U.S. Pat. No. 6,020,459 to Barney and WO 0151673A2 to Jeffs et al), RSV cell fusion inhibitors (see WO 0164013A2 to Antczak and McKimm-Breschkin, Curr. Opin. Invest. Drugs 1:425-427, 2000 (VP-14637)), pneumovirus genus cell fusion inhibitors (see WO 9938508A1 by Nitz et al.), and the like. Targeting agents also include peptide hormones or peptide hormone analogues such as LHRH, bombesin/gastrin releasing peptide, somatastatin (e.g., RC-121 octapeptide), and the like, which may be used to target any of a variety of cancers ovarian, mammary, prostate small cell of the lung, colorectal, gastric, and pancreatic. See, e.g., Schally et al., Eur. J. Endocrinology, 141: 1-14, 1999.

Peptide targeting agents suitable for use in targeting compounds of the disclosure also may be identified using in vivo targeting of phage libraries that display a random library of peptide sequences (see, e.g., Arap et al., Nature Medicine, 2002 8(2):121-7; Arap et al., Proc. Natl. Acad. Sci. USA 2002 99(3):1527-1531; Trepel et al. Curr. Opin. Chem. Biol. 2002 6(3):399-404).

In some embodiments, the targeting agent is specific for an integrin. Integrins are heterodimeric transmembrane glycoprotein complexes that function in cellular adhesion events and signal transduction processes. Integrin $\alpha v \beta 3$ is expressed on numerous cells and has been shown to mediate several biologically relevant processes, including adhesion of osteoclasts to bone matrix, migration of vascular smooth muscle cells, and angiogenesis. Integrin $\alpha v \beta 3$ antagonists likely have use in the treatment of several human diseases, including diseases involving neovascularization, such as rheumatoid arthritis, cancer, and ocular diseases.

Suitable targeting agents for integrins include RGD peptides or peptidomimetics or non-RGD peptides or peptidomimetics. As used herein, reference to "Arg-Gly-Asp peptide" or "RGD peptide" is intended to refer to a peptide having one or more Arg-Gly-Asp containing sequence which may function as a binding site for a receptor of the "Arg-Gly-Asp family of receptors", e.g., an integrin. Integrins, which comprise and alpha and a beta subunit, include numerous types including $\alpha 1\beta 1$, $\alpha 2\beta 1$, $\alpha 3\beta 1$, $\alpha 4\beta 1$, $\alpha 5\beta 1$, $\alpha 6\beta 1$, $\alpha 7\beta 1$, $\alpha 8\beta 1$, $\alpha 9\beta 1$, $\alpha 6\beta 4$, $\alpha 4\beta 7$, $\alpha D\beta 2$, $\alpha v\beta 6$, $\alpha L\beta 2$, $\beta M\beta 2$, $\alpha 4\beta 7$, $\alpha v\beta 1$, $\alpha v\beta 3$, $\alpha v\beta 5$, $\alpha v\beta 6$, $\alpha v\beta 8$, $\alpha x\beta 2$, $\alpha IIb\beta 3$, $\alpha IELb\beta 7$ and the like.

The sequence RGD is present in several matrix proteins and is the target for cell binding to matrix by integrins. Platelets contain a large amount of RGD-cell surface receptors of the protein GP IIb/IIIc, which is primarily responsible, through interaction with other platelets and with the endothelial surface of injured blood vessels, for the development of coronary artery thrombosis. The term RGD peptide also includes amino acids that are functional equivalents (e.g., RLD or KGD) thereof provided they interact with the same RGD receptor. Peptides containing RGD sequences can be synthesized from amino acids by means well known in the art, using, for example, an automated peptide synthesizer, such as those manufactured by Applied Biosystems, Inc., Foster City, Calif.

As used herein, "non-RGD" peptide refers to a peptide that is an antagonist or agonist of integrin binding to its ligand (e.g. fibronectin, vitronectin, laminin, collagen etc.) but does not involve an RGD binding site. Non-ROD integrin peptides are known for $\alpha v \beta 3$ (see, e.g., U.S. Pat. Nos. 5,767,071 and 5,780,426) as well as for other integrins such as $\alpha 4\beta 1$ (VLA-4), $\alpha_4\beta_7$ (see, e.g., U.S. Pat. No. 6,365,619; Chang et al., Bioorganic & Medicinal Chem Lett, 12:159-163 (2002); Lin et al., Bioorganic & Medicinal Chem Lett, 12:133-136 (2002)), and the like.

An integrin targeting agent may be a peptidomimetic agonist or antagonist, which may be a peptidomimetic agonist or antagonist of an RGD peptide or non-RGD peptide. As used herein, the term "peptidomimetic" is a compound containing non-peptidic structural elements that are capable of mimicking or antagonizing the biological action(s) of a natural parent peptide. A peptidomimetic of an RGD peptide is an organic molecule that retains similar peptide chain pharmacophore groups of the ROD amino acid sequence but lacks amino acids or peptide bonds in the binding site sequence. Likewise, a peptidomimetic of a non-RGD peptide is an organic molecule that retains similar peptide chain pharmacophore groups of the non-RGD binding site sequence but lacks amino acids or peptide bonds in the binding site sequence. A "pharmacophore" is a particular three-dimensional arrangement of functional groups that are required for a compound to produce a particular response or have a desired activity. The term "RGD peptidomimetic" is intended to refer to a compound that comprises a molecule containing the RGD pharmacophores supported by an organic/non-peptide structure. It is understood that an RGD peptidomimetic (or non-RGD peptido-mimetic) may be part of a larger molecule that itself includes conventional or modified amino acids linked by peptide bonds.

RGD peptidomimetics are well known in the art, and have been described with respect to integrins such as GPIIb/IIIa, αvβ3 and αvβ5 (See, e.g., Miller et al., J. Med. Chem. 2000, 43:22-26; and International Patent Publications WO 0110867, WO 9915178, WO 9915170, WO 9815278, WO 9814192, WO 0035887, WO 9906049, WO 9724119 and WO 9600730; see also Kumar et al., Cancer Res. 61:2232-2238 (2000)). Many such compounds are specific for more than one integrin. RGD peptidomimetics are generally based on a core or template (also referred to as "fibrinogen receptor antagonist template"), which are linked by way of spacers to an acidic group at one end and a basic group at the other end of the core. The acidic group is generally a carboxylic acid functionality while the basic group is generally a N-containing moiety such as an amidine or guanidine. Typically, the core structure adds a form of rigid spacing between the acidic moiety and the basic nitrogen moiety, and contains one or more ring structures (e.g., pyridine, indazole, etc.) or amide bonds for this purpose.

For a fibrinogen receptor antagonist, generally, about twelve to fifteen, more may be thirteen or fourteen, intervening covalent bonds are present (via the shortest intramolecular path) between the acidic group of the ROD peptidomimetic and a nitrogen of the basic group. The number of intervening covalent bonds between the acidic and basic moiety is generally shorter, two to five, or three or four, for a vitronectin receptor antagonist. The particular core may be chosen to obtain the proper spacing between the acidic moiety of the fibrinogen antagonist template and the nitrogen atom of the pyridine. Generally, a fibrinogen antagonist will have an intramolecular distance of about 16 angstroms (1.6 nm) between the acidic moiety (e.g., the atom which gives up the proton or accepts the electron pair) and the basic moiety (e.g., which accepts a proton or donates an electron pair), while a vitronectin antagonist will have about 14 angstroms (1.4 nm) between the respective acidic and basic centers. Further description for converting from a fibrinogen receptor mimetic to a vitronectin receptor mimetic can be found in U.S. Pat. No. 6,159,964.

The peptidomimetic RGD core can comprise a 5-11 membered aromatic or nonaromatic mono- or polycyclic ring system containing 0 to 6 double bonds, and containing 0 to 6 heteroatoms chosen from N, O and S. The ring system may be unsubstituted or may be substituted on a carbon or nitrogen atom. Core structures with suitable substituents useful for vitronectin binding include monocyclic and bicyclic groups, such as benzazapine described in WO 98/14192, benzdiazapine described in U.S. Pat. No. 6,239,168, and fused tricyclics described in U.S. Pat. No. 6,008,213.

U.S. Pat. No. 6,159,964 contains an extensive list of references in Table 1 of that document which disclose RGD peptidomimetic cores structures (referred to as fibrinogen templates), which can be used for preparing RGD peptidomimetics. Vitronectin RGD and fibronectin RGD peptidomimetics are disclosed in U.S. Pat. Nos. 6,335,330; 5,977,101; 6,088,213; 6,069,158; 6,191,304; 6,239,138; 6,159,964; 6,117,101; 6,117,866; 6,008,214; 6,127,359; 5,939,412; 5,693,636; 6,403,578; 6,387,895; 6,268,378; 6,218,387; 6,207,663; 6,011,045; 5,990,145; 6,399,620; 6,322,770; 6,017,925; 5,981,546; 5,952,341; 6,413,955; 6,340,679; 6,313,119; 6,268,378; 6,211,184; 6,066,648; 5,843,906; 6,251,944; 5,952,381; 5,852,210; 5,811,441; 6,114,328; 5,849,736; 5,446,056; 5,756,441; 6,028,087; 6,037,343; 5,795,893; 5,726,192; 5,741,804; 5,470,849; 6,319,937; 6,172,256; 5,773,644; 6,028,223; 6,232,308; 6,322,770; 5,760,028 and U.S. Patent Application Publication No. 2003/0175921.

The target molecule to which the targeting agent of the targeting compound binds is may be a non-immunoglobulin molecule or may be an immunoglobulin molecule where the target moiety is outside the immunoglobulin combining site. It is not intended to exclude from the disclosed compounds those targeting agents that function as antigens and, therefore, bind to an immunoglobulin combining site. Such targeting agents are included herein provided the targeting agents also bind to a non-immunoglobulin molecule and/or a target moiety located outside the combining site of an immunoglobulin molecule. In general, the target molecule can be any type of molecule including organic, inorganic, protein, lipid, carbohydrate, nucleic acid and the like.

The target molecule may be a biomolecule such as a protein, carbohydrate, lipid or nucleic acid. The target molecule can be associated with a cell ("cell surface expressed"), or other particle ("particle surface expressed") such as a virus, or may be extracellular. If associated with a cell or particle, the target molecule is may be expressed on the surface of the cell or particle in a manner that allows the targeting agent of the targeting compound to make contact with the surface receptor from the fluid phase of the body.

In some embodiments, the target molecule is predominantly or exclusively associated with a pathological condition or diseased cell, tissue or fluid. Thus, the targeting agent of a present antibody targeting compound can be used to deliver the targeting compound to a diseased tissue by targeting the cell, an extracellular matrix biomolecule or a fluid biomolecule. Exemplary target molecules disclosed hereinafter in the Examples include integrins (as illustrated herein), cytokine receptors, cytokines, vitamin receptors, cell surface enzymes, pathogens such as viral and bacterial pathogens (e.g., HIV-1 virus and HIV-1 virus infected cells, and the like.

In one embodiment as alluded to above, the target molecule is associated with an infectious agent and is expressed on the surface of a microbial cell or on the surface of a viral particle. As such, antibody targeting compositions in which the targeting agent can bind to the cell surface expressed or particle expressed infectious agent can be used as an anti-microbial, by targeting microbial agents inside the body of an individual.

Another target molecule of the disclosure is prostate specific antigen (PSA), a serine protease that has been implicated in a variety of disease states including prostate cancer, breast cancer and bone metastasis.

"Antibody" as used herein includes immunoglobulins which are the product of B cells and variants thereof as well as the T cell receptor (TcR) which is the product of T cells and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The present disclosure also includes methods of modifying the combining site of an antibody to generate binding specificity for a particular target molecule in vivo. Such methods include covalently linking a reactive amino acid side chain in the combining site of the antibody. Typically, the antibody will not be considered specific for the target molecule.

As used herein, pharmacokinetics refers to the concentration an administered compound in the serum over time. Pharmacodynamics refers to the concentration of an administered compound in target and nontarget tissues over time and the effects on the target tissue (efficacy) and the non-target tissue (toxicity).

The disclosure also provides a method of treating or preventing a disease or condition in an individual by inducing a covalent polyclonal antibody response, wherein the disease or condition involves cells, tissue or fluid that expresses a target molecule. The method includes administering to a subject such as a patient, a pre-immunizing effective amount of haptenized KLH or other carrier protein. Subsequently, following initial immunization with the KLH-hapten molecule, the subject is administered a reactive immunogen or targeting compound corresponding to the condition. For example, the reactive immunogen (also referred to as a "chemical adapter") includes a small molecule chemical compound, a peptide or other immunogen as described herein. Illustrative reactive immunogens as used herein include SCS-873 and cRGD-dk.

As used herein, the term "covalent antibody" refers to an antibody of the disclosure that is not released following treatment with acid (e.g., 0.05M citric acid, pH 2.5). Thus, the covalent antibodies of the disclosure are considered acid stable molecules.

The subject may be an animal such as a mammal. In some embodiments, the subject is a human. In some embodiments, the target molecule is an integrin and the disease is a carcinoma. The association of integrin expression in carcinomas is well known in the art, for example, U.S. Pat. Nos. 5,753,230 and 5,766,591, the disclosures of which are incorporated herein by reference.

In one aspect, the disclosure includes an enriched population of covalent polyclonal antibodies produced by the method of the disclosure. Such a population of antibodies are useful in a variety of therapeutic applications including the imaging of cells such as tumor cells or tissues (e.g., an extracellular matrix biomolecule) as is well known in the art. Accordingly, provided is a method of imaging cells or tissue (e.g., an extracellular matrix biomolecule) in an individual. In such methods, the cells or tissue expresses a target molecule. The method includes administering to a subject a covalent polyclonal antibody or antibodies of the disclosure linked to a detectable label. A detectable label for use in such methods can be a radioisotope or may be a non-radioisotope such as may be used in nuclear magnetic resonance (NMR) imaging. In the latter case, one may link the antibody targeting agent to chelates e.g., diethylenetriaminepentaacetate (DTPA) of the paramagnetic metal gadolinium essentially as described in Simkins et al., Nat. Med., 4(5):623-6 (1998).

It would be readily evident that the antibodies of the disclosure find use not only in human medical therapy and diagnosis but also in veterinary, agricultural, environmental and other disciplines.

In another aspect the disclosure provides a compound of formula I:

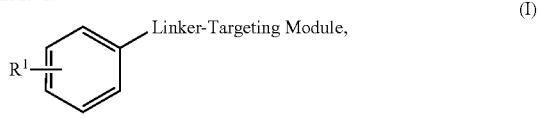

(I)

or a pharmaceutically acceptable salt thereof, wherein:

Linker is independently selected from —O—, —NH—, —S—, —($C_1$-$C_{20}$)alkyl-, —($CH_2CH_2O$)$_m$—, —NHC(=O)($CH_2$)$_n$—, —C(=O)($CH_2$)$_q$—,

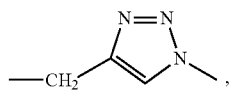

and combinations thereof, wherein m, n, and q are each independently an integer from 0 to 20;

$R^1$ is independently

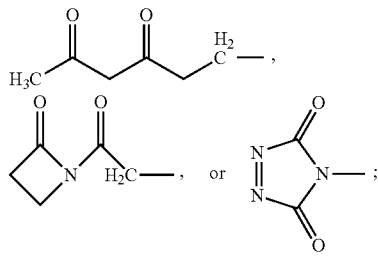

and

Targeting Module is a therapeutic compound.

In another aspect the disclosure provides a compound of formula II:

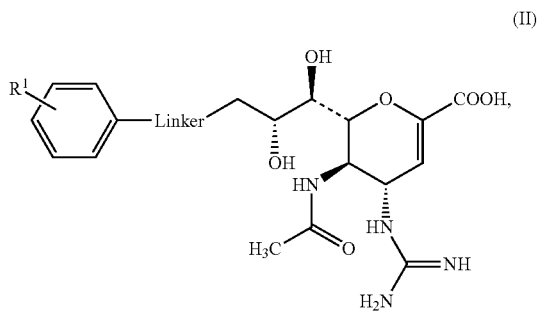

(II)

wherein the Linker is:
—NHC(=O)(CH₂)₃C(=O)NH—,
—NHC(=O)(CH₂)₃C(=O)NH(CH₂)₃—,
—NHC(=O)(CH₂)₃C(=O)NH(CH₂)₂(OCH₂CH₂)₂—,
—(CH₂)₃NHC(=O)(CH₂)₃C(=O)NH—,
—O(CH₂CH₂O)₃(CH₂)₂NHC(=O)(CH₂)₃C(=O)NH—,
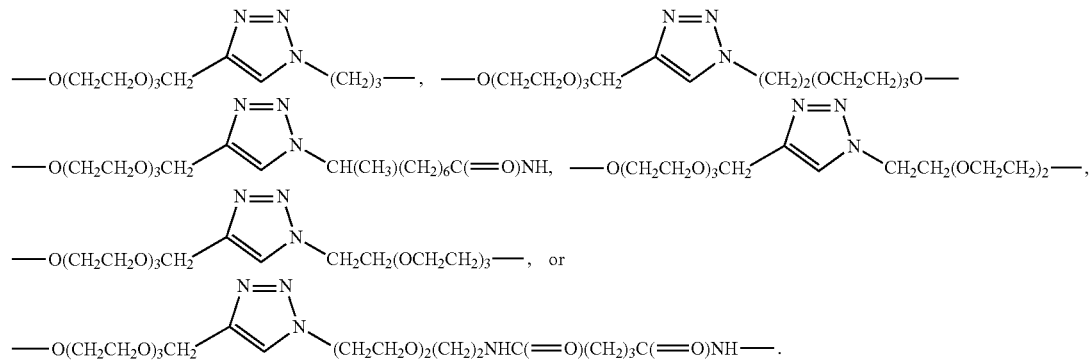
In another aspect the disclosure provides a compound of formula:
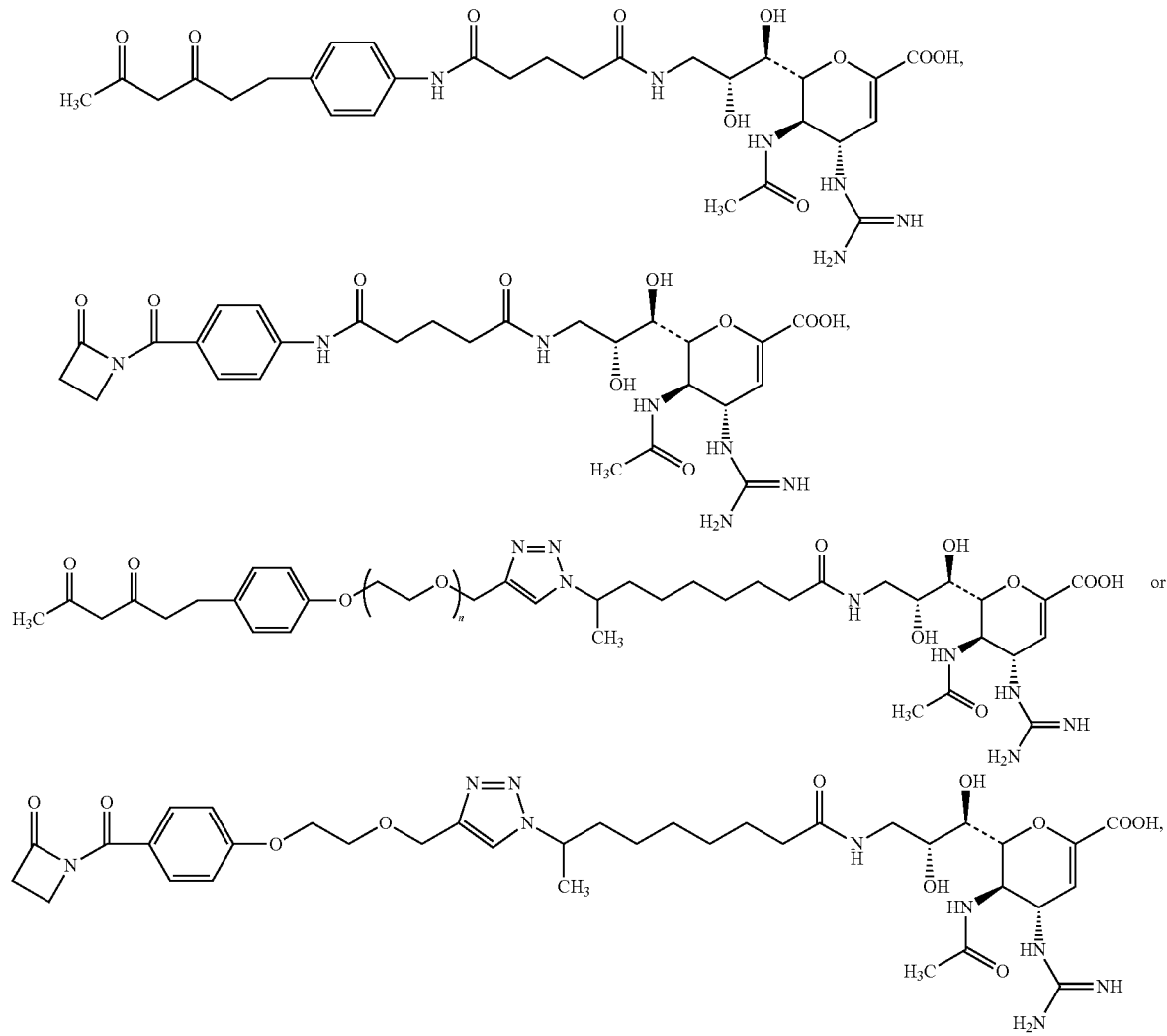
wherein each n is independently an integer from 0 to 20.

In another aspect the disclosure provides a compound of formula III or formula III':

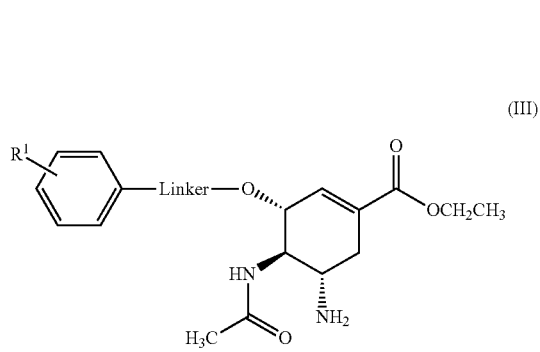

(III)

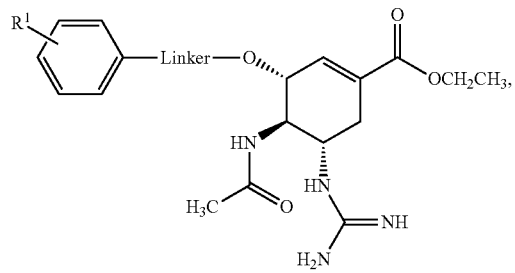

(III')

wherein the Linker is:
—NHC(=O)(CH₂)₃C(=O)NH—,
—NHC(=O)(CH₂)₃C(=O)NH(CH₂)₃—,
—NHC(=O)(CH₂)₃C(=O)NH(CH₂)₂(OCH₂CH₂)₂₋₅
—(CH₂)₃NHC(=O)(CH₂)₃C(=O)NH—,
—O(CH₂CH₂O)₃(CH₂)₂NHC(=O)(CH₂)₃C(=O)NH—, —O(CH₂CH₂O)₃CH₂—[triazole]—(CH₂)₃—,  —O(CH₂CH₂O)₃CH₂—[triazole]—(CH₂)₂(OCH₂CH₂)₃O—

—O(CH₂CH₂O)₃CH₂—[triazole]—CH(CH₃)(CH₂)₆C(=O)NH,  —O(CH₂CH₂O)₃CH₂—[triazole]—CH₂CH₂(OCH₂CH₂)₂—, —O(CH₂CH₂O)₃CH₂—[triazole]—CH₂CH₂(OCH₂CH₂)₃—, or —O(CH₂CH₂O)₃CH₂—[triazole]—(CH₂CH₂O)₂(CH₂)₂NHC(=O)(CH₂)₃C(=O)NH—.

In another aspect the disclosure provides a compound of formula:

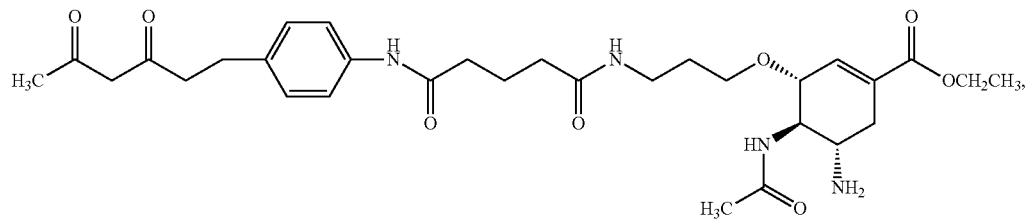

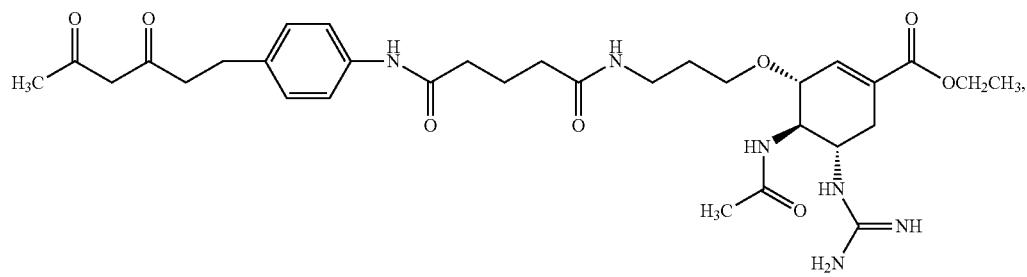

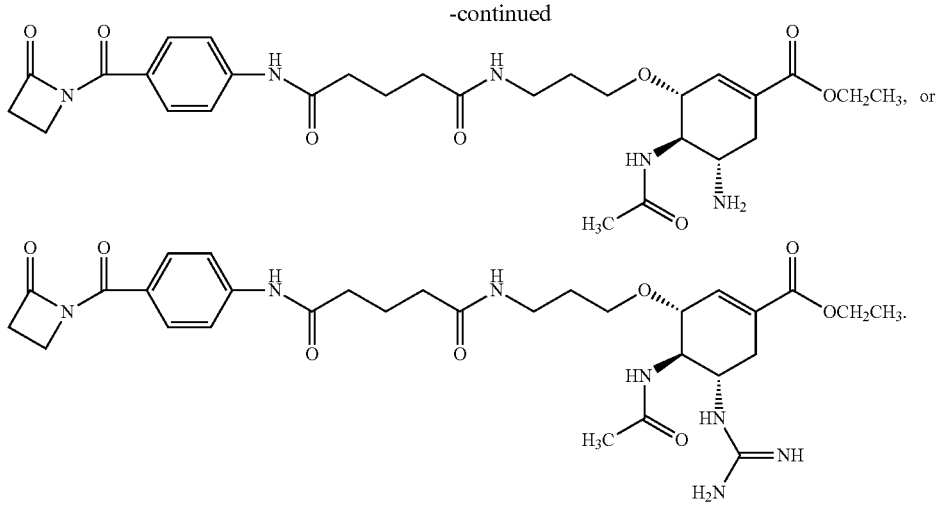
In another aspect the disclosure provides a compound of formula IV:
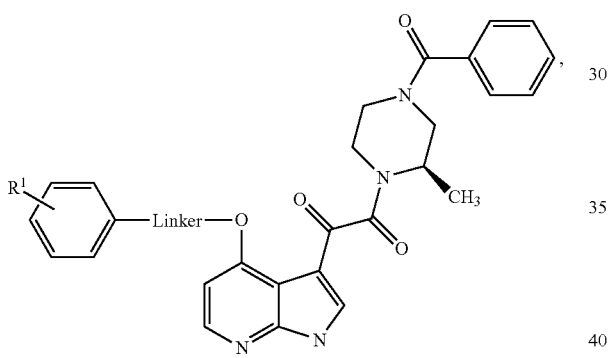
wherein the Linker is:
—NHC(═O)(CH$_2$)$_3$C(═O)NH—,
—NHC(═O)(CH$_2$)$_3$C(═O)NH(CH$_2$)$_3$—,
—NHC(═O)(CH$_2$)$_3$C(═O)NH(CH$_2$)$_2$(OCH$_2$CH$_2$)$_2$—,
—(CH$_2$)$_3$NHC(═O)(CH$_2$)$_3$C(═O)NH—,
—O(CH$_2$CH$_2$O)$_3$(CH$_2$)$_2$NHC(═O)(CH$_2$)$_3$C(═O)NH—,
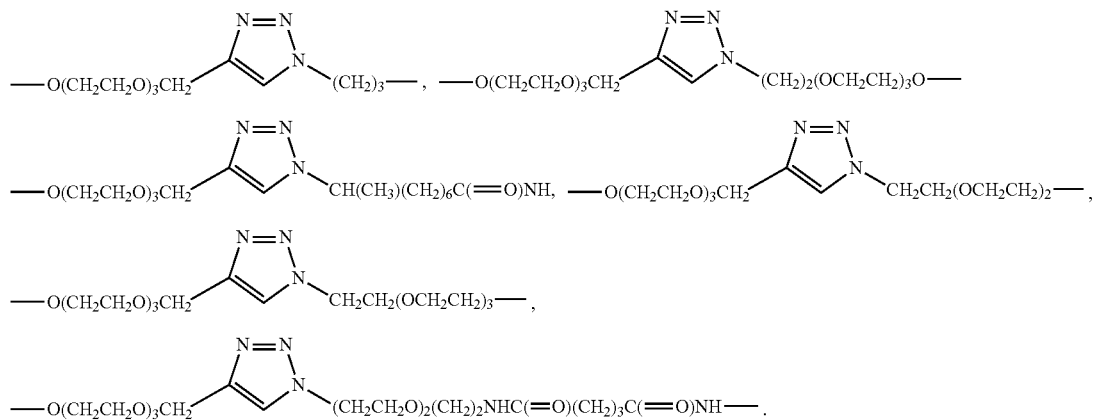

In another aspect the disclosure provides a compound of formula:
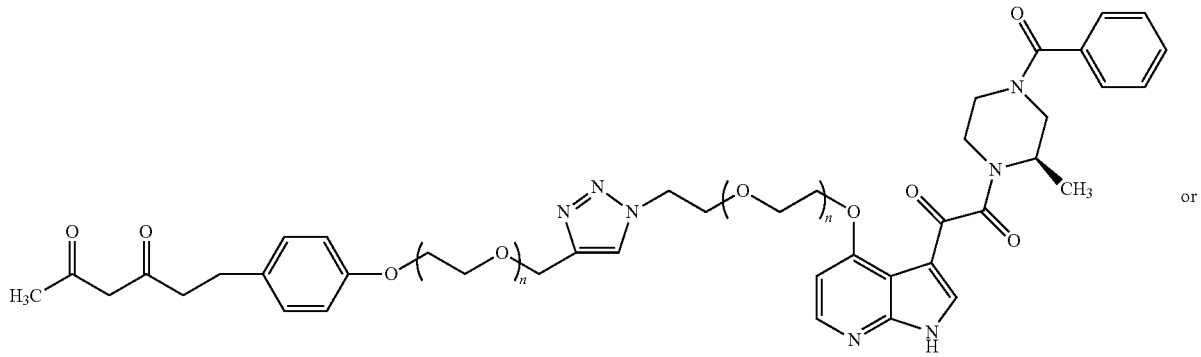 or
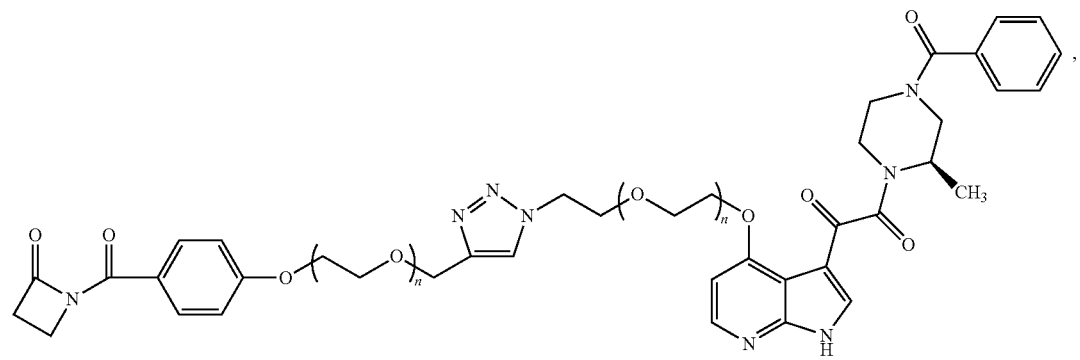,
wherein each n is independently an integer from 0 to 20.
In another aspect the disclosure provides a compound of formula V:
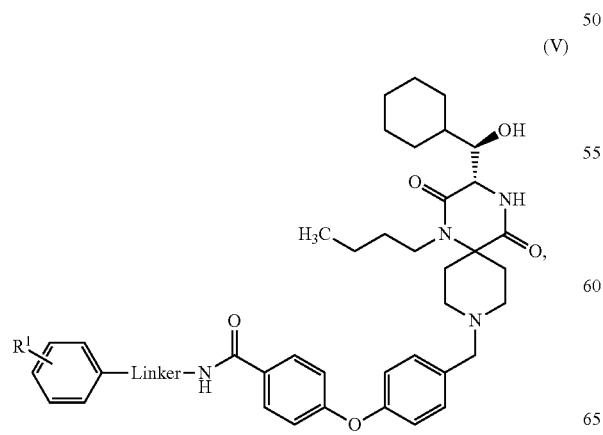
(V)

21
wherein the Linker is:
—NHC(=O)(CH₂)₃C(=O)NH—,
—NHC(=O)(CH₂)₃C(=O)NH(CH₂)₃—,
22
—NHC(=O)(CH₂)₃C(=O)NH(CH₂)₂(OCH₂CH₂)₂
—(CH₂)₃NHC(=O)(CH₂)₃C(=O)NH—,
—O(CH₂CH₂O)₃(CH₂)₂NHC(=O)(CH₂)₃C(=O)NH—,
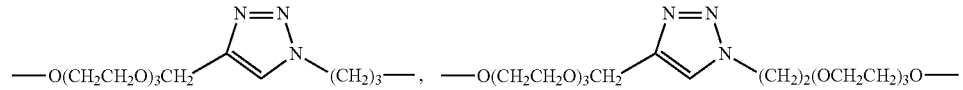
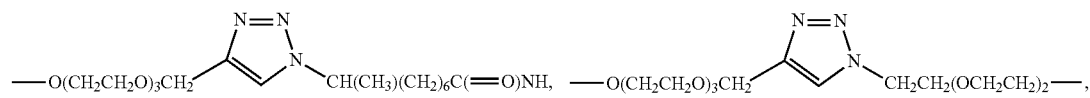
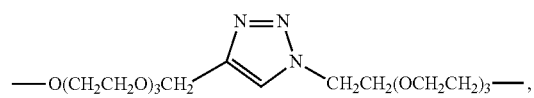
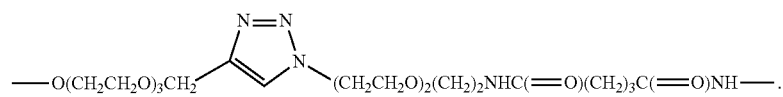
In another aspect the disclosure provides a compound of formula:
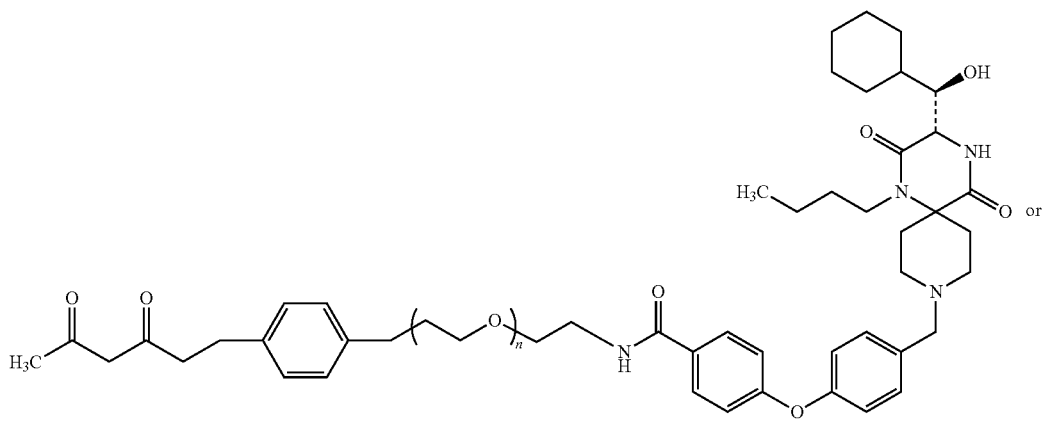
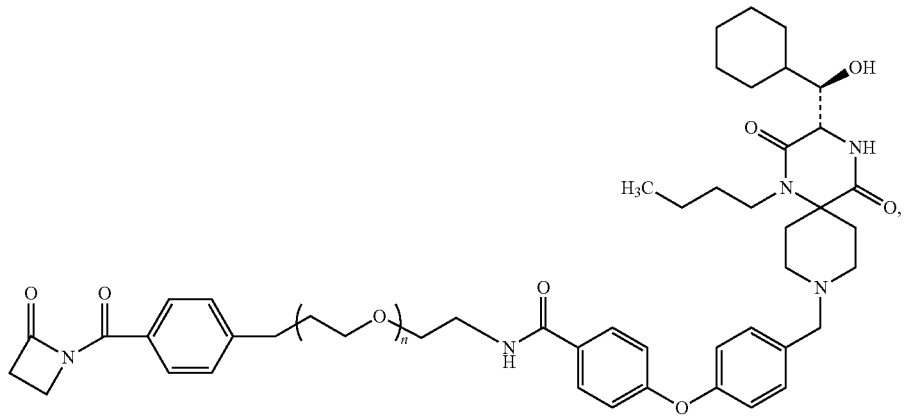
wherein each n is independently an integer from 0 to 20.

In another aspect the disclosure provides a compound of formula VI:
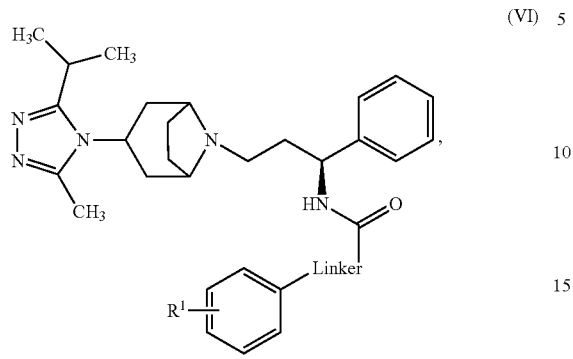
(VI)
wherein the Linker is:
—NHC(=O)(CH₂)₃C(=O)NH—,
—NHC(=O)(CH₂)₃C(=O)NH(CH₂)₃—,
—NHC(=O)(CH₂)₃C(=O)NH(CH₂)₂(OCH₂CH₂)₂
—(CH₂)₃NHC(=O)(CH₂)₃C(=O)NH—,
—O(CH₂CH₂O)₃(CH₂)₂NHC(=O)(CH₂)₃C(=O)NH—,
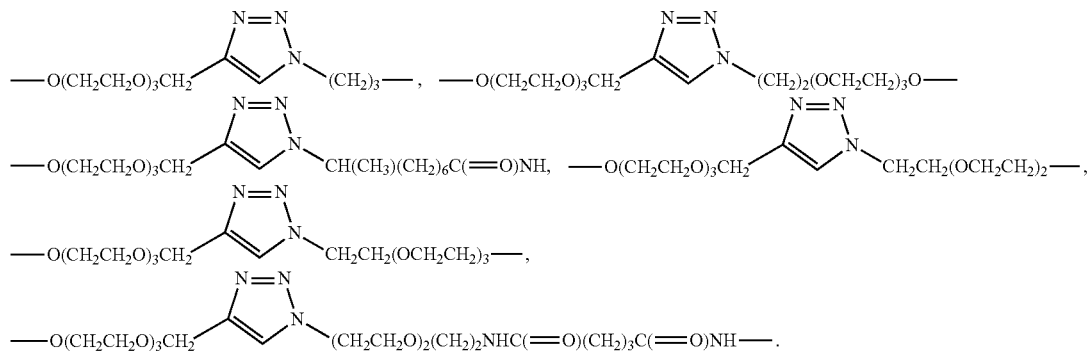
In another aspect the disclosure provides a compound of formula:
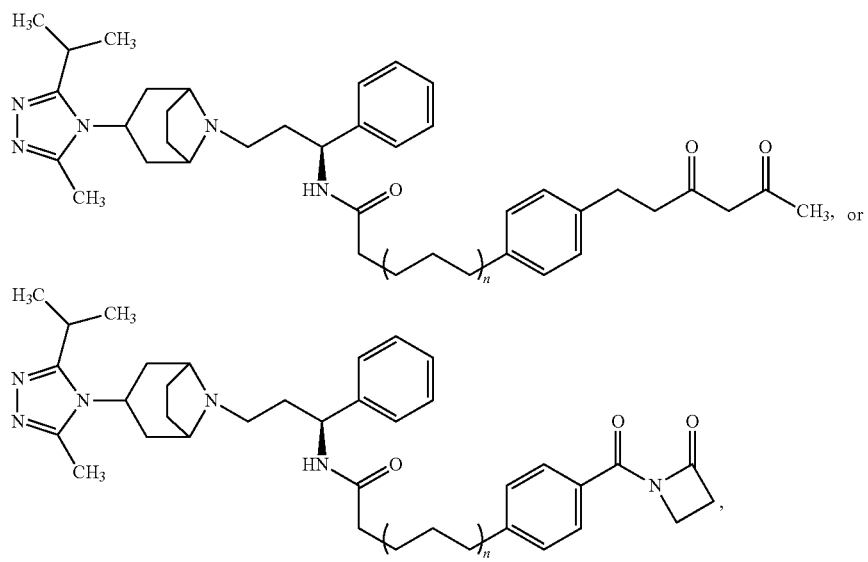
wherein each n is independently an integer from 0 to 20.

In another aspect the disclosure provides a compound of formula VII:
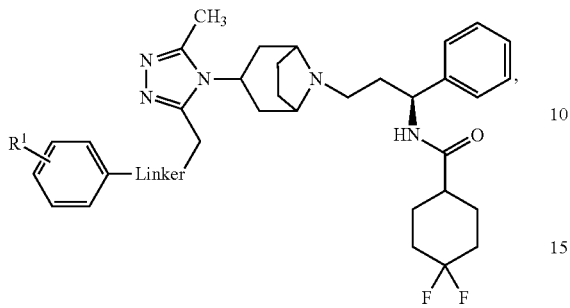
(VII)
wherein the Linker is:
—NHC(=O)(CH$_2$)$_3$C(=O)NH—,
—NHC(=O)(CH$_2$)$_3$C(=O)NH(CH$_2$)$_3$—,
—NHC(=O)(CH$_2$)$_3$C(=O)NH(CH$_2$)$_2$(OCH$_2$CH$_2$)$_2$
—(CH$_2$)$_3$NHC(=O)(CH$_2$)$_3$C(=O)NH—,
—O(CH$_2$CH$_2$O)$_3$(CH$_2$)$_2$NHC(=O)(CH$_2$)$_3$C(=O)NH—,
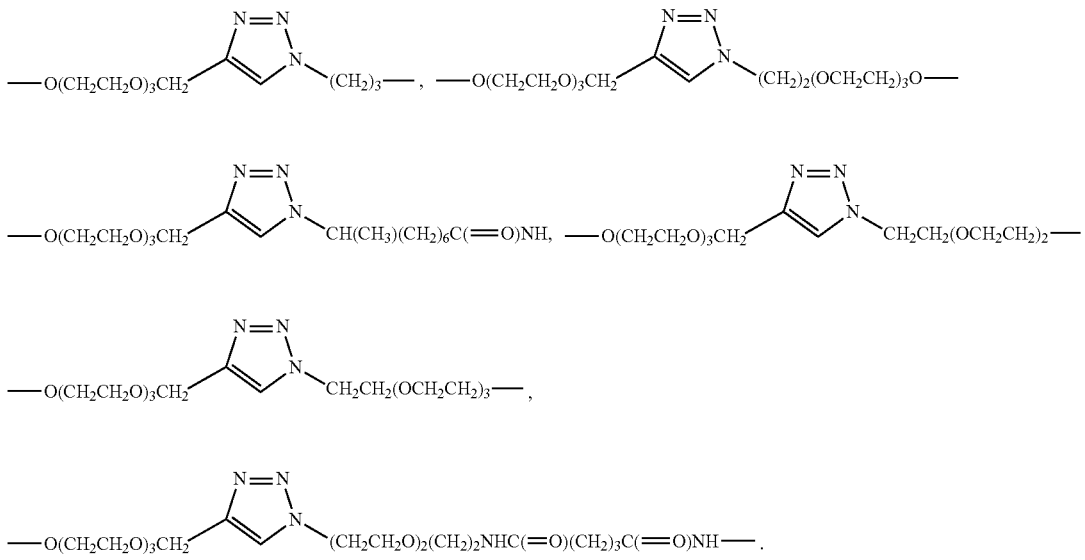
In another aspect the disclosure provides a compound of formula:
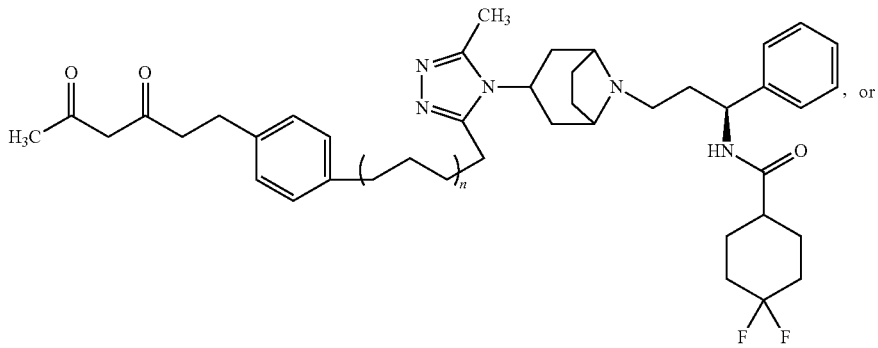
, or

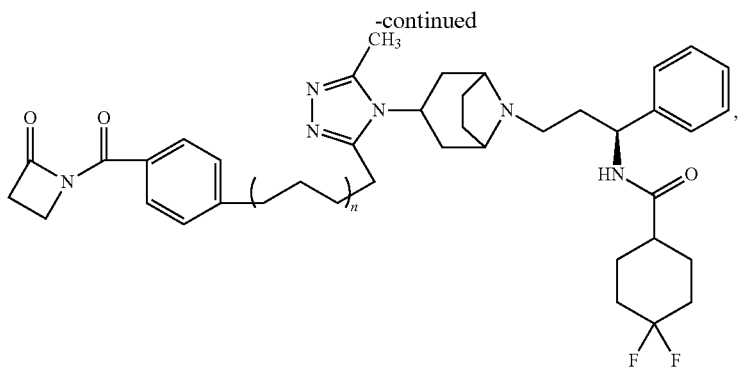
wherein each n is independently an integer from 0 to 20.
In another aspect the disclosure provides a compound of formula VIII:
(VIII)
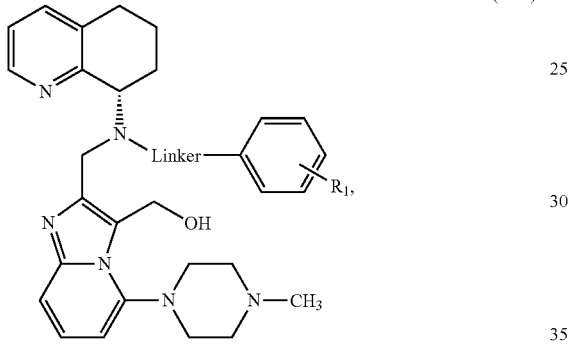
wherein the Linker is:
—NHC(=O)(CH$_2$)$_3$C(=O)NH—,
—NHC(=O)(CH$_2$)$_3$C(=O)NH(CH$_2$)$_3$—,
—NHC(=O)(CH$_2$)$_3$C(=O)NH(CH$_2$)$_2$(OCH$_2$CH$_2$)$_2$
—(CH$_2$)$_3$NHC(=O)(CH$_2$)$_3$C(=O)NH—,
—O(CH$_2$CH$_2$O)$_3$(CH$_2$)$_2$NHC(=O)(CH$_2$)$_3$C(=O)NH—,
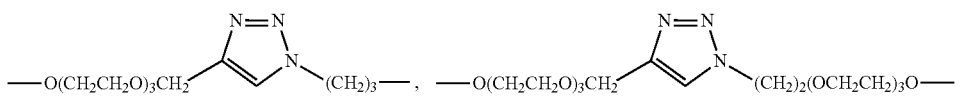
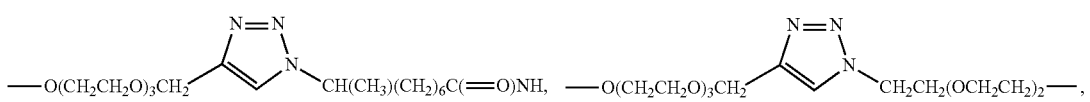
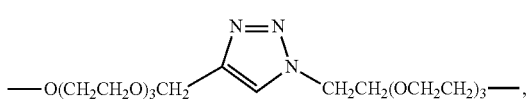
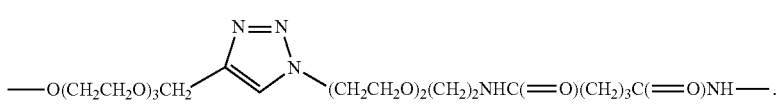

In another aspect the disclosure provides a compound of formula:
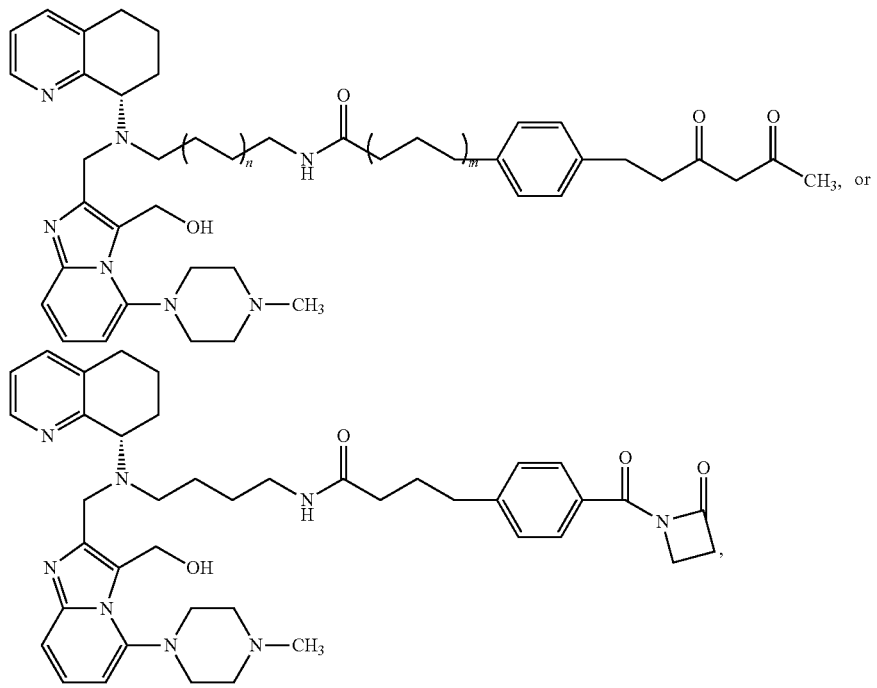
wherein each n is independently an integer from 0 to 20.
In another aspect the disclosure provides a compound of formula IX:
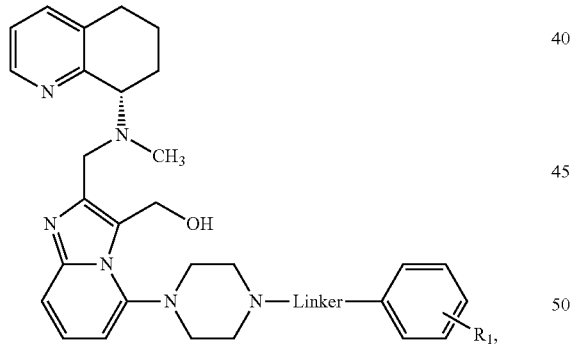
(IX)
wherein the Linker is:
—NHC(=O)(CH$_2$)$_3$C(=O)NH—,
—NHC(=O)(CH$_2$)$_3$C(=O)NH(CH$_2$)$_3$—,
—NHC(=O)(CH$_2$)$_3$C(=O)NH(CH$_2$)$_2$(OCH$_2$CH$_2$)$_2$
—(CH$_2$)$_3$NHC(=O)(CH$_2$)$_3$C(=O)NH—,
—O(CH$_2$CH$_2$O)$_3$(CH$_2$)$_2$NHC(=O)(CH$_2$)$_3$C(=O)NH—,
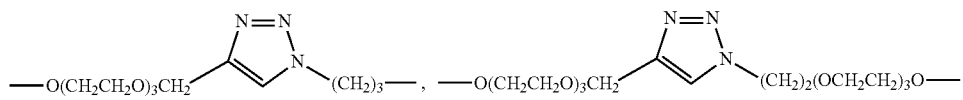

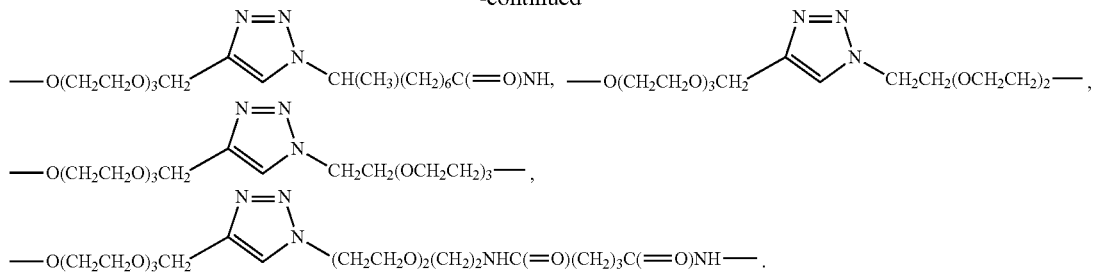
In another aspect the disclosure provides a compound of formula:
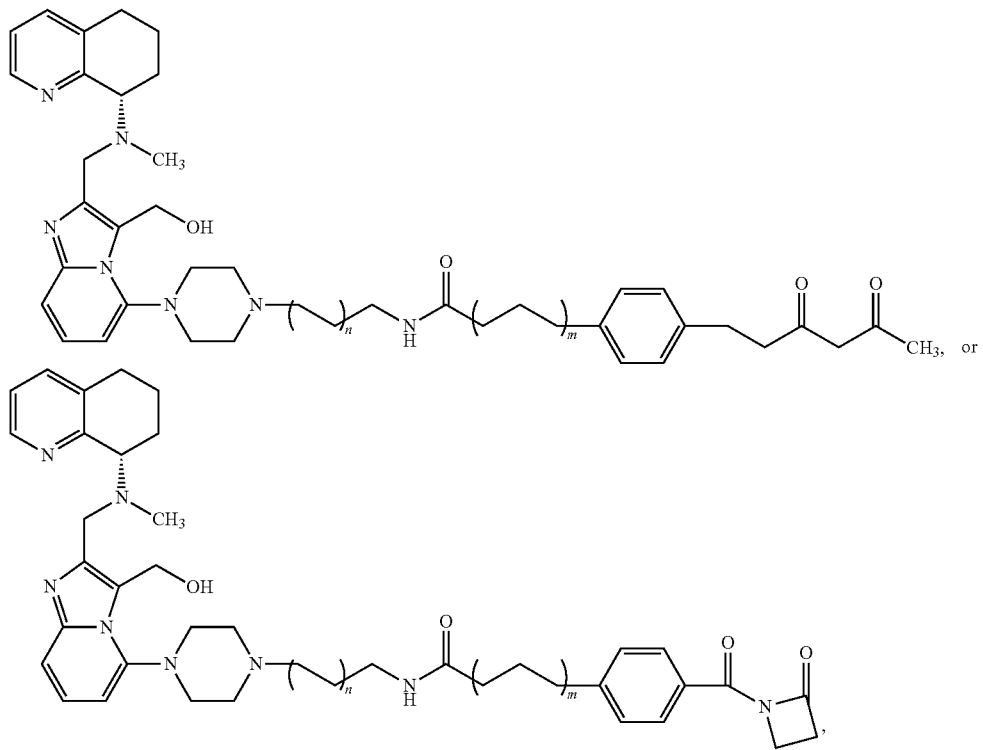
wherein each n is independently an integer from 0 to 20.
In another aspect the disclosure provides a compound of formula X or X':
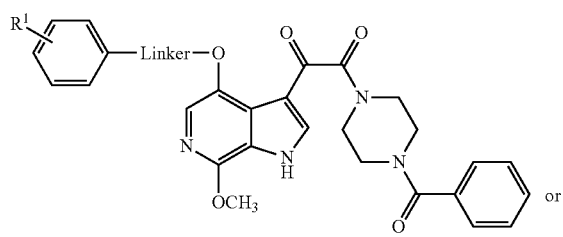
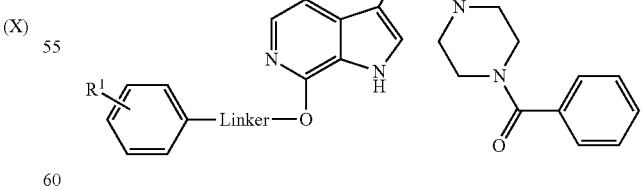
wherein the Linker is:
—NHC(=O)(CH₂)₃C(=O)NH—,
—NHC(=O)(CH₂)₃C(=O)NH(CH₂)₃—,
—NHC(=O)(CH₂)₃C(=O)NH(CH₂)₂(OCH₂CH₂)₂—
—(CH₂)₃NHC(=O)(CH₂)₃C(=O)NH—,
—O(CH₂CH₂O)₃(CH₂)₂NHC(=O)(CH₂)₃C(=O)NH—

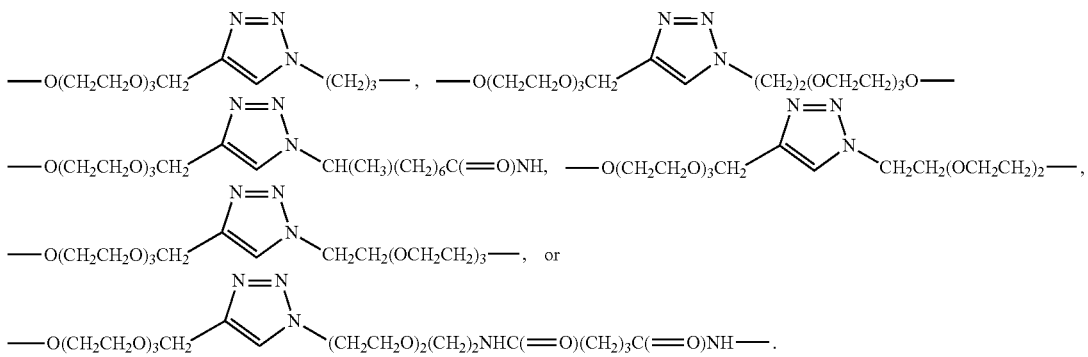

In another aspect the disclosure provides a compound of formula:

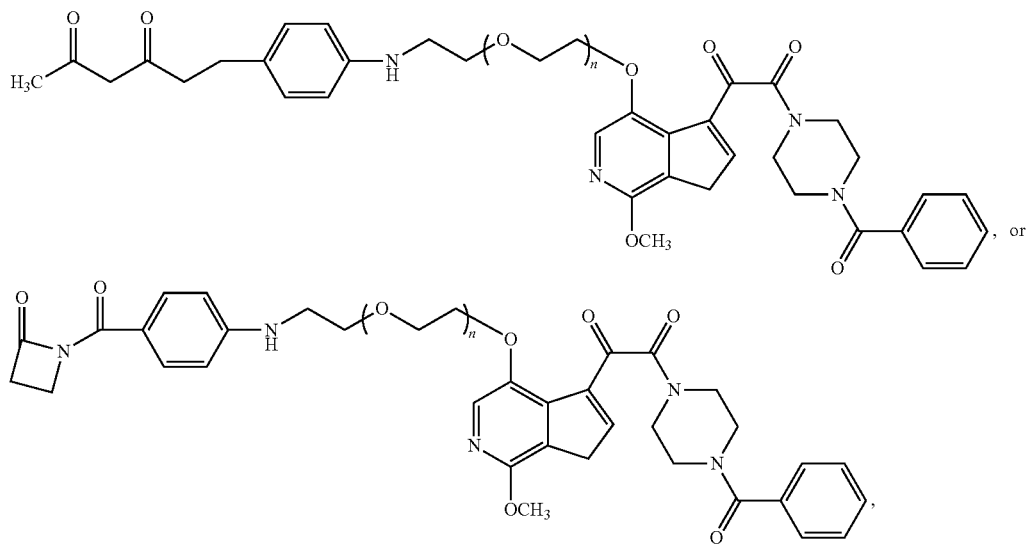

wherein each n is independently an integer from 0 to 20.

In another aspect the disclosure provides a compound of formula XI:

(XI)

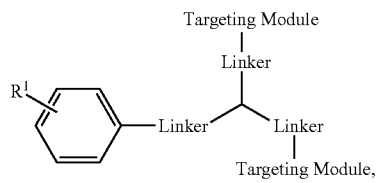

or a pharmaceutically acceptable salt thereof, wherein:

each Linker is independently selected from —O—, —NH—, —S—, —(C$_1$-C$_{20}$)alkyl, —(CH$_2$CH$_2$O)$_m$—, NHC(=O) (CH$_2$)$_n$, —C(=O)(CH$_2$)$_q$,

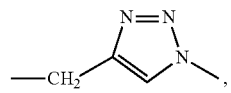

and combinations thereof, wherein m, n, and q are each independently an integer from 0 to 20; R$^1$ is independently

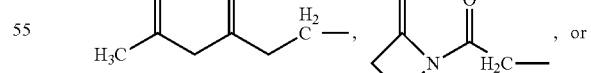

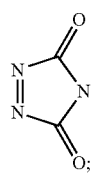

and

Targeting Module is a therapeutic compound.

In another aspect the disclosure provides a compound of formula XI, wherein each Linker is independently:
—NHC(=O)(CH$_2$)$_3$C(=O)NH—,
—NHC(=O)(CH$_2$)$_3$C(=O)NH(CH$_2$)$_3$—,
—NHC(=O)(CH$_2$)$_3$C(=O)NH(CH$_2$)$_2$(OCH$_2$CH$_2$)$_2$
—(CH$_2$)$_3$NHC(=O)(CH$_2$)$_3$C(=O)NH—,
—O(CH$_2$CH$_2$O)$_3$(CH$_2$)$_2$NHC(=O)(CH$_2$)$_3$C(=O)NH—,

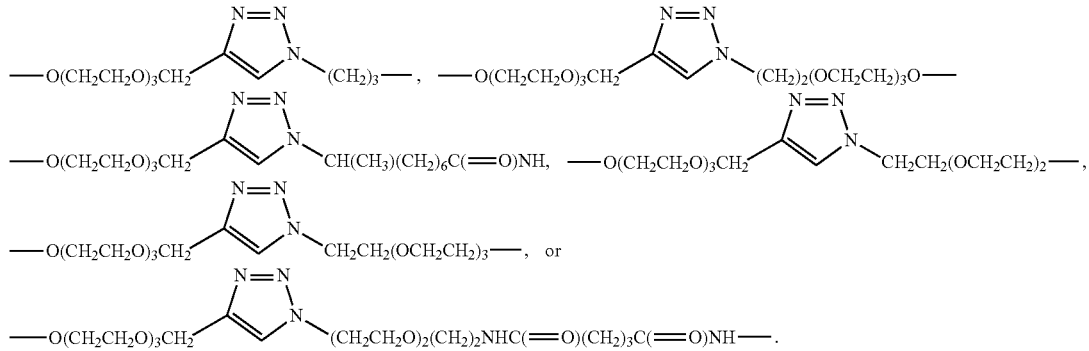

In another aspect the disclosure provides methods of extending the half life of a therapeutic drug in a patient in need thereof, the method comprising the step of administering a compound of formula I to the patient in need thereof.

In another aspect the disclosure provides methods of inhibiting HIV-1 infection in a patient in need thereof, the method comprising the step of administering a compound of formula II:

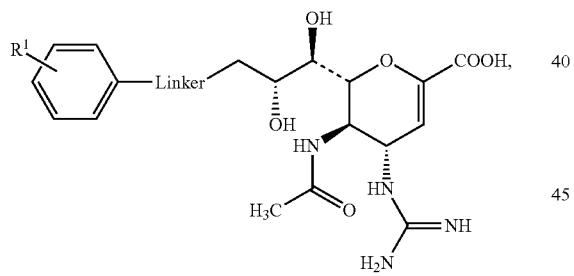

(II)

formula III or formula III'

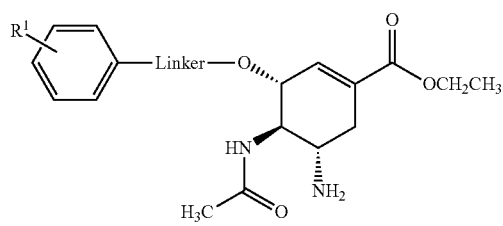

(III)

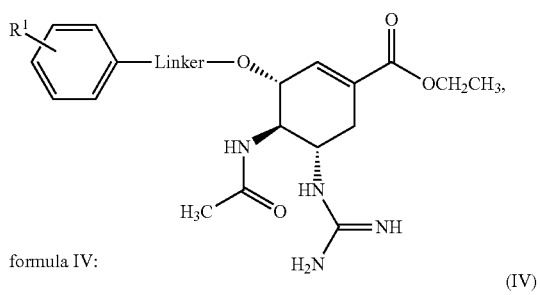

formula IV:

(III')

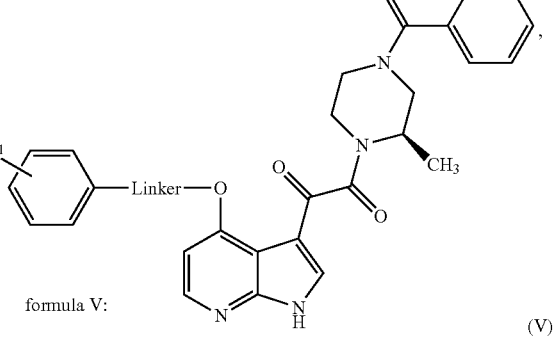

formula V:

(IV)

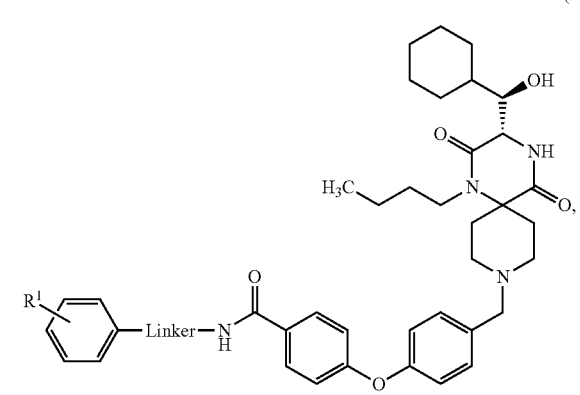

(V)

-continued formula VI:

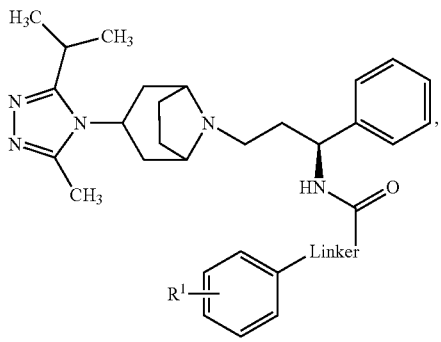

formula VII:

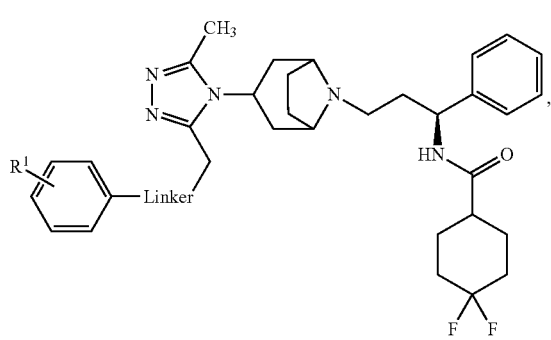

formula VIII:

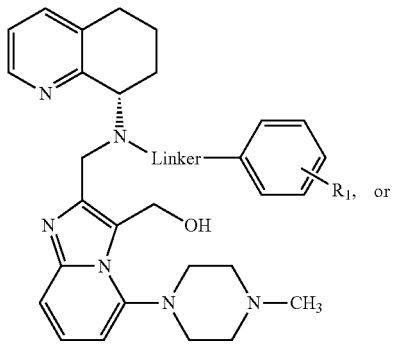

formula IX:

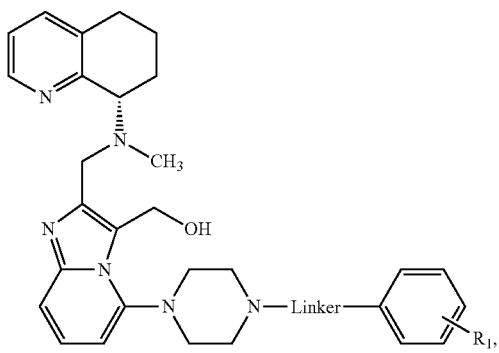

formula X or X':

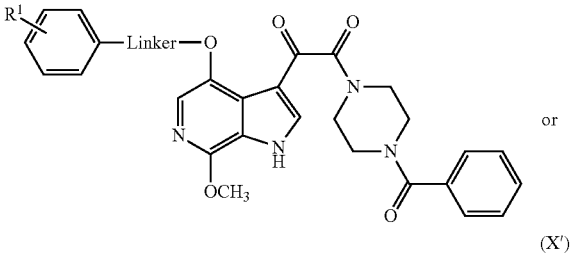

or

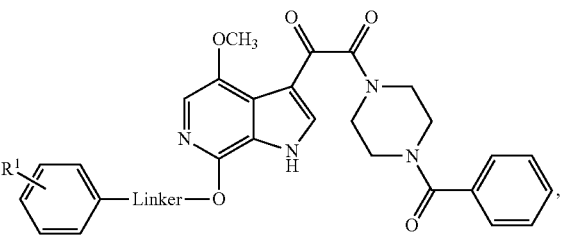

or a combination thereof, or a pharmaceutically acceptable salt thereof, wherein:
each Linker is independently selected from —O—, —NH—, —S—, —($C_1$-$C_{20}$)alkyl, —($CH_2CH_2O)_m$—, —NHC(=O)($CH_2)_n$, —C(=O)($CH_2)_q$,

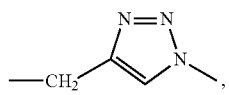

and combinations thereof, wherein m, n, and q are each independently an integer from 0 to 20; and
each $R^1$ is independently

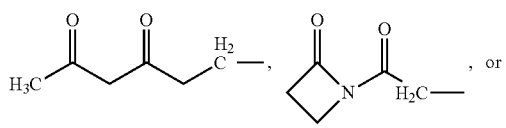

, or

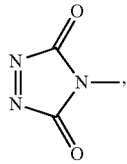

to a patient in need of such treatment.

In another aspect the disclosure provides methods of inhibiting HIV-1 infection in a patient in need thereof, the method comprising the step of administering a compound of formula II, III, III', IV, V, VI, VII, VIII, IX, X, or XI to a patient in need of such treatment, wherein HIV-1 infection is inhibited by blocking the CCR5 and/or CXCR4 receptors.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the target antigen is a tumor antigen, a self antigen, a toxin, a cancer antigen, a bacterial antigen, a viral antigen, or an integrin.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the target antigen is a tumor antigen, a self antigen, a toxin, a cancer antigen, a bacterial antigen, a viral antigen, or an integrin, wherein the integrin is $\alpha v \beta 3$ or $\alpha v \beta 5$.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the target antigen is a tumor antigen, a self antigen, a toxin, a cancer antigen, a bacterial antigen, a viral antigen, or an integrin, wherein the cancer is melanoma, colon cancer, glioma, ovarian cancer, cervical cancer, breast cancer, prostate cancer, lung cancer, a hematopoietic cancer, or head and neck cancer.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the carrier protein is selected from KLH, BSA and ovalbumin.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the subject is a human.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the target antigen is a tumor antigen, a self antigen, a toxin, a cancer antigen, a bacterial antigen, a viral antigen, or an integrin, wherein the target antigen is CCR5.

In another aspect the disclosure provides methods of generating covalent polyclonal antibodies, the method comprising the steps of preimmunizing a subject with an immunizing effective amount of a carrier protein-hapten complex; and administering a targeting compound to the subject, thereby generating a covalent polyclonal antibody response to a target antigen, wherein the target antigen is a tumor antigen, a self antigen, a toxin, a cancer antigen, a bacterial antigen, a viral antigen, or an integrin, wherein the target antigen is CCR5, wherein the CCR5 targeting compound has any one of formulae I-IX.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the targeting compound has any one of formulae I-IX.

In another aspect the disclosure provides an enriched population of covalent polyclonal antibodies.

In another aspect the disclosure provides a method of treating or preventing a disease or condition in a subject wherein the disease or condition involves cells, tissue or fluid that expresses a target molecule comprising: preimmunizing a subject with an immunizing effective amount of a carrier protein-hapten complex; and administering a targeting compound to the subject, thereby inducing a covalent polyclonal antibody response in the subject and treating or preventing the disease or condition.

In another aspect the disclosure provides methods of treating or preventing a disease or condition in a subject wherein the disease or condition involves cells, tissue or fluid that expresses a target molecule comprising: preimmunizing a subject with an immunizing effective amount of a carrier protein-hapten complex; and administering a targeting compound to the subject, thereby inducing a covalent polyclonal antibody response in the subject and treating or preventing the disease or condition, wherein the disease or condition is an infection and the target molecule is expressed by a microbial agent or virus.

In another aspect the disclosure provides methods of treating or preventing a disease or condition in a subject wherein the disease or condition involves cells, tissue or fluid that expresses a target molecule, the method comprising the step of administering to a subject in need thereof, an antibody and a targeting compound.

In another aspect the disclosure provides methods of treating or preventing a disease or condition in a subject wherein the disease or condition involves cells, tissue or fluid that expresses a target molecule, the method comprising the step of administering to a subject in need thereof, an antibody and a targeting compound, wherein the compound is administered in vivo.

In another aspect the disclosure provides methods of treating or preventing a disease or condition in a subject wherein the disease or condition involves cells, tissue or fluid that expresses a target molecule, the method comprising the step of administering to a subject in need thereof, an antibody and a targeting compound, wherein the compound is administered topically.

In another aspect the disclosure provides methods of treating or preventing a disease or condition in a subject wherein the disease or condition involves cells, tissue or fluid that expresses a target molecule, the method comprising the step of administering to a subject in need thereof, an antibody and a targeting compound, wherein the compound is administered orally.

In another aspect the disclosure provides methods of generating covalent polyclonal antibodies, the method comprising the steps of: preimmunizing a subject with an immunizing effective amount of a carrier protein-hapten complex; and administering a targeting compound to the subject, thereby generating a covalent polyclonal antibody response to a target antigen, wherein the target antigen is a protein or a carbohydrate.

In another aspect the disclosure provides a monoclonal antibody isolated from the population of covalent polyclonal antibodies.

In another aspect the disclosure provides methods of treating or preventing a disease or condition in a subject wherein the disease or condition involves cells, tissue or fluid that expresses a target molecule comprising: preimmunizing a subject with an immunizing effective amount of a carrier protein-hapten complex; and administering a targeting compound to the subject, thereby inducing a covalent polyclonal antibody response in the subject and treating or preventing the disease or condition, wherein the disease or condition is an infection and the target molecule is expressed by a microbial agent or virus, wherein the target molecule is expressed by HIV or influenza.

In another aspect the disclosure provides chemically programmed vaccines and antibodies for use in therapy and prevention of flu. Coupling of a reactive linker to influenza neuraminidase inhibitors such as Tamiflu and Relenza provide for the chemical programming of antibody 38C2 and polyclonal antibodies induced by immunization to bind to and neutralize influenza viruses. An instant immunity vaccine should be an attractive solution to sporadic flu outbreaks since administration of the targeting compound may provide immunity for a month without readministration. Further, stock-piling of humanize 38C2 or human polyclonal antibodies with the same reactivity could be readily used for passive transfer. Small cocktails of neuraminidase inhibitors could serve to block many flu strains. Compounds that bind each other, ideally conserved, epitopes on the flu virus could be used as novel targeting agents to direct instant immunity vaccines and antibodies.

The failings of classical vaccine strategies are perhaps most obvious in the long quest for an HIV-1 vaccine. More than 25 years have passed since the discovery of HIV and 17 years have passed since the discovery of the broadly neutralizing antibody b12, yet an effective HIV vaccine remains elusive. Only the most modest signs of success have recently been reported from a large vaccine trial in Thailand. Obviously, time-tested vaccine approaches have failed to work with HIV-1 and numerous novel approaches like DNA vaccination have failed as well. It is generally suggested that an effective HIV-1 vaccine should elicit potent T-cell mediated immunity and broadly neutralizing antibodies and numerous attempts to achieve this goal have failed. Experimental support for a role of neutralizing antibodies in an HIV-1 vaccine comes from studies involving passive transfer of neutralizing antibodies in animal challenge models. Several studies have shown that transfer of sufficient quantities of broadly neutralizing antibodies (bNAbs) can achieve sterilizing immunity against intravenous, vaginal, or rectal challenge in macaque models. Alternatively, the delivery of broadly neutralizing antibodies using gene-based approaches in animal models has also been shown to be effective in these models. Thus, if immunogens could be designed that elicit sufficient titers of bNAbs, an effective HIV-1 vaccine might be produced. In the many years since the discovery of b12, only 5 additional bNAbs have been described; 2G12, 2F5, 4E10 and recently PG9 and PG16. Thus the development of such responses in natural infections appears to be rare. Hope for an antibody based vaccine is further tempered by the fact that in the many years since the b12 epitope was defined as the CD4 binding site, no immunogen has been described that is capable of inducing this type of potent bNAb or in recapitulating the specificities of the remaining 5 bNAbs. This failure points to one of the key challenges of HIV-1 vaccine design, the design or development of immunogens that quantitatively elicit antibodies against neutralizing epitopes vs nonfunctional epitopes.

As noted above, one way around this daunting challenge is to deliver a cocktail of bNAbs using gene-based approaches like adeno-associated viruses. While this is an intriguing approach that deserves more attention, there are inherent risks and limitations to gene therapy in general and while space precludes discussion of the risks and limitations common to virtually all gene therapies, an approach that delivers a fixed cocktail of antibodies (if this is ever shown to be possible) would not be readily adaptive in the face of the emergence of a resistant virus. A system devoid of the general problems of gene therapy that would allow for the cocktail of bNAbs to be readily modified to counter emerging viruses might be ideal. A system that would allow for the absolute concentrations of the various antibodies to be independently adjusted or turned off in response to adverse activity would also be desirable.

Thus, in one aspect the disclosure provides chemically programmed vaccines that are based on in vivo programming of covalent polyclonal antibody responses with designed ligands or programming agents. This approach is based on chemically programmed monoclonal antibody technology now in multiple clinical trials. Reactive immunization protocols and immunogens may be optimized in animal models, including rabbit and macaque models. The disclosure also provides for the preparation of programming agents for HIV-1 co-receptor and virus targeting, which may be optimized for display on covalent binding antibodies, and studied in vivo as single agents and as combinations to determine the most promising approach to block HIV-1 transmission (e.g., CXCR4 and CCR5). Using optimized protocols and reagents, the efficacy of the disclosed chemically programmed vaccine approach may be evaluated on the protection of rhesus macaques from vaginal challenge with R5-SHIV$_{SF162P3}$. This approach is in contrast to standard vaccine development, which is based on attenuated viruses, protein immunization (recombinant or killed virus), or gene-based approaches. By coupling active immunization in the induction of covalent programmable antibody responses with designer ligand programming of the response, a robust, flexible and potent blockade of transmission is provided. This type of chemistry-driven approach may be applied to vaccinology to provide routes to vaccines to protect against diseases that have proven intractable to biology-driven vaccine approaches, in particular HIV-1. This approach is highly significant, providing both a novel and effective vaccine for HIV-1 and validating an approach that can be broadly applicable to viral disease prevention.

In order to address challenges that appear to be intractable using current vaccine strategies, the disclosure provides a strategy that uses the potential of a chemistry-driven approach to vaccinology in cancer. A chemically programmable vaccine strategy uses reactive immunization to induce a covalent-binding antibody response and is based on studies with monoclonal antibodies. The reactive immunization was developed for the generation of catalytic monoclonal antibodies. Reactive immunization differs from the usual immunization approaches in that reactive chemicals designed to elicit covalent antibodies are used as immunogens. Immunization with β-diketone immunogens allows for the reproducible induction of covalent antibodies that can be utilized to catalyze enamine- and iminium-based transformations like the Aldol reaction. A new class of therapeutic molecules was also developed by programming covalent monoclonal antibodies via their covalent reaction with designed ligands of a variety of specificities and that such chemically programmed antibodies possess potent biological activities in a variety of animal models of disease for example, the treatment of cancer and diabetes. While this approach is a form of monoclonal antibody therapy, covalent polyclonal responses may be efficiently induced and programmed in vivo to produce a therapeutic outcome. Induced covalent polyclonal responses in three strains of mice programmed by injection of a suitably designed programming compound provide treated animals with 'instant immunity' to their implanted tumors by quantitatively focusing the polyclonal response on the ligand-binding site of the self antigen integrin αvβ3. Classic antibody effector functions like antibody dependent cellular cytotoxicity (ADCC) are operative in this system supporting the idea that chemically programmed polyclonal antibodies function like natural antibodies.

Figure 11A:
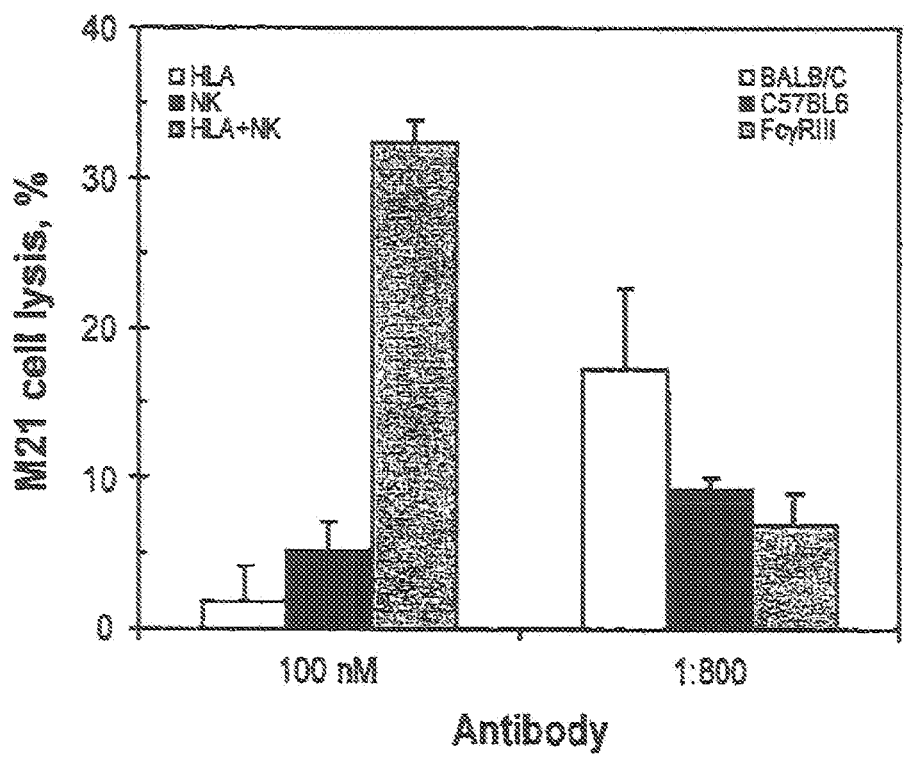
FIG. 11 illustrates NK cell-mediated ADCC activity of chemically programmed antibodies. (A) The capacity of anti-HLA mAb and SCS-873-programmed mouse sera to lyse radiolabeled M21 cells by ADCC was evaluated by a standard [$^5$Cr]-release assay as described in Methods. Nude spleen-isolated NK cells were used as effector cells! (B) The capacity of anti-HLA mAb to lyse radiolabeled M21 cells by ADCC in the presence of Nude, SCID, BALB/C, or C57BL6 spleen-isolated NK cells as effectors. The values shown are means of triplicate samples (±SD).
Figure 11B:
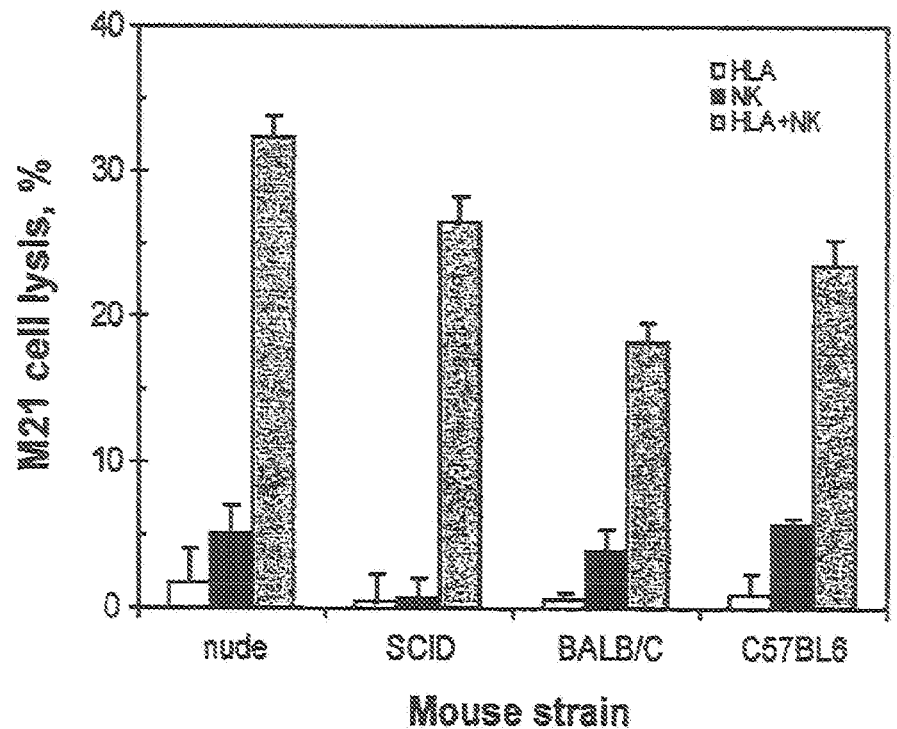
Figure 12A:
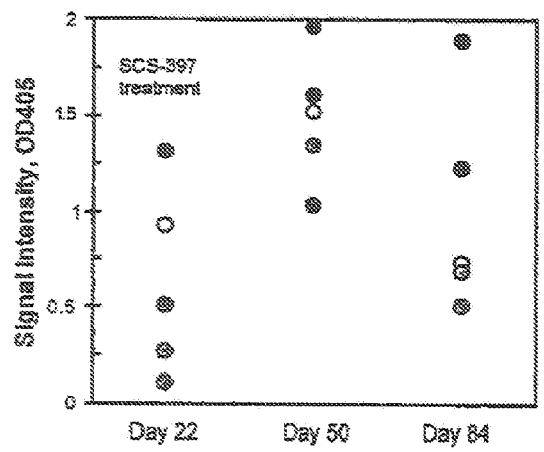
FIG. 12 illustrates JW-BSA-immunized BALB/C mice antibody titer prior and during CT26 tumor development. BALB/C mice were immunized with JW-KLH according to the published method with antigen boosting on days 15 and 43 (1). On day 65, mice were sorted to form groups with matched anti-JW titer and were inoculated s.c. into right flanks with 0.1 mL ($2 \times 10^5$ cells/mouse) of CT26 cell suspension in PBS. Individual JW-antiserum from JW-KLH-immunized mice was collected on days 22, 50, and 85 and used for in vitro assays. Antibody concentration was determined as previously described in material and methods. Antibody titer is shown as signal intensity at 405 nm for each mouse in the group (represented as different color dot). Panels shown titers for the different mice groups treated with SCS-397 (A), cRGD (B), SCS-873 (C) and cRGD-dk (D).
Figure 12B:
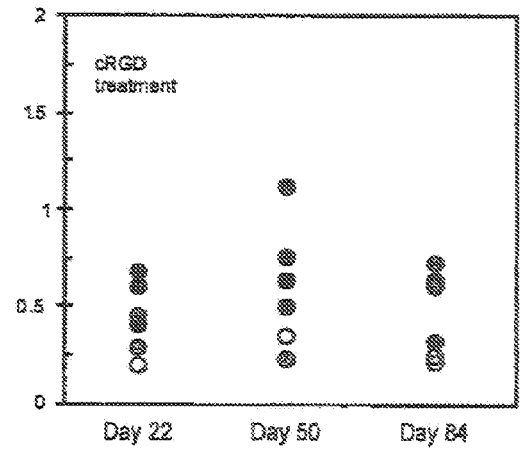
Figure 12C:
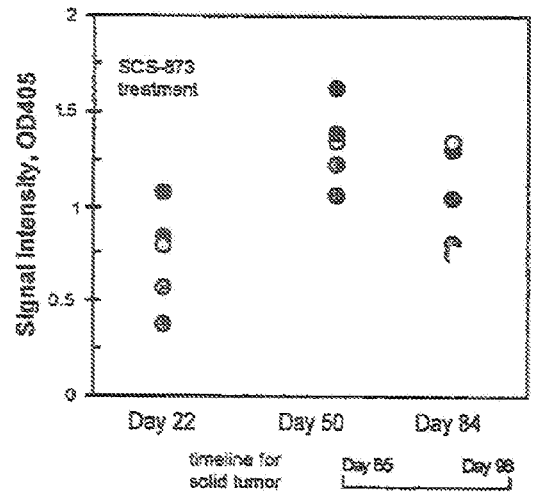
Figure 12D:
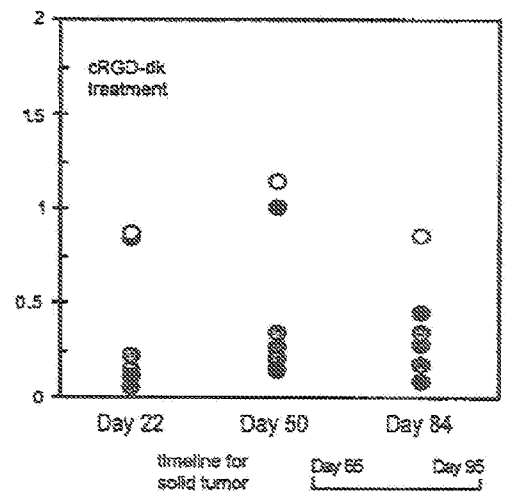
Figure 13A:
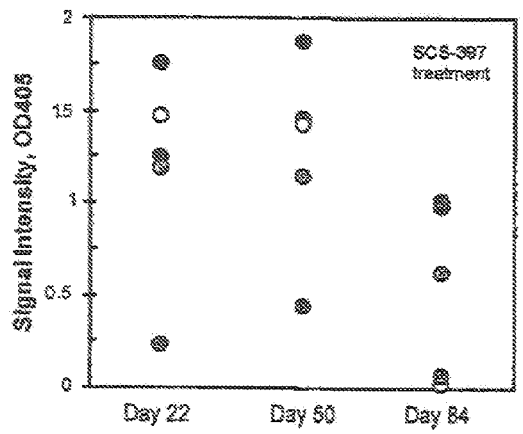
FIG. 13 illustrates JW-BSA-immunized C57BL6 and C57BL6/FcγRIII knockout mice antibody titer prior and during B16 tumor development. C57BL6 and C57BL6/FcγRIII knockout mice were immunized with JW-KLH according to the published method with antigen boosting on days 15 and 43 (1). On day 65, mice were sorted to form groups with matched anti-JW titer and were inoculated s.c. into right flanks with 0.1 mL ($2 \times 10^5$ cells/mouse) of B16 cell suspension in PBS. Individual JW-antiserum from JW-KLH-immunized mice was collected on days 22, 50, and 85 and used for in vitro assays. Antibody concentration was determined as previously described in material and methods. Antibody titer is shown as signal intensity at 405 nm for each mouse in the group (represented as different color dot). Panels shown titers for C57BL6 JW-KLH-immunized mice treated with SCS-397 (A), or SCS-873 (C) and C57BL6/FcγRIII knockout JW-KLH-immunized mice treated with SCS-397 (C) or SCS-873 (D).
Figure 13B:
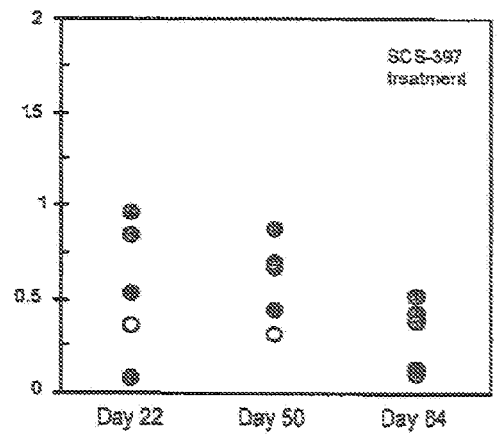
Figure 13C:
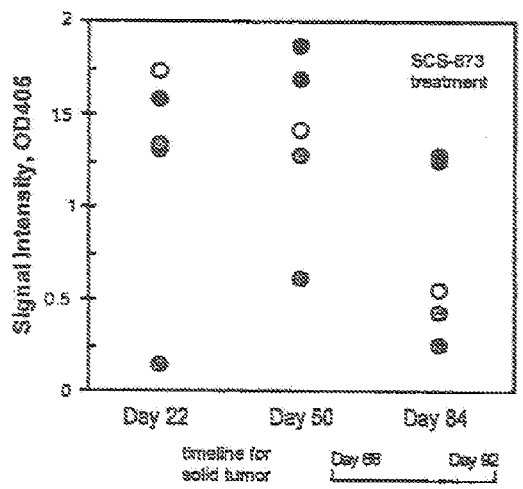
Figure 13D:
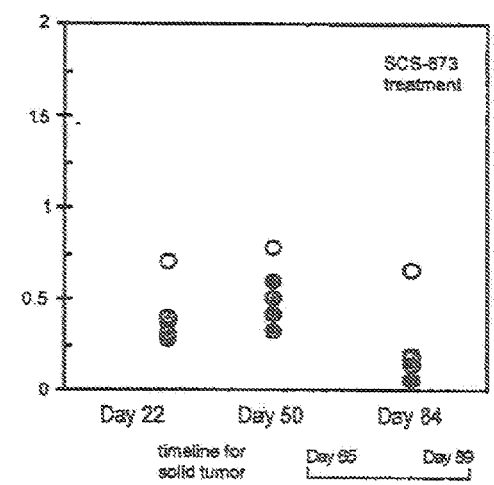
Figure 14:
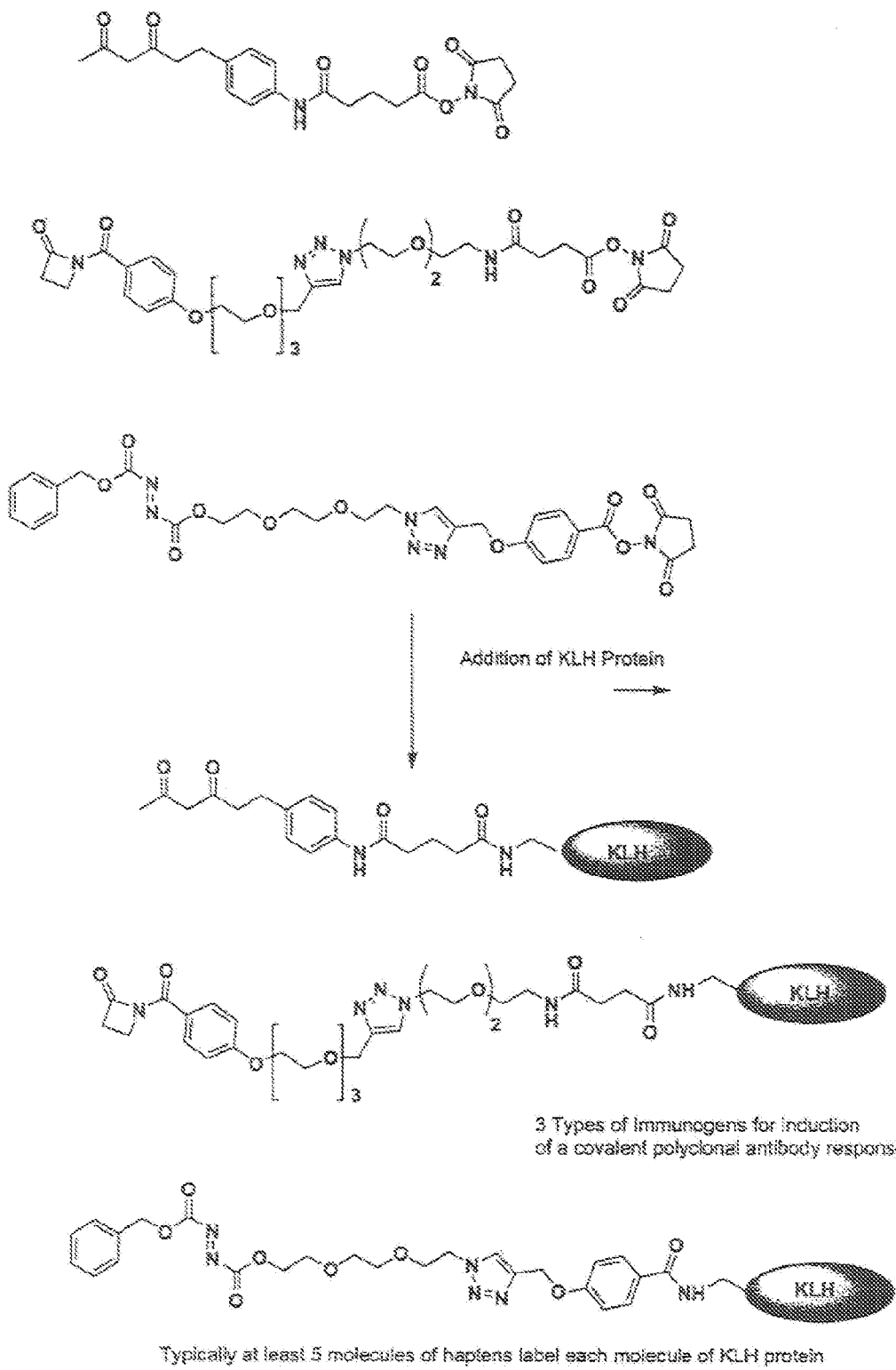
FIG. 14 illustrates haptens for labeling KLH for immunization. The illustrative haptens, NHS esters, are mixed with protein in aqueous solution to label them through amide bond formation with amine groups.
Figure 15:
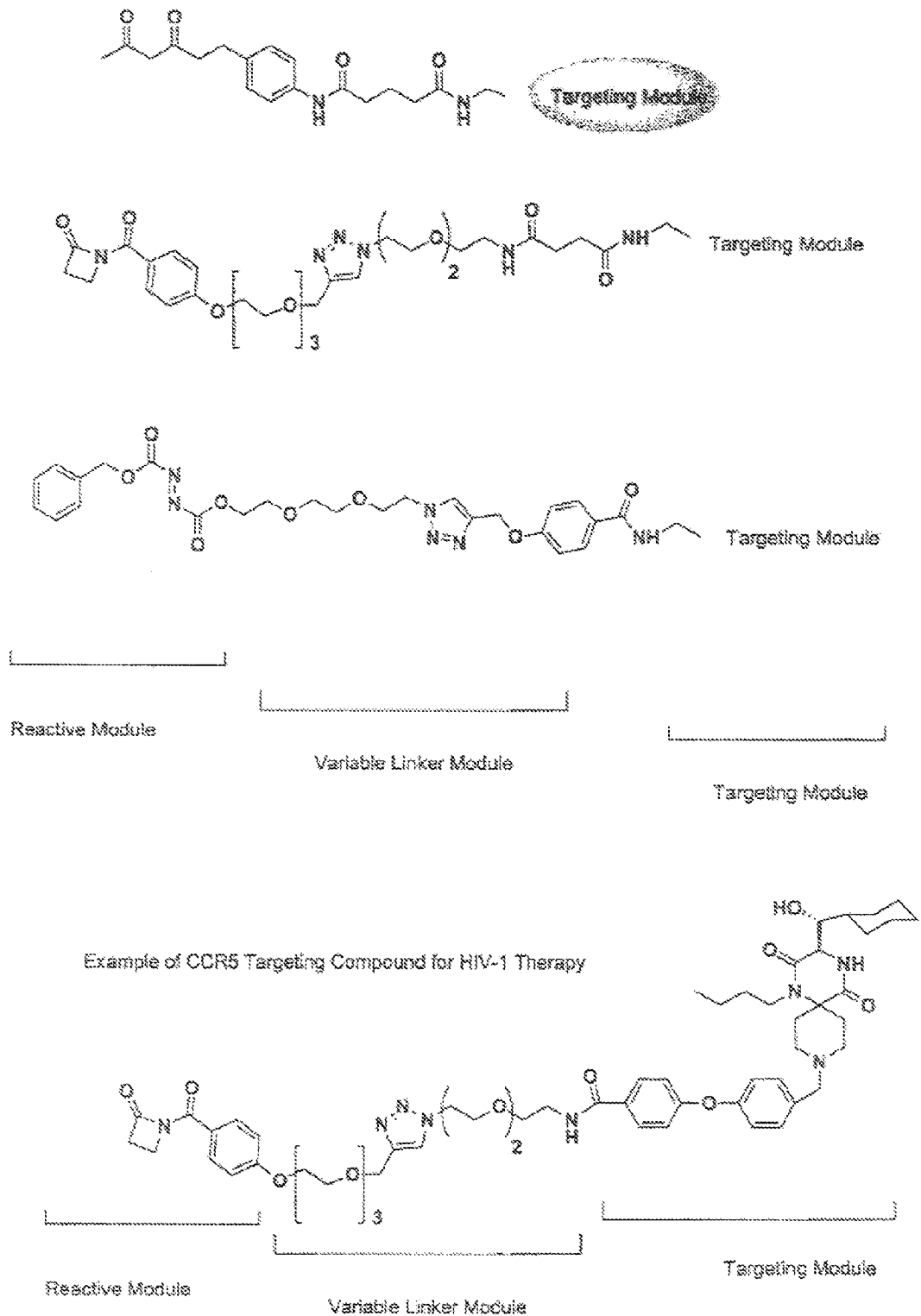
FIG. 15 illustrates haptens of FIG. 8, including the Reactive Module, the Variable Linker Module and the Targeting Module as described herein. An illustrative CCR5 Targeting compound for HIV-1 therapy is also shown.

The disclosure provides a robust and broadly protective chemically programmed vaccine that effectively blocks HIV-1 transmission in a primate model. This unconventional approach has never been explored in anti-viral vaccine development or in primates and addresses key problems in HIV-1 vaccine development. The disclosed chemically programmed vaccine approach against HIV-1 is illustrated in FIG. 11.

Covalent polyclonal antibodies can be induced in primates using reactive immunization and these polyclonal responses can be programmed in vivo following intravenous administration of specific virus-targeting and/or co-receptor targeting ligands or programming agents. A bispecific-programming agent is illustrated in FIG. 11, which possesses virus binding and co-receptor binding arms. The programmed polyclonal response may be quantitatively directed to neutralizing epitopes on the virus and a blocking epitope on the HIV-1 co-receptor CCR5 thereby neutralizing virus and blocking viral entry when the animals are challenged with virus. Alternatively, a small cocktail of programming agents may be administered to block a collection of viral subtypes and co-receptor epitopes. Since the polyclonal response is programmed with small molecules it is expected to persist for several weeks in treated animals and to decline with a half-life typical of a standard polyclonal antibody response. Persistent immunity to HIV-1 would require dosing of programming agents at regular, perhaps monthly intervals in contrast to typical small molecule drugs that might require multiple doses per day. It is important to note that doses of less than 100 micrograms/kg of programming agent are sufficient to program 10 mg/kg of antibody in this approach. Changing the doses of the programming agents may modulate the relative levels of polyclonal antibodies against any of the targeted epitopes. Thus, the magnitude of the response and its relative distribution on targets may be controlled and any unexpected adverse effects would diminish with time if programming agents are withheld.

More and varied programming molecules that fully address the genetic variability of the virus, reducing the potential for viral escape while broadening prophylactic efficacy may also be produced. Furthermore, universal programmable covalent polyclonal antibodies may be readily available for passive transfer to non-immunized individuals who could be provided with 'instant immunity' following administration of a designed ligand. This approach is significantly more cost effective than passive transfer of bNAbs, safer than gene therapy, and more flexible than either of these approaches. This approach is in contrast to the standard paradigms of vaccine development based on attenuated viruses, protein immunization (recombinant or killed virus), or gene-based approaches. By coupling active immunization in the induction of covalent programmable antibody responses with designer ligand programming of the response, a robust, flexible and potent blockade of transmission may be created. This type of chemistry-driven approach to vaccinology provides routes to vaccines to protect against diseases that have proven intractable to biology-driven vaccine approaches, in particular HIV-1. In the future it might be possible to program polyclonal antibody responses with oral doses of small molecules. This approach may be highly significant, providing both a novel and effective vaccine for HIV-1 and validating an approach that can be broadly applicable to viral disease prevention.

There are two key components to a chemically programmed vaccine strategy; reactive immunogens/immunization and programming agents. In order to ensure success, each of these components were studied in detail and alternative reactive immunogens as well as programming agents were compared to ensure that the best components are used. The potential of chemically programmed vaccine approach to provide protection in vivo using the R5-SHIV$_{SF162P3}$ macaque model may be used as this model has been extensively studied for the potential of bNAb b12 to block transmission and to determine the mechanisms key to producing sterilizing immunity with monoclonal antibodies.

Reactive Immunogens and Reactive Immunization

The initial studies of chemically programmed vaccines in rodent models of cancer, a diketone hapten was coupled to keyhole limpet hemocyanin (KLH) for induction of covalent polyclonal antibodies that were then programmed in vivo. From the studies with chemically programmed monoclonal antibodies prepared by immunization with the same hapten, it was found that these antibodies react covalently with diketones but also with β-lactams. In the later case an irreversible amide linkage results. This type of linkage is used in four different chemically programmed monoclonal antibodies now in clinical trials because it provides for longer pharmacokinetics. The potential programming of covalent antibodies in vivo using β-lactams or their potential as reactive immunogens for this approach has not yet been studied. A third reactive immunogen is cyclic diazodicarbox-amides. This functionality reacts with the phenolic group of tyrosine in an ene-like reaction yielding a stable irreversible covalent linkage (see, Scheme 1).

SCHEME 1 reactive diketone reactive β-lactam reactive cyclic diazodicarboxamide

A programming agent (PA) contains three parts: 1) targeting module (TM) that binds the desired target, 2) a reactive component that reacts with induced covalent binding antibodies to form a stable covalent linkage upon intravenous administration in vivo, and 3) a linker molecule that links the targeting module with the reactive component. Two CCR5 (Aplaviroc, Maraviroc), a CXCR4 (GSK812397), and several HIV-1 envelope targeting molecules (BMS; one example shown) were identified, wherein there is sufficient structure activity relationships published to append them on to a reactive moiety via a linker molecule. To optimize presentation and activity of the PA, each compound with linkers of different lengths may be prepared (see, Scheme 2).

SCHEME 2

(CCR5)

Aplaviroc based TM (CCR5)

Maraviroc based TMs (CXCR4)

GSK812397 based TMs

-continued
(gp120/CD4)
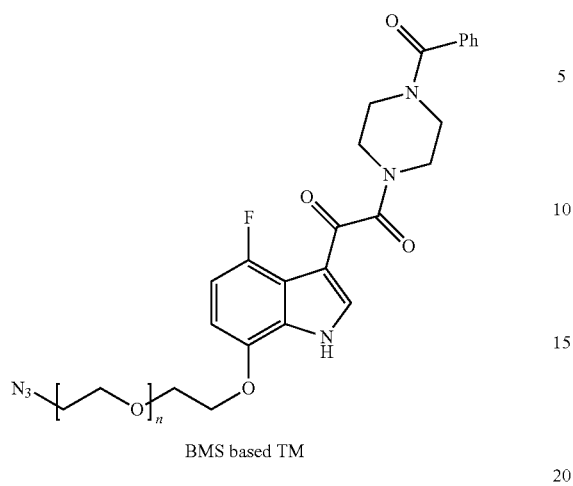
BMS based TM
Co-Receptor Targeting
The synthesis of an Aplaviroc-based programming agent may be based on a proline catalyzed Aldol reaction (see, Schemes 3 and 4; only targeting module-linker shown).
SCHEME 3

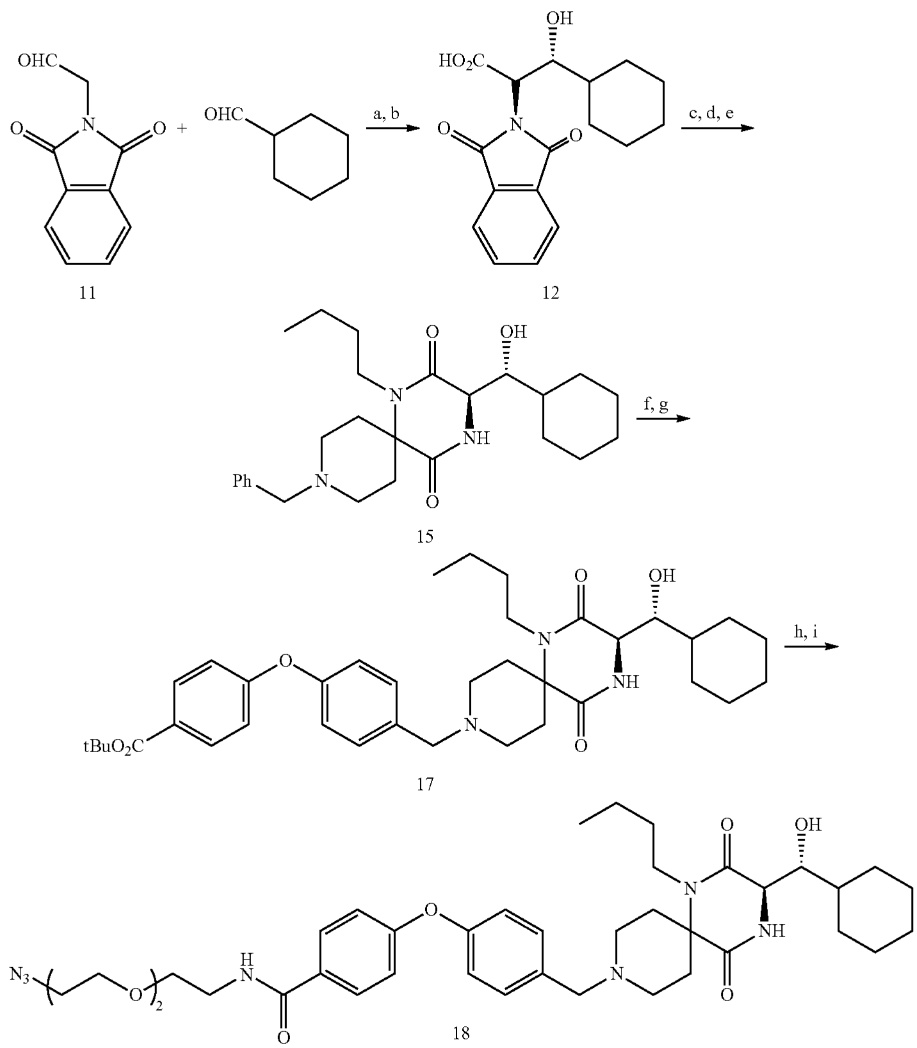

-continued
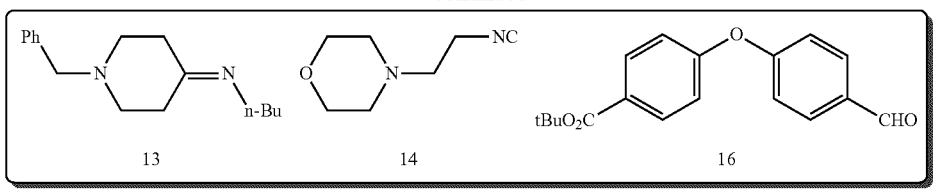
(a) D-Pro, NMP;
(b) NaClO$_2$;
(c) 13, 14, MeOH;
(d) H$_2$NNH$_2$—H$_2$O, 60° C.;
(e) AcOH, toluene, 70° C.;
(f) Pd(OH)$_2$/C, H$_2$;
(g) 16, NaBH(OAc)$_3$;
(h) 4N HCl/dioxane;
(i) BOP, 2-(2-(2-azidoethoxy)ethoxy)ethanamine
SCHEME 4
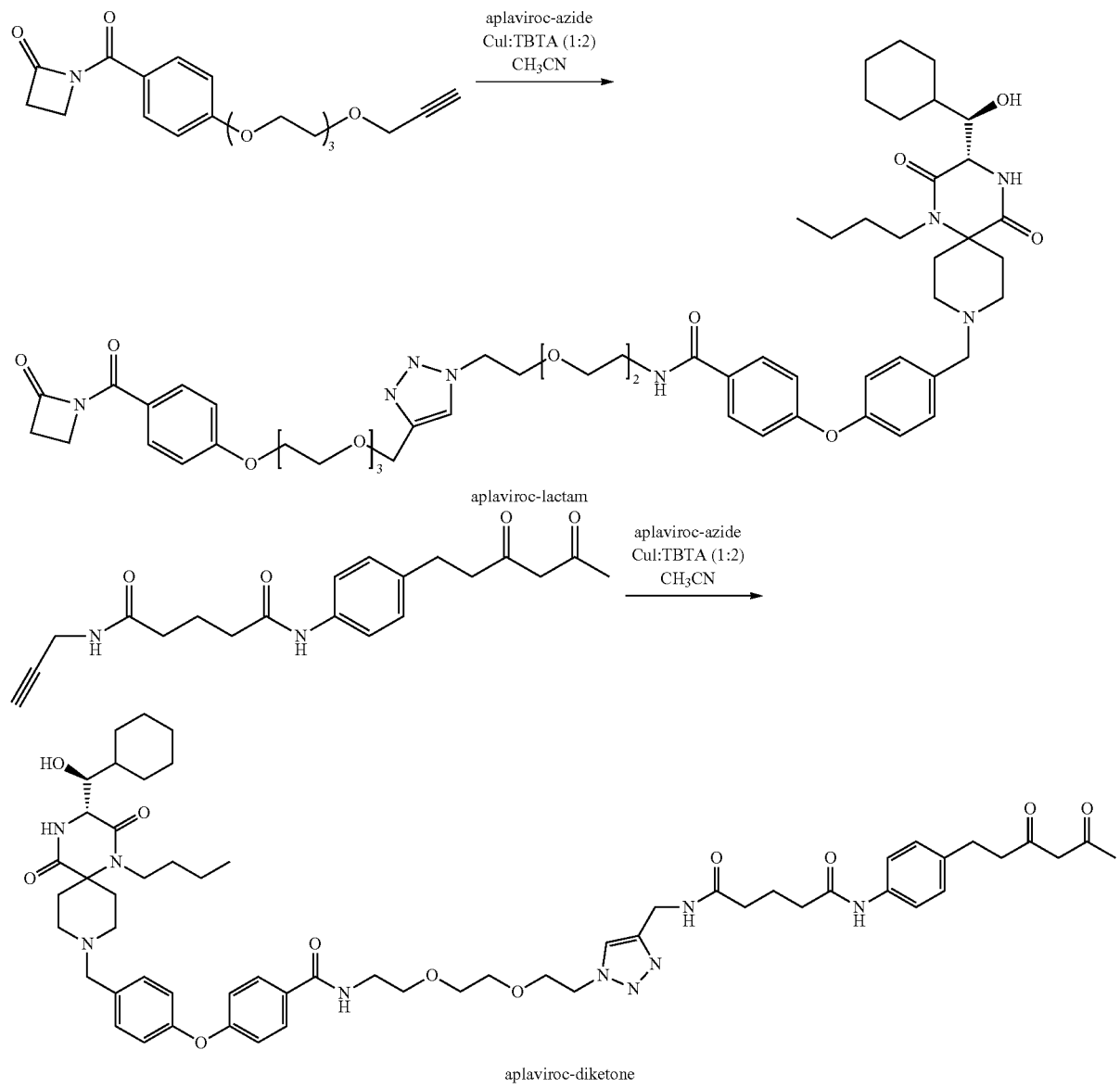

Figure 18:
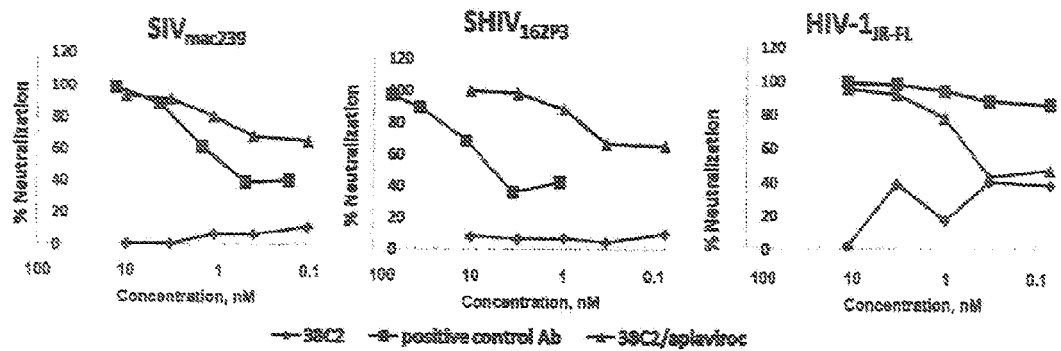
FIG. 18 illustrates virus neutralization via chemically programmed monoclonal 38C2 and Aplaviroc-based Programming Agent. Positive controls: bNAb b12 in SHIV and HIV-1 assay; CD4-Ig in SIV assay.

The potential to program monoclonal antibody 38C2 and to neutralize HIV-1, SW, SHIV was studied using the Aplaviroc-based programming agents. Its specific binding to human and macaque PBMCs and engineered cell lines confirmed CCR5-specific binding (see, FIG. 18).

This data suggests that both human and macaque CCR5 can be potently blocked using a novel chemically programmed antibody thereby abrogating viral entry. Dramatic increases in potency of the TM may be observed through coupling to the antibody that is based on the bivalent display of the TM on the antibody. To further explore CCR5 blockade using this approach, Maraviroc based PA was prepared. Unlike Aplaviroc whose clinical development was halted due to metabolic toxicity; Maraviroc is an approved CCR5 inhibitor.

Maraviroc
CCR5

-continued

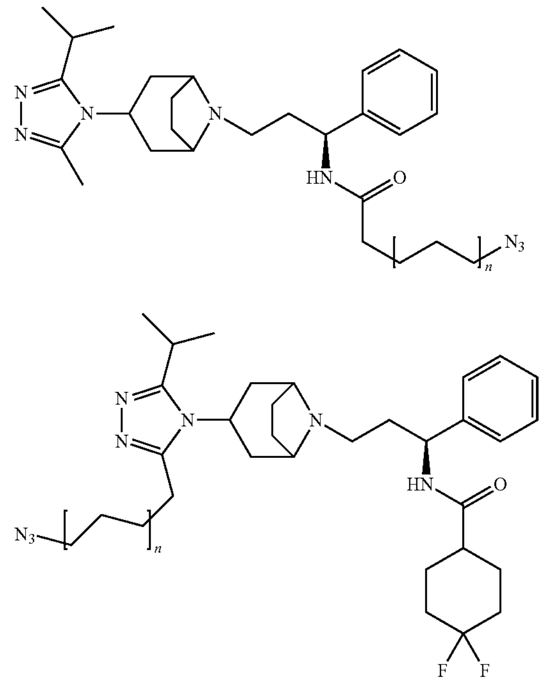

Maraviroc based Targeing Modules

We did not expect toxicity in our approach, which would apply the Aplaviroc based PA at a dose several orders of magnitude lower than when it is applied as a simple small molecule, we believe a Maraviroc based PA may be a significant alternative that may display enhanced breadth and potency and potentially better pharmacokinetics. A synthetic scheme for two differentially linked Maroviroc TMs is provided below, in which two types of azide containing Maraviroc TMs are possible (see, Scheme 5).

SCHEME 5

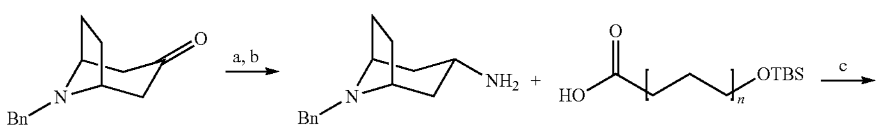

19

20

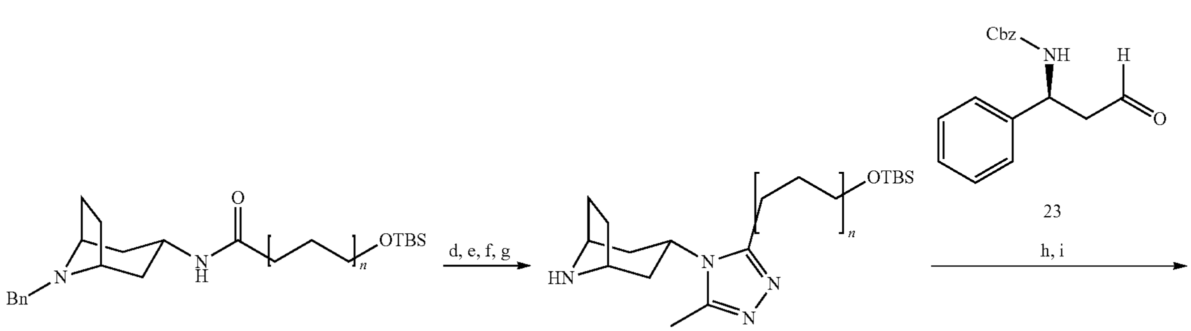

21

22

23

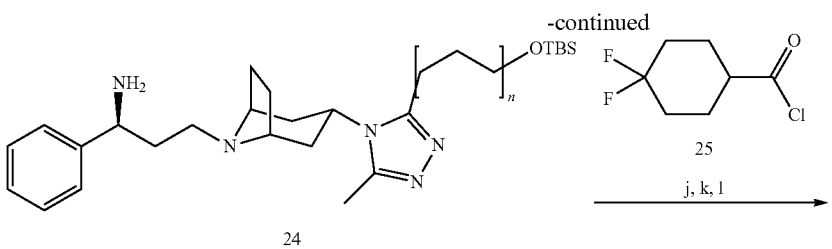

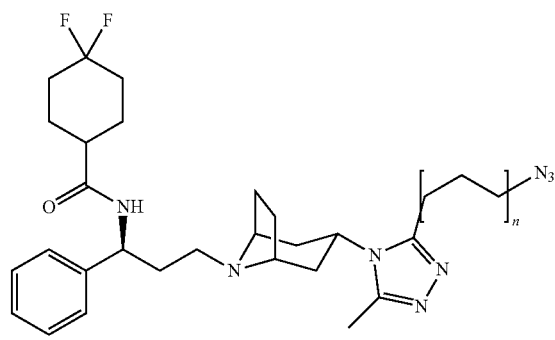

(a) NH₂OH—HCl, Py, EtOH;
(b) Na, n-pentanol, reflux;
(c) Et₃N, WSCDI, CH₂Cl₂;
(d) PCl₅, CH₂Cl₂, 0° C.;
(e) AcNHNH₂, tert-arryl alcohol;
(f) AcOH, tert-amyl alcohol;
(g) p-TsOH, H₂, 10% Pd/C;
(h) 23, p-TsOH, NaBH(OAc)₃, CH₂Cl₂, AcOH;
(i) Pd(OH)₂, H₂, MeOH;
(j) 25, Na₂CO₃, CH₂Cl₂;
(k) TBAF;
(l) i. TsCl, Et₃N;
  ii. NaN₃, DMF.

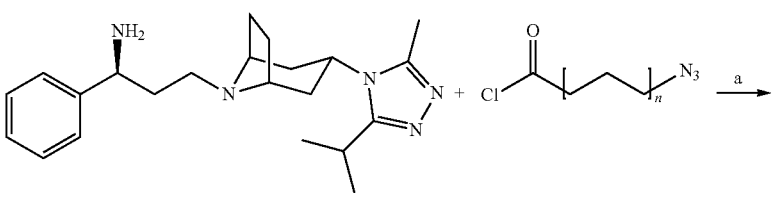

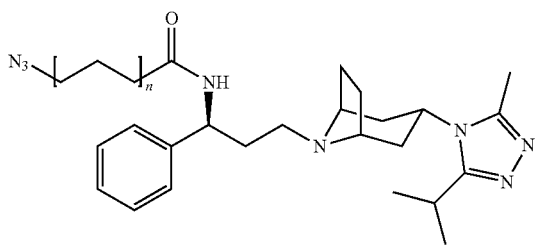

(a) Na₂CO₃, CH₂Cl₂

Readily available benzyl protected tropinone may be converted into the corresponding oxime followed by a sodium metal reduction that provides a separable mixture of endo- and exo-aminotropane 19. The separated exo-product 19 may be coupled with acid 20 bearing a variable length TBS protected alkyl alcohol tail to provide intermediate 21. Chlorination with PCl₅ in dichloromethane at 0° C., followed by addition of acetyl hydrazide in tert-amyl alcohol and cyclization in the presence of acetic acid in tert-amyl alcohol, and removal of benzyl protection by hydrogenation furnishes the triazole product 22. Protected amino aldehyde 23 may be prepared as previously described and used for the reductive amination with intermediate 22 followed by removal of Cbz with hydrogen in the presence of Pd(OH)₂ to give desired amine 24. Finally, coupling with the 4,4-difluorocyclohexanecarbonyl chloride 25, and interconversion of TBS protected hydroxyl functionality into azide completes the synthesis of Maraviroc based targeting module 26. Alternative linker attachment positions can be used by coupling the amine intermediate 27 accessible via an established synthetic route with a selection of variable length alkylazido acid chlorides 28, to give another Maraviroc based targeting module 29.

While evidence suggests that natural HIV-1 infection occurs primarily through the CCR5 receptor, later viral adaptation to the CXCR4 co-receptor is associated with disease progression and AIDS. The development of potent small molecule CXCR4 inhibitors provides a chemically programmed vaccine that blocks both CCR5 and CXCR4. For example, GSK812397 as shown below.

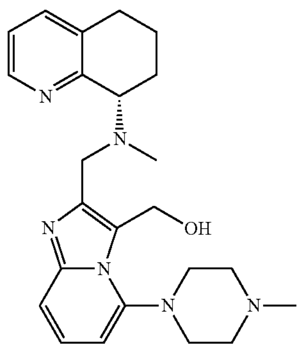

GSK812397
CXCR4

-continued

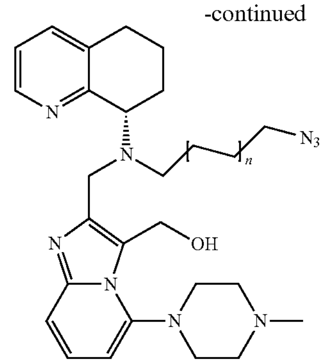

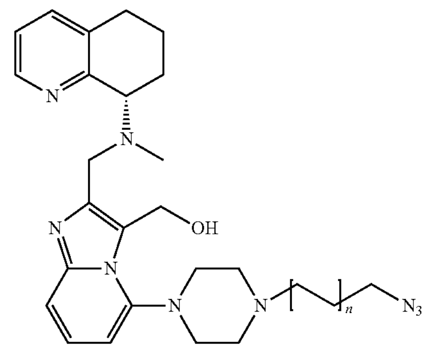

GSK based Targeing Modules

As shown above, two types of azide containing targeting modules based on the SAR data for CXCR4 antagonist GSK812397 may be used in order to identify the optimal linker attachment point. The synthetic plan is based on the process chemistry route to GSK812397 (see, Scheme 6).

SCHEME 6

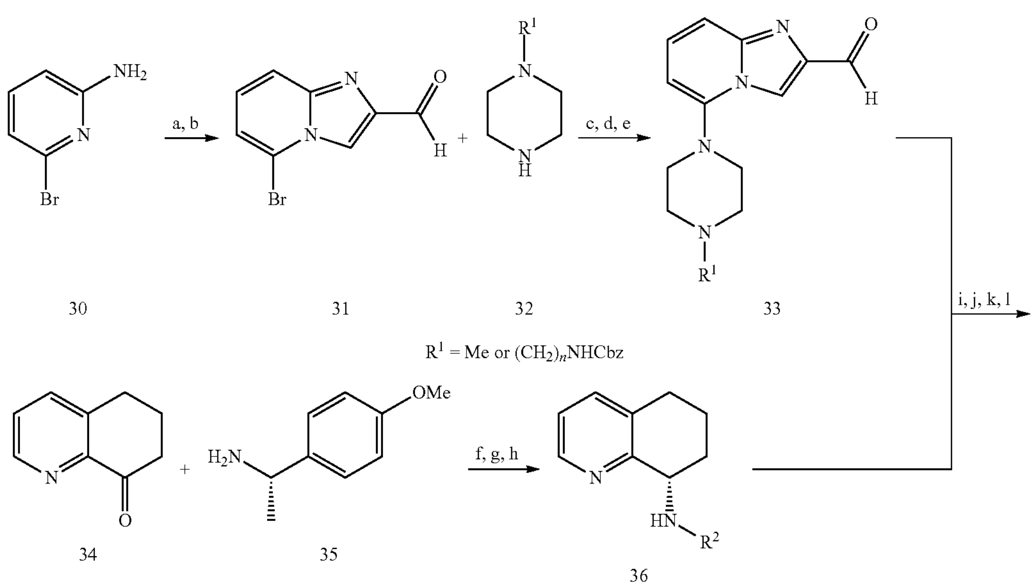

30 31 32 33

$R^1$ = Me or $(CH_2)_nNHCbz$ 34 35 36

$R^2$ = Me or $(CH_2)_nNHCbz$

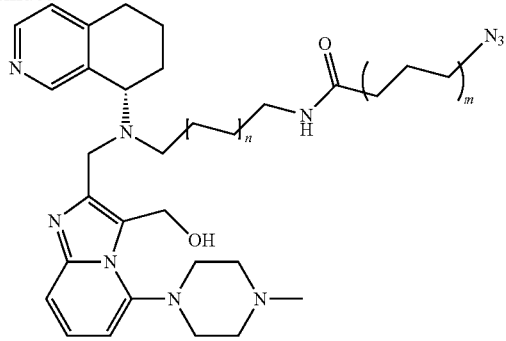

37 or

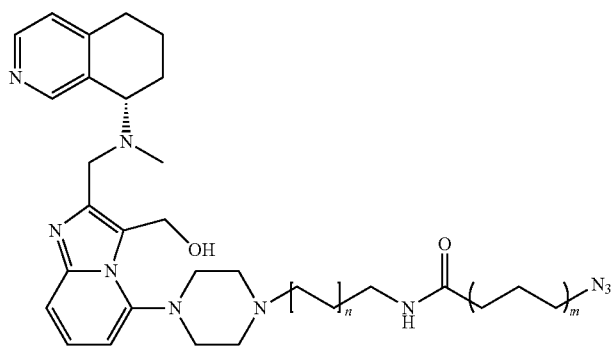

38

(a) 1,1,3-trichloroacetone, DME;
(b) aq HCl;
(c) n-BuLi, THF;
(d) aq HCl;
(e) aq NaOH;
(f) NaBH(OAc)$_3$, CH$_2$Cl$_2$;
(g) R$^2$CHO, NaBH(OAc)$_3$, CH$_2$Cl$_2$;
(h) TFA;
(i) NaBH(OAc)$_3$, Et$_3$N, CH$_2$Cl$_2$;
(j) CH$_2$O, H$_2$O;
(k) 10% Pd/C, H$_2$;
(l) NHS-azide linker, Et$_3$N.

Here, 2-amino-6-bromopyridine 30 is reacted 1,1,3-trichloroacetone in DME, followed by cyclization in the presence of HCl to provide 5-bromoimidazo[1,2-a]pyridine-2-carbaldehyde 31. Subsequent reaction of 31 with N-alkyl substituted piperazine 32 provides the key intermediate 33. The piperazine ring serves as one possible point of linker attachment. Cbz protected aminoalkyl chain may be used as one or the alkyl substituents R$^1$. Readily available tetrahydroquinolinone 34 may be subjected to reductive amination with chiral amine 35 to install the desired stereogenic center and isolate enantiomerically pure product by recrystallization. Subsequent reductive amination with alkyl aldehyde R$^2$CHO followed by hydrolysis of p-methoxybenzyl auxiliary in the presence of TFA provides the desired intermediate 36. The R$^2$ substituent may serve as a second linker attachment point. Reductive amination coupling or intermediates 36 and 33, followed by installation of hydroxymethyl functionalilty in the imidazole ring, removal of Cbz and coupling with NHS activated ester of azide containing carboxylic acid provides the desired CXCR4 targeting modules 37 and 38.
Viral Envelope Targeting Recently, BMS reported an advanced analog of their previously discovered inhibitor of gp120/CD4 complex formation; BMS-3788806. This new compound exhibits 60 µM activity, a promising pharmacokinetic profile, and is broadly neutralizing (including HIV-1 SF-162 on which our SHIV envelope is based). The SAR study conducted by BMS suggests that position C7 would be the best point for linker attachment. Our synthetic route is based on the literature synthesis of BMS-3788806 and starts with commercially available indole 39 (see, Scheme 7).

SCHEME 7

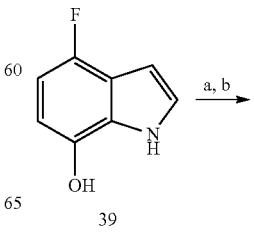

39

-continued

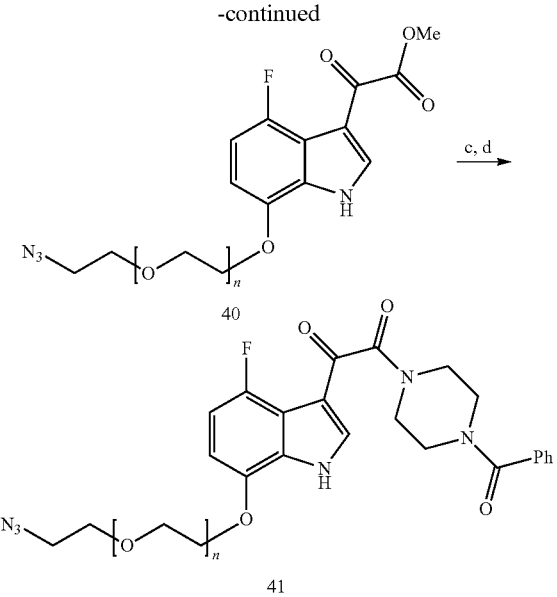

40

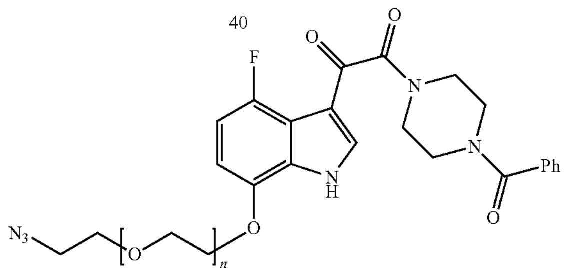

41

(a) $N_3$—$PEG_n$—OTs, $K_2CO_3$;
(b) EtO—C(O)—C(O)Cl, $AlCl_3$, $CH_2Cl_2$;
(c) $K_2CO_3$, MeOH;
(d) N-benzoylpiperazine, DEPBT, DIPEA, DMF Indole 39 is O-alkylated with azide-polyethyleneglycol linker of any desired length, followed by a reaction with methyl 2-chloro-2-oxoacetate in the presence of aluminum trichloride to provide intermediate 40. Reaction with potassium carbonate in methanol followed by a DEPBT mediated coupling with N-benzoylpiperazine provides the desired azide containing targeting module 41. Variants of BMS-3788806 are known in the literature and can be explored as alternative TMs.

The initial characterization of each TM involves its attachment to a linker and reactive module followed by reaction with monoclonal antibody 38C2 and polyclonal antibody prepared following immunization of animals with reactive immunogens. The antibodies that result display 1 TM per combining site or 2 per IgG molecule. As a means of increasing potency, each TM may be linked to a bifunctional linker wherein the resulting antibodies display 2 TMs per combining site or 4 per IgG. As a means of increasing breadth of coverage, TMs of different types (for example CCR5 TM and Envelope TM) may be combined using the bifunctional linkers (see, Scheme 8).

SCHEME 8

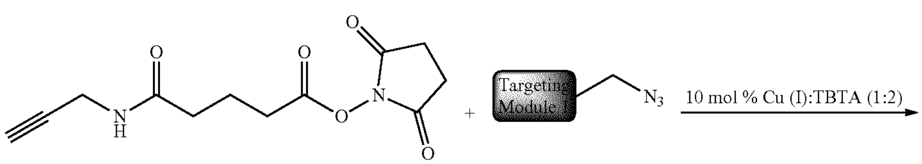

1

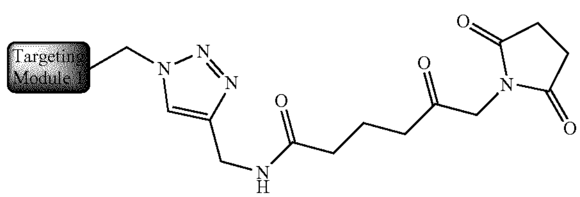

2

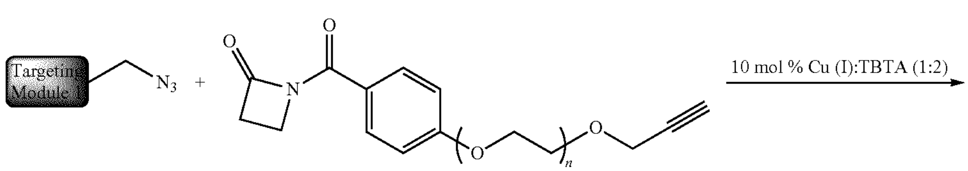

3

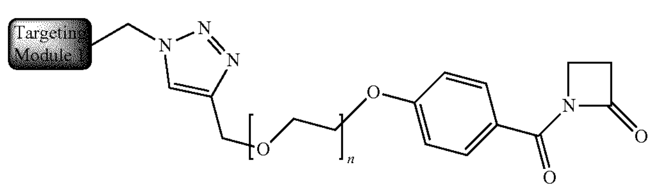

4

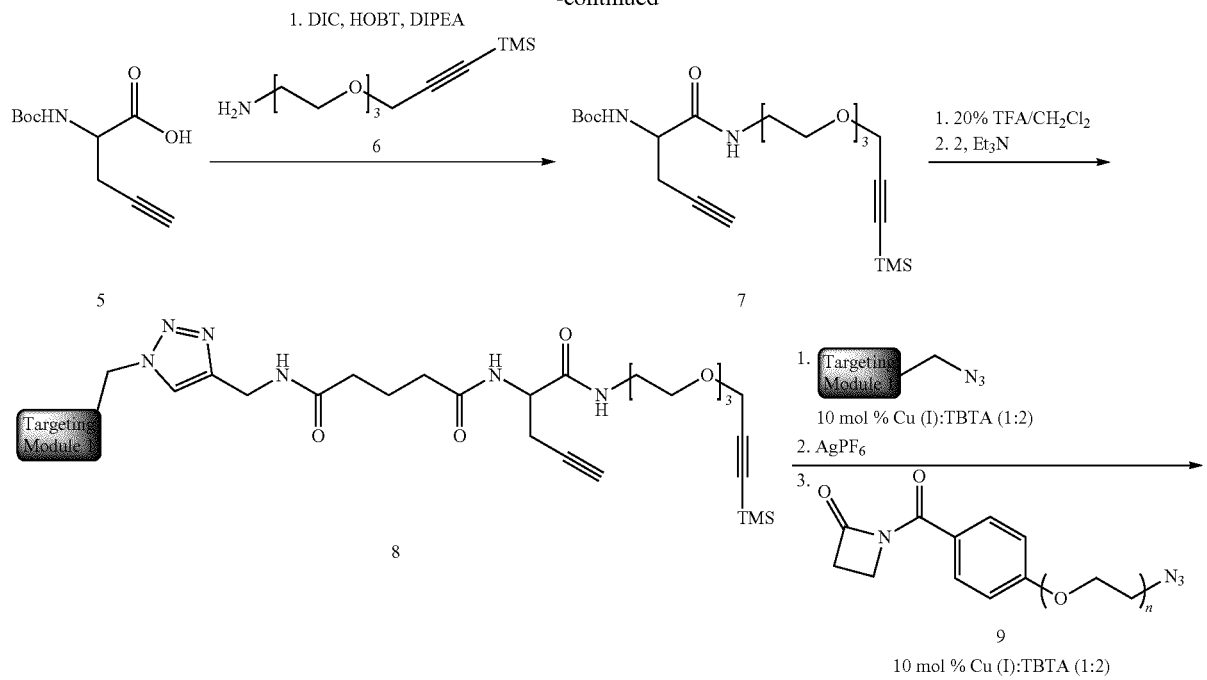
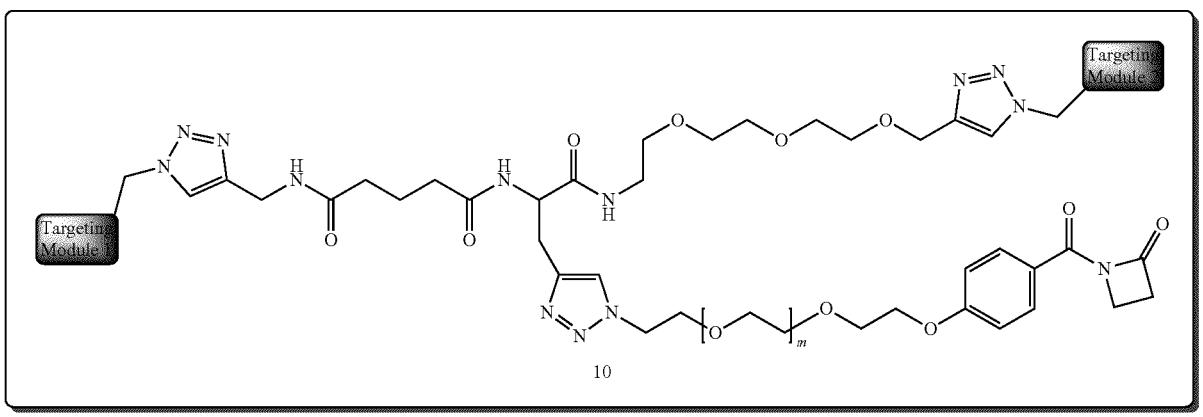

-continued 5 6 7 8 9 10

In these cases each antibody combining site displays the two different TMs. Programmed antibodies may be studied in antibody neutralization tests. Monofunctional targeting modules and building block intermediates may be readily accessible through copper catalyzed azide alkyne cycloaddition (click) reaction. Thus, azide containing targeting modules can be conjugated with either NHS-activated ester-alkyne 1 or β-lactam alkyne 3 to provide NHS-targeting module 2 and lactam equipped targeting module 4 respectively.

The bifunctional lactam equipped targeting modules can be synthesized starting from commercially available Boc protected propargyl glycine 5. DIC/HOBT mediated coupling of 5 with TMS protected alkynyl amine 6 provides corresponding Boc amide 7. Removal of the Boc using 20% trifluoroacetic acid in dichloromethane followed by reaction with NHS-targeting module 1 in the presence of triethylamine provides intermediate 8. TMS protection of the terminal alkyne presents a basis for preferential chemoselective click reaction of the unprotected alkyne with azide of the targeting module 2. Subsequent deprotection of the second alkyne in the presence of $AgPF_6$ and copper mediated coupling with β-lactam alkyne 9 completes the synthesis of bifunctional targeting module 10.

Gp120 Inhibitors Linked with Hapten Unit

Gp120 inhibitors linked with hapten unit of types 1 and 2 are shown below:

Type 1

-continued

Type 2

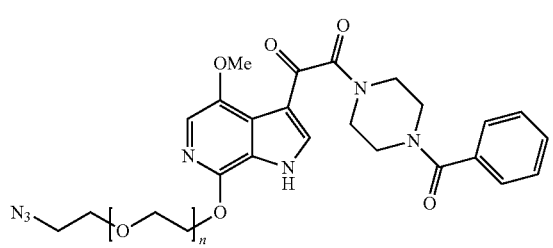
The gp120 inhibitors may be prepared as shown below in high yield with little to no chromatography (see, Scheme 9):
SCHEME 9

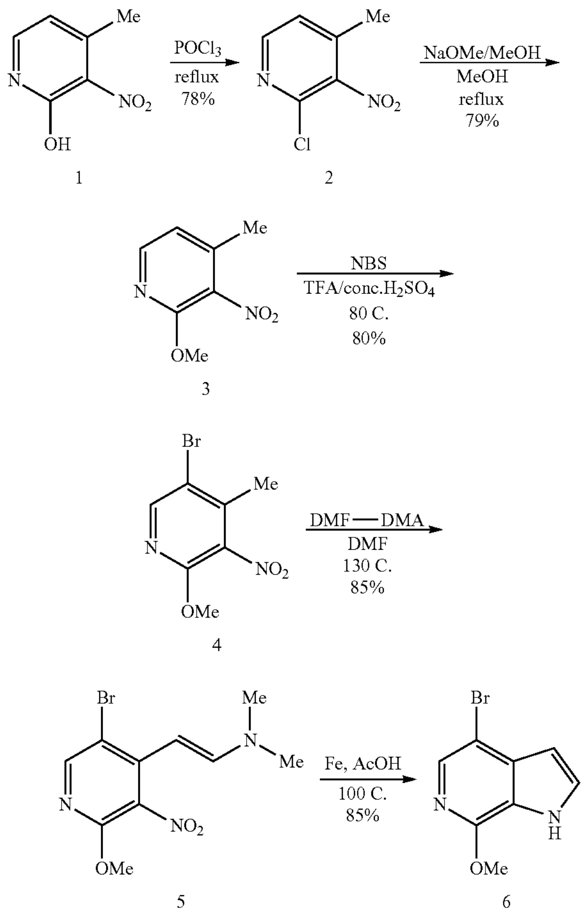

Scheme 1

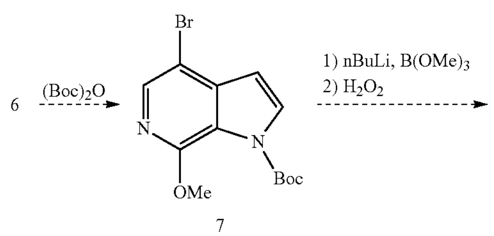

-continued

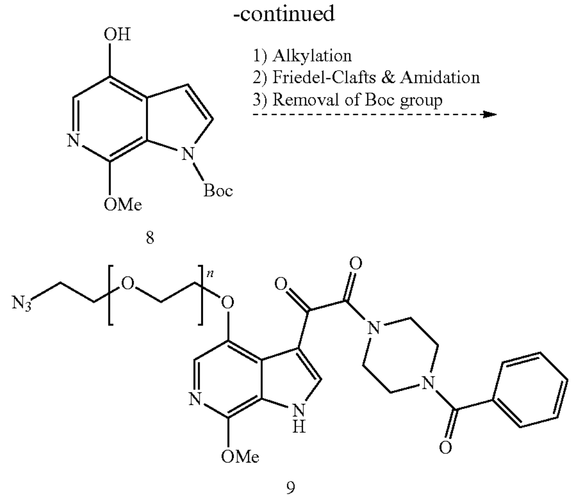

Scheme 2

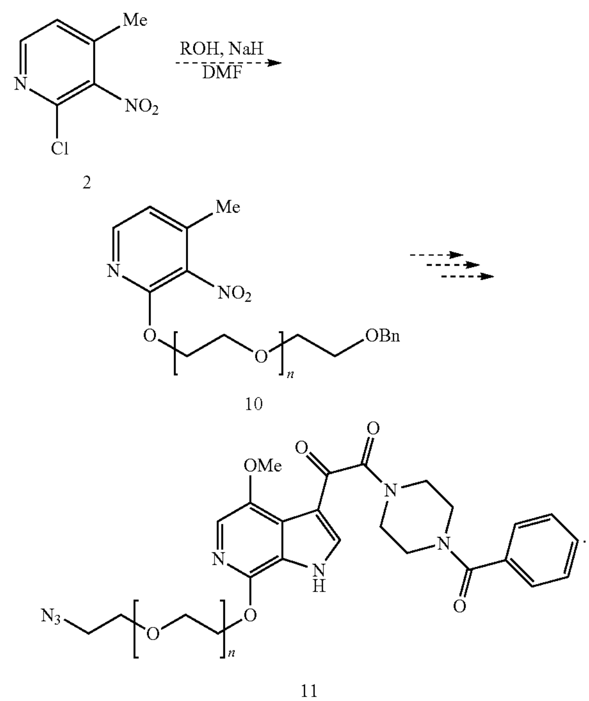

Primate Studies of Chemically Programmed Vaccines

The efficacy of chemically programmed vaccine approach using an R5-SHIV$_{SF162P3}$ macaque model and vaginal challenge may be studied. Since HIV-1 transmission most typically occurs across a mucosal surface, this may be the most relevant model to test the efficacy of the vaccine approach. Immunization protocols and PA combinations may be optimized. All protocols for female Indian rhesus macaques are reviewed and approved by the Institutional Animal Care and Use Committees. The animals are housed in accordance with the American Association for Accreditation of Laboratory Animal Care Standards. At the start of all experiments, all animals are experimentally naïve and are negative for antibodies against HIV-1, SIV, and type D retrovirus. Groups consist of 6 animals each. Groups 1 and 2 may be immunized with reactive immunogens as per optimized protocols. Group 3 may remain unimmunized. Following immunization antibody titers may be determined and the optimal Programming Agent(s) administered to groups 1 and 3. At the time point determined to provide clearance of free programming agents, animals may be challenged with virus. Animals may be treated with medroxyprogesterone acetate (Depo-Provera), by i.m. injection 30 days prior to challenge as established in previous studies. The challenge virus diluted in 1 ml PBS is introduced atraumatically into the vagina with an 8 French pediatric feeding tube attached to a syringe barrel. Macaques may be maintained in an immobilized state, with the perineum slightly elevated, for approximately 15 min post viral challenge. The challenge dose may be 300 $TCID_{50}$ based on previous studies that have consistently resulted in infection of all control animals. All experimental animals are monitored by assessing routine hematology, CD4 and CD8 lymphocyte subset counts, antibody serum concentration, neutralization titer, blood chemistry and plasma viral loads at regular intervals. Inguinal lymph nodes are biopsied, and monitored for infection by long-term co-culture assays.

The following examples are intended to illustrate but not limit the disclosure.

EXAMPLES

Materials and Methods

Antibodies, Reagents, Targeting Agents mAb 38C2 was prepared as described and is commercially available from Sigma-Aldrich (St. Louis, Mo.). Antibodies mAb LM609, mAb P1F6, and purified integrin proteins were obtained from Chemicon (Temecula, Calif.). FITC-conjugated donkey anti-mouse IgG polyclonal antibodies and horseradish peroxidase (HRP)-conjugated goat anti-mouse IgG polyclonal antibodies were from Jackson ImmunoResearch Laboratories (West Grove, Pa.). JW-KLH and JW-BSA were prepared as described. (4) Targeting agents SCS-873, SCS-397, and cRGD-dk were prepared in accord with published methodologies (10, 13, 35). cRGD peptide (cyclo (Arg-Gly-Asp-D-Phe-Lys)) was obtained from Peptides International, Inc. (Louisville, Ky.).

Cell Lines, Cells, and Animals

Mouse colon carcinoma cell line CT26 (syngeneic with BALB/C mice) were purchased from American Type Culture Collection (ATCC, Manassas, Va.) and were maintained in DMEM supplemented with 4 mM L-glutamine, 1.5 g/L sodium bicarbonate, 4.5 g/L glucose, 1 mM sodium pyruvate, 10% FCS, and antibiotics. B16F10 mouse melanoma cell line (syngeinic with C57BL/6) was purchased from ATCC and maintained in RPMI medium 1640 containing 10% FCS and antibiotics. Female (5-6 weeks of age) BALB/C, C57BL6, and FcgRIII knockout mice in the C57BL6 background, strain name B6.129P2-Fcgr3$^{tm1Sjv}$/J, were obtained from Jackson Labs. NK cells were isolated from spleen of BALB/C and C57BL6 mice using the MACS system according to the manufacturer's recommendations (Miltenyi Biotech, Auburn, Calif.). Non-NK cells (i.e. B cells, T cells, dendritic cells, macrophages, granulocytes and erythroid cells) were depleted with a cocktail of biotin-conjugated antibodies against CD19, CD4 (L3T4), CD8a (Ly-2), CD5 (Ly-1), Ly-6G (Gr-1) and Ter-119, and anti-biotin MicroBeads. Purity of NK fractions was >95% as determined by FACS analysis.

Reactive Immunization and ELISA Titering

Mice were immunized with JW-KLH according to the published method with antigen boosting on days 15 and 43 (4). Individual JW-antiserum from JW-KLH-immunized mice was collected on days 22, 50, and 85 and used for in vitro assays. For ELISA, Costar 96-well ELISA plates (Corning, Acton, Mass.) were coated with 100 ng of JW-BSA in 25 µL PBS and incubated overnight at 4° C. After blocking with 150 µL of TBS/3% BSA for 2 hr at 37° C., 50 µL of different dilutions (from 1:500 to 1:64000) of pooled (5 mice each strain) sera was added into each well and the plates were incubated for 2 h at 37° C. Washing and detection were performed essentially as described (14) using HRP-conjugated goat anti-mouse IgG antibody (diluted 1:3000 in TBS/ 1% BSA). In some experiments, additional incubation with 50 µL of 0.05M Citric Acid, pH 2.5 (acid wash) for 15 min at RT was performed after the initial washing step. The quantitation of anti-JW IgG1, IgG2a, IgG2b, IgG3, IgGA, and IgM antibodies, ELISA was performed using biotin-conjugated goat-anti-mouse Ig-specific antibodies and Streptavidin-conjugated HRP (Caltag). "Covalent antibody titer" as used herein is defined as the antibody titer measured following citric acid washing steps.

Chemical programming, evaluation of binding to integrins in ELISA and on cells, complement-dependent cytotoxicity, and antibody-dependent cellular cytotoxicity assays were performed as previously described (14).

Syngeneic Colon Cancer Model

On day 65, JW-KLH-immunized BALB/C mice were sorted (6 groups with 6 animals each) to form matched anti-JW titer groups and were inoculated s.c. into right flanks with 0.1 mL (2×10$^5$ cells/mouse) of CT26 cell suspension in PBS (day 0 for tumor model). Animals were further injected i.p. with identical amounts of the targeting compound in 200-µL of PBS on days 2, 5, 8, 11, 14, and 17. Tumor volumes of treated animals were measured over the skin in two dimensions using a slide caliper every third day starting on day 12, and the tumor volume was calculated according to the following formula, ½(width)$^2$×length. Toxicity was monitored by determining the body weight of mice once a week. On day 30, all mice were euthanized and the tumors dissected and weighed. Results are reported as means±SD for each group. Differences were considered statistically significant at P<0.05 using unpaired two-tailed Student's t test. All of the animal experiments were approved by the Institutional Animal Care and Use Committee of the Scripps Research Institute before the experiments were started.

Syngeneic Melanoma Model

B16 melanoma tumor model using C57BL6 and FcgRIII knockout mice immunized with JW-KLH was performed as described above, except all mice were euthanized on day 24.

Results and Discussion

Figure 1B:
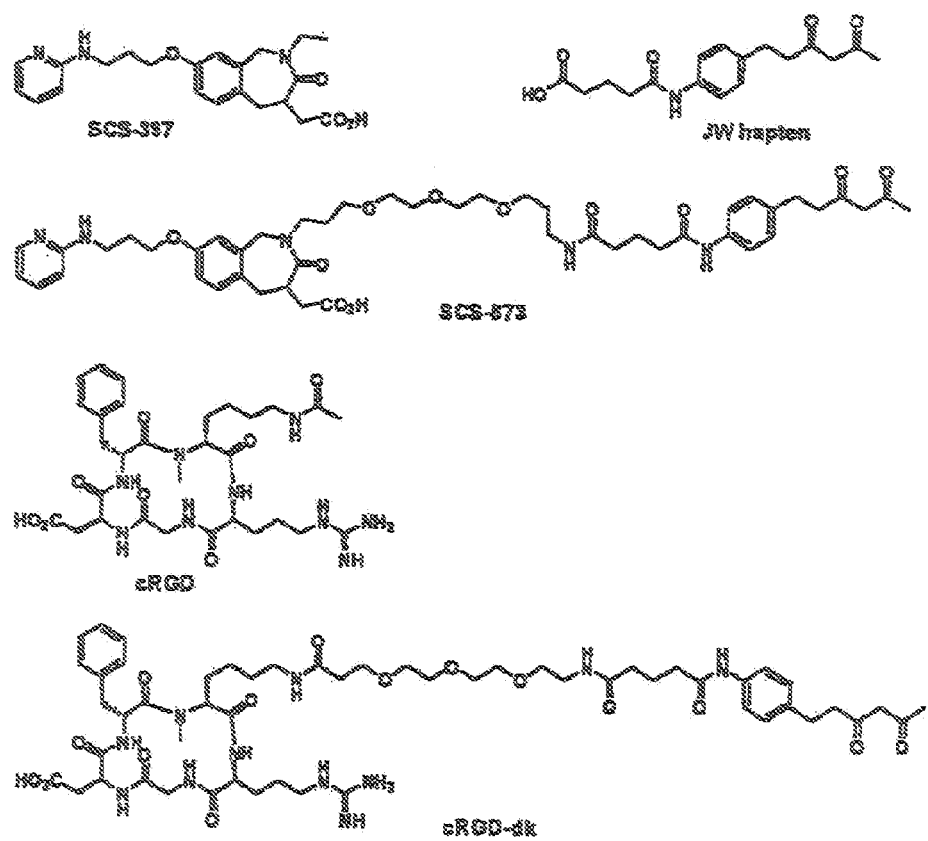

In previous studies the covalent binding monoclonal antibody 38C2 was programmed with a variety of targeting agents and studied in multiple cancer models using human tumor xenografts in immune-deficient mice. In order to explore the potential of an elicited covalent immune response, we have turned to immune competent mice and syngeneic cancer models. We aimed to determine if a high-titer covalent antibody response could be elicited in a variety of murine strains. We also sought to show that the induced responses could be programmed to bind murine (self) targets relevant to cancer and impact tumor growth in murine cancer models. Integrins $α_vβ_3$ and $α_vβ_5$ were chosen as target antigens since these surface proteins are expressed by a wide variety of tumor types and on angiogenic vasculature. Furthermore, we had previously validated these integrins as therapeutic targets using chemically programmed monoclonal antibody 38C2 (cp38C2). The targeting of integrins $α_vβ_3$ and $α_vβ_5$ with a chemically programmed immune response is illustrated in FIG. 1A. The compounds SCS-873 and cRGD-dk (FIG. 1B) serve as chemical adaptors that react with covalent antibodies through their diketone tags to redirect the binding of the immune response to the integrins expressed on cell surfaces. Because cell-bound antibodies can bind through their Fc regions to molecules of the complement cascade, (such as C1q) and to Fc receptors expressed on the surface of immune effector cells (such as natural killer cells), programmed immunity can potentially direct complement-directed cytotoxicity and antibody-dependent cellular cytotoxicity.

SCS-873 and cRGD-dk Program Antibody mAb 38C2 to Bind Human and Mouse Integrins

Figure 2A:
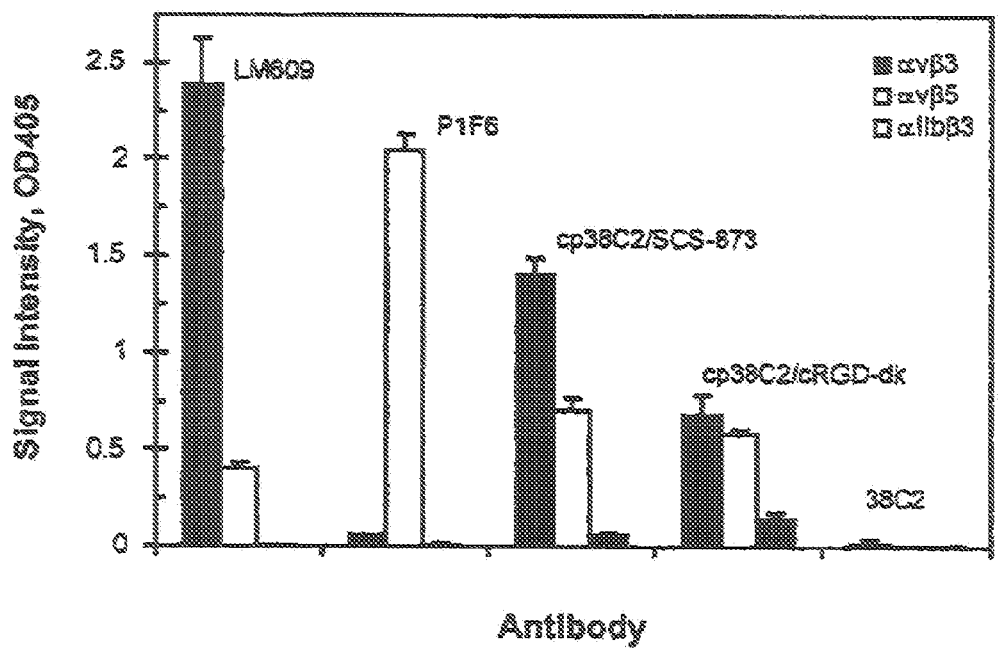
FIG. 2 illustrates adaptor validation through cp38C2 binding to integrins and integrin-expressing cells: (A) Specific binding of cp38C2 to human integrins $\alpha_v\beta_3$ and $\alpha_v\beta_5$ was measured by ELISA as described in the Methods. LM609 (anti-$\alpha_v\beta_3$) and P1F6 (anti-$\alpha_v\beta_5$) and mouse mAb 38C2 were also tested. Data shown represent the mean±SD of triplicate samples (B) Flow cytometry analysis of cp38C2 binding to mouse B16 melanoma, mouse colon carcinoma CT26. For studies on human M21 melanoma and mouse endothelial MS1 cell lines, see Supporting Information, all of which express both integrins $\alpha_v\beta_3$ and $\alpha_v\beta_5$ on their surface, was performed as described in the Methods. Cells were stained with cp38C2 mAb programmed with indicated ligand (bold line) and unprogrammed 38C2 mAb (thin line). Bound antibodies were detected with FITC-conjugated donkey antimouse IgG.
Figure 2B:
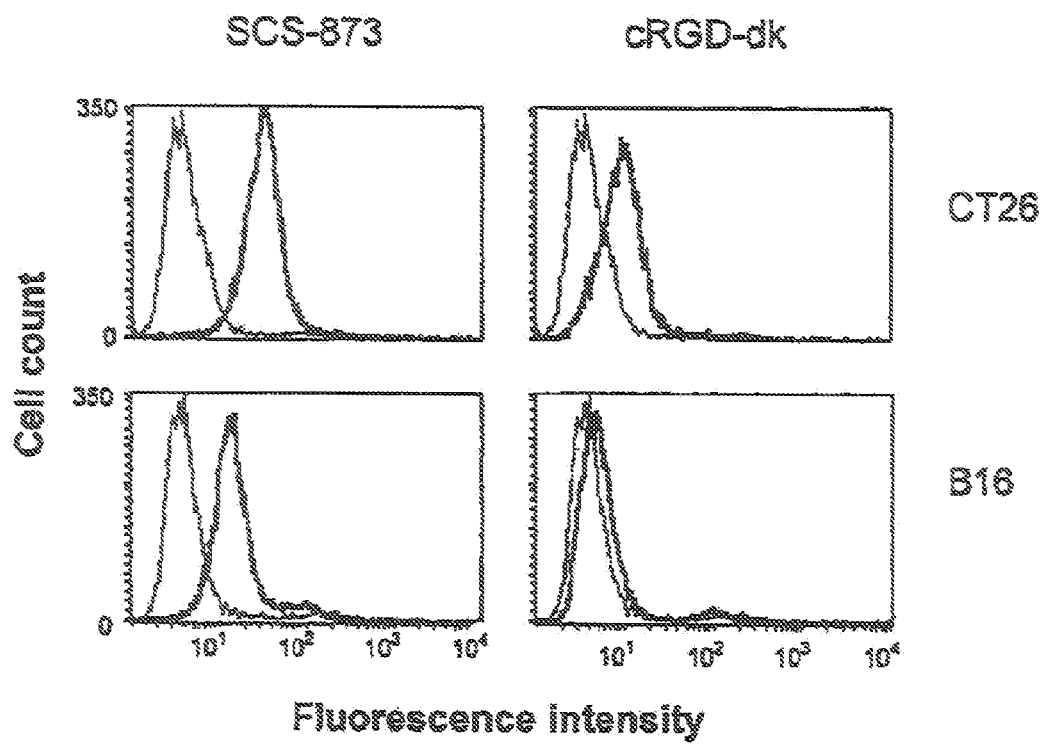
Figure 5A:
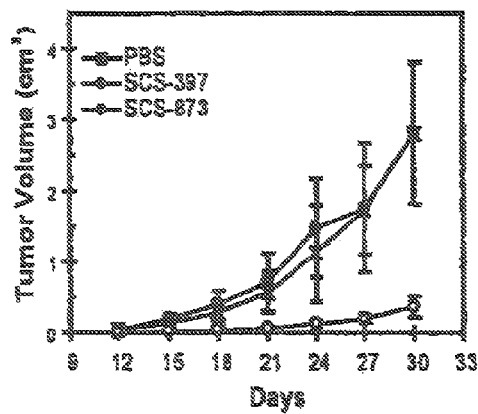
FIG. 5 illustrates inhibition of tumor growth in syngenic mice mediated by adaptor-targeted antibodies. (A) Treatment with SCS effectively inhibited growth of CT26 tumors in JW-KLH-immunized BALB/C mice. Mice (six per group) were treated between days 2 and 17 with 200 μL i.p. injections of PBS alone, 60 μg/mL SCS-873 in PBS, or 27.5 μg/mL SCS-397 in PBS. Mean tumor volumes±SD were determined at 3-day intervals from 12 to 30 days post-grafting. (B) Treatment with cRCG-dk effectively inhibited growth of CT26 tumors in JW-KLH-immunized BALB/C mice. Mice (six per group) were treated between days 2 and 17 with 200 μL i.p. injections of PBS alone, 77 μg/mL cRGD-dk in PBS, or 42.5 μg/mL cRGD in PBS. Mean tumor volumes±SD were determined at 3-day intervals from 12 to 30 days post-grafting. (C) Treatment with SCS-873 effectively inhibited growth of B16 tumors in JW-BSA-immunized C57BL6 mice. Mice (six per group) were treated between days 2 and 17 after tumor induction with 200 μL i.p. injections of PBS alone, 60 μg/mL SCS-873 in PBS, or 27.5 μg/mL SCS-397 in PBS. Mean tumor volumes±SD were determined at 3-day intervals from 12 to 24 days post-grafting. (D) Treatment with SCS-873 effectively inhibited growth of B16 tumors in JW-BSA-immunized FcγRIII knockout mice. Mice (six per group) were treated between days 2 and 17 after tumor induction with 200 μL i.p. injections of PBS alone, 60 μg/mL SCS-873 in PBS, or 27.5 μg/mL SCS-397 in PBS. Mean tumor volumes±SD were determined at 3-day intervals from 12 to 24 days post-grafting.
Figure 5B:
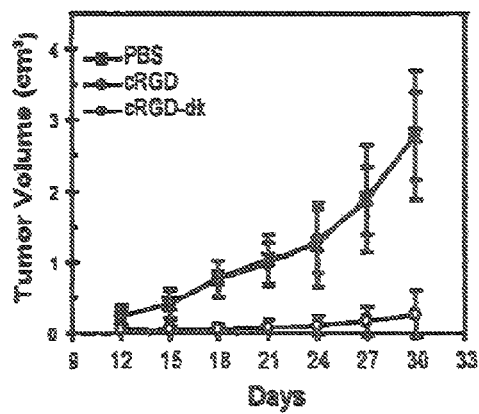
Figure 5C:
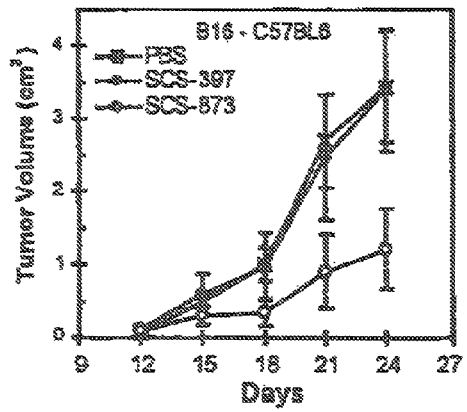

In order to validate the potential of SCS-873 and cRGD-dk to reprogram mAb 38C2 to bind integrins αvβ3 and αvβ5 expressed on murine cancer cell lines, specific binding of cp38C2, formed following reaction with SCS-873 or cRGD-dk, was established in an ELISA using human integrin αvβ3 and αvβ5 (FIG. 2A). Both compounds were effective in directing 38C2 to bind αvβ3 and αvβ5; importantly, neither programmed antibody bound well to integrin αIIbβ3. Next, using flow cytometry, we showed that the cpAbs bound to integrin receptors expressed on murine cells, colon cancer line CT26 and melanoma line B16 (FIG. 2B). SCS-873 programmed antibody provided more robust binding to CT26 cells than the cRGD-dk programmed antibody. With B16 cells, no substantial binding of cRGD-dk programmed antibody was observed, whereas a substantial staining was observed using SCS-873 programmed antibody. As previously shown for SCS-873 (14), cRGD-dk effectively stained cells from the mouse endothelial cell line MS1 and from the human melanoma cell line M21 (see Supporting Information). In these and other studies, the corresponding targeting agents lacking diketone tags, SCS-397 and cRGD, served as negative controls; these molecules lack the diketone functionality required to bind to mAb 38C2 or to polyclonal antibodies induced through immunization with the β-diketone hapten JW.

Reactive Immunization

Immunization with keyhole limpet hemocyanin (KLH) coupled to JW hapten (JW-KLH) or to other diketone haptens has been used for the preparation of a variety of covalent-binding, monoclonal antibodies. Reactive immunization differs from classical immunization approaches in that reactive chemicals, in this case β-diketones, are used as immunogens and provide the immune system with the opportunity to select for the formation of a covalent bond between the antibody and the reactive antigen during the maturation of the immune response. Here, to elicit a covalent polyclonal antibody response through immunization, three mouse strains (BALB/C, C57BL/6, and -FcγRIII (receptor knockout mice)) were immunized with JW-KLH and subsequently boosted with two additional injections of JW-KLH. Immune serum was pooled from immunized animals of each strain and examined by ELISA for induction of covalent binding antibody responses. Using a panel of 20 monoclonal antibodies, we have demonstrated that monoclonal antibodies that bind covalently to the JW hapten through enaminone formation are not released following treatment with acid (0.05M citric Acid, pH 2.5), whereas non-covalent, albeit high-affinity, JW-binding antibodies are readily released following an acid wash (see Supporting Information). Non-covalent complexes are readily disrupted at low pH, the buffer type typically used as an eluant in antibody affinity chromatography. Therefore, acid-wash ELISA allowed us to approximate the covalent polyclonal JW titer. Substantial covalent antibody titers were found for all three mouse strains (FIG. 3) and, with the exception of IgA, a variety of antibody isotypes were found to constitute the anti-JW response (Table 1).

TABLE 1

| Mice | Serum Titer | anti-JW Ab isotypes (%) IgG1 | IgG2a | IgG2b | IgG3 | IgM | IgA |
|---|---|---|---|---|---|---|---|
| BALBC | 1:3000 | 21 | 16 | 21 | 18 | 23.5 | 0.5 |
| C57BL6 | 1:6000 | 22 | 5 | 20 | 34 | 18.5 | 0 |
| FcγRIII | 1:6000 | 23 | 3.5 | 20 | 25 | 28 | 0.5 |

Upon addition of SCS-873 to immune sera, the serum was efficiently programmed to bind integrin $\alpha_v\beta_3$ as demonstrated by ELISA (FIG. 4). It should be noted that while the programmed immunoglobulins all display the same antigen specificity as programmed by the adapter ligand, antibodies of the various isotypes will display the adapter ligands with different display valancies; IgM will display 10 adapter ligands and very avidly bind to cell surfaces while IgG classes will display 2 adapter ligands and induce a different spectrum of immune effector functions. Pre-immune serum did not react with SCS-873 and did not bind to integrin following addition of SCS-873.

Programmed Polyclonal Immune Responses have Therapeutic Effects in Cancer Models We evaluated the therapeutic potential of this approach in two syngeneic cancer models, the murine CT26 colon tumor model (24) and the B16 syngeneic melanoma model (25). In the first model, tumor induction was performed by subcutaneous injection of CT26 cells into the right flank of JW-KLH-immunized BALB/C mice. Three different groups of six mice with similar anti-JW titers were treated between days 2 and 17 after tumor induction in two independent experiments. In the first experiment (FIG. 5A), mice were given 200-μL intraperitoneal (i.p.) injections of PBS alone, 60 μg/mL SCS-873 in PBS, or 27.5 μg/mL SCS-397 (equimolar to the SCS-873 dosage) in PBS according to the schedule described in Methods and Methods. In the second experiment (FIG. 5B), mice were given 200 μL i.p. injections of PBS alone, 77 μg/mL cRGD-dk in PBS, or 42.5 μg/mL cRGD in PBS. Tumor volumes were measured at 3-day intervals from 12 to 30 days post-engraftment and removed and weighed at the end of the experiment. Profound and statistically significant reduction in tumor growth was observed in animals treated with targeting agents designed to covalently program the immune response: Treatment with SCS-873 resulted in approximately 75% reduction ($P<0.003$) and treatment with the cRGD-dk resulted in approximately 90% reduction ($P<0.0002$) in tumor weight relative to treatment with PBS at 30 days. Treatment of mice with ligands that lack the diketone tags necessary for binding to anti-JW immunoglobulins (SCS-397 and cRGD) was no more effective than treatment with PBS.

We next evaluated our approach in the B16 syngeneic melanoma model in C57BL6 mice. Previous studies have demonstrated the efficacy of treating xenografted human melanoma in immunocompromised mice using SCS-873 and mAb38C2. Since flow cytometry studies indicated strong binding of SCS-873 to B16 cells and insignificant binding of cRGD-dk to these cells (FIG. 2), only SCS-873 therapy was studied in this model. Tumor induction was performed by subcutaneous (s.c.) injection of $2\times10^5$ B16 cells into the right flank of C57BL/6 mice previously immunized JW-KLH. Three groups of six mice were treated between days 2 and 17 after tumor induction. Mice were treated with 200-μL i.p. injections of PBS alone, 60 μg/mL SCS-873 in PBS, or 27.5 μg/mL SCS-397 in PBS according to the schedule described in Methods and Methods. As shown in FIG. 5C, growth of this very aggressive tumor was significantly inhibited in mice treated with SCS-873 (78% growth inhibition, P<0.004, relative to treatment with PBS); tumor volumes were similar in mice treated with SCS-373 and PBS buffer.

Polyclonal Antibody Effector Functions can be Chemically Programmed

Figure 3A:
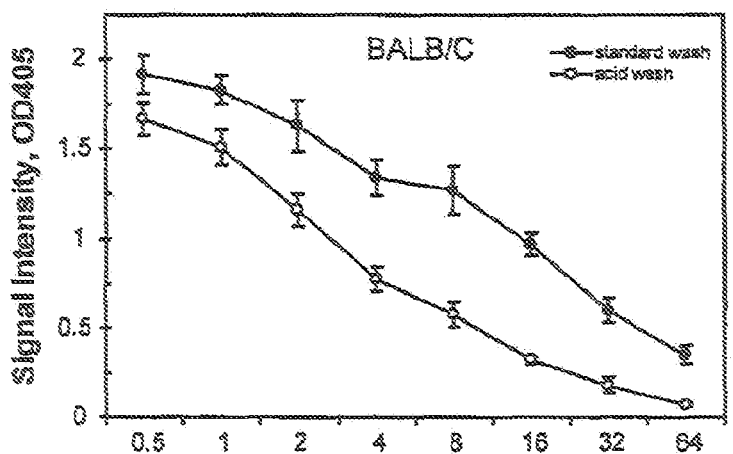
FIG. 3 illustrates induction of high-titer covalent antibody responses: Mice were immunized with JW-KLH and subsequently boosted with two additional injections of JW-KLH. Direct binding of indicated dilutions of pooled immune serum from (A) BALB/C, (B) C57BL6, and (C) FCγRIII knockout mice to immobilized JW-BSA was measured by ELISA as described in Materials and Methods. This acid-insensitive binding provided an indirect measure of covalent antibody titer.
Figure 3B:
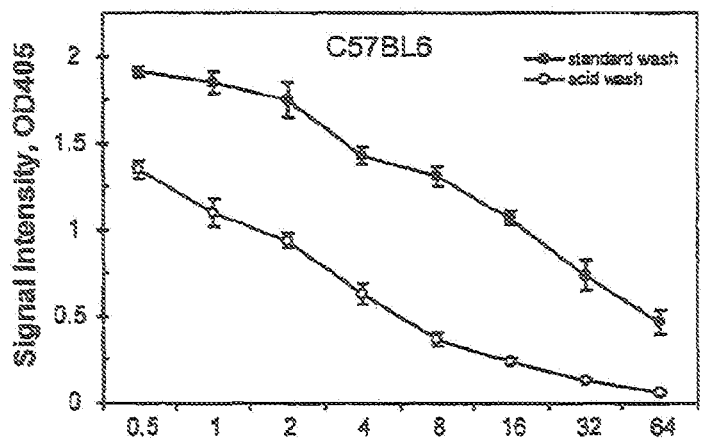
Figure 3C:
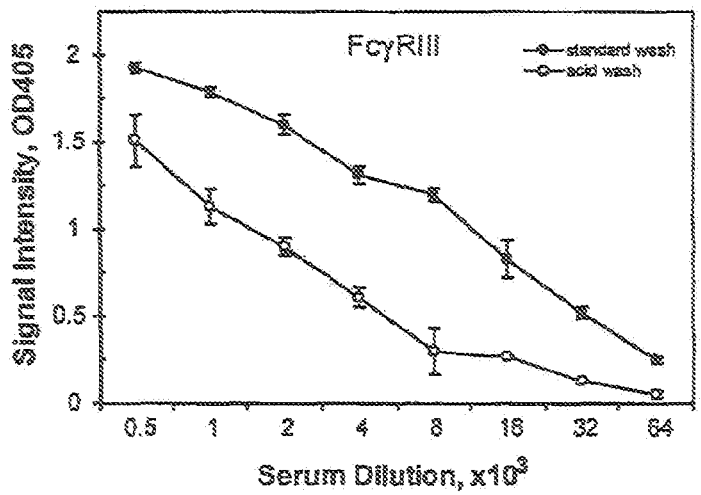
Figure 4:
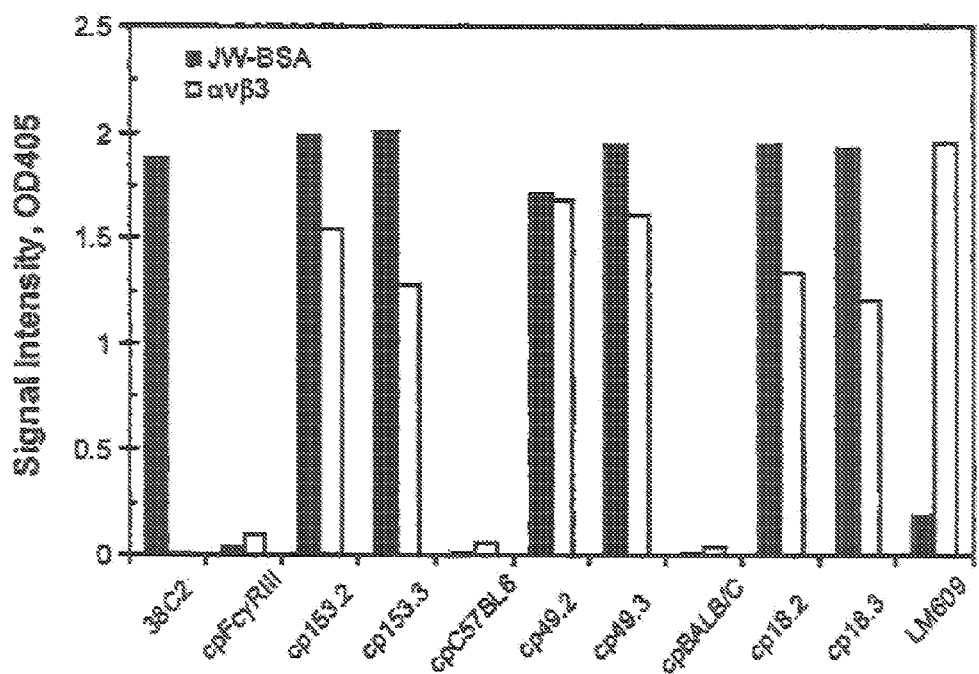
FIG. 4 illustrates adaptor-mediated redirection of anti-JW hapten antibody binding. Specific binding of anti-JW hapten mouse sera to human integrins $\alpha_v\beta_3$ in the presence of SCS-873 was measured by ELISA as described in Methods. Mouse LM609 (anti-$\alpha_v\beta_3$) and 38C2 (anti-JW) mAbs were also tested. Sera was tested at days 0, 22, and 50 post-immunization.
Figure 5D:
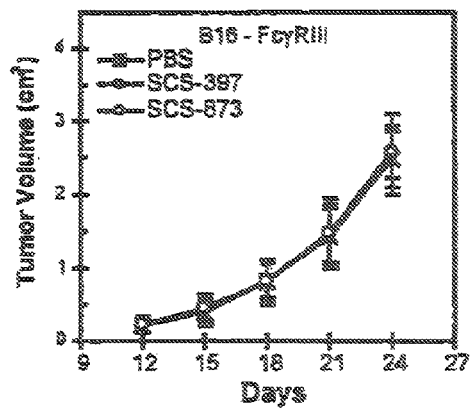

The antibody effector functions ADCC and CDC are believed to be key mechanisms underlying the tumor-growth inhibiting activities of therapeutic antibodies (25). ADCC is mediated by the activation Fcγ receptor, FcγRIII, and modulated by its inhibitory counterpart, FcγRIIB (25). Natural killer cells, which express FcγRIII but not FcγRIIB, are a principal cell type involved in ADCC. We hypothesized that a significant component of the therapeutic effect that we observe using the programmable immunization strategy results from antibody-mediated cellular cytotoxicity. We, therefore, evaluated the growth of B16 tumors in C57BL/6 mice lacking FcγRIII (strain B6.129P2-Fcgr3$^{tm1Sjv}$d from Jackson Laboratory). In these animals, the Fcgr3$^{tm1Sjv}$ targeted mutation eliminates the ligand-binding a chain of FcγRIII and the mice lack NK cell-mediated antibody-dependent cytotoxicity. FcγRIII knockout mice produced similar levels of covalent diketone binding antibody induced by immunization (FIG. 3). In FcγRIII knockout mice, however, treatment with SCS-873 did not inhibit tumor growth (FIG. 5D), clearly indicating that ADCC is a major mechanism of therapeutic action in this model.

Figure 6A:
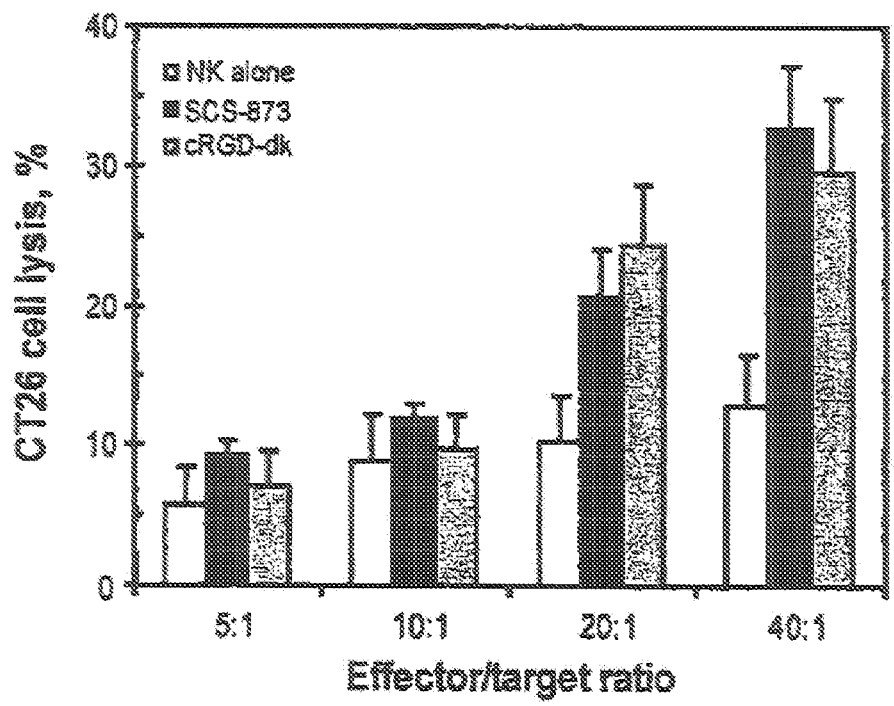
FIG. 6 illustrates NK cell-mediated ADCC activity of chemically programmed antibodies. (A) Radiolabeled CT26 tumor cells were mixed with SCS-873- or cRGD-dk-programmed BALB/C mouse sera and lysis was measured in the presence of BALB/C spleen-isolated NK cells as effectors. (B) Radiolabeled B16 tumor cells were mixed with SCS-873- or cRGD-dk-programmed C57BL6 mouse sera and lysis was measured in the presence of C57BL6 spleen-isolated NK cells as effectors. The values shown are means of triplicate samples (±SD).
Figure 6B:
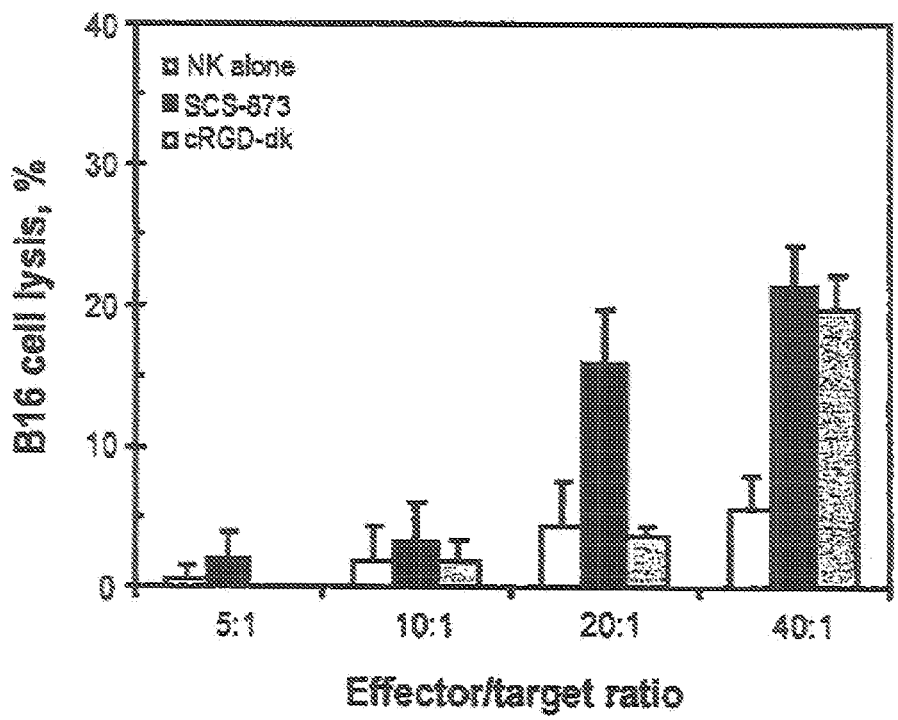

To further confirm our hypothesis that ADCC mediates the activity of our programmed antibodies, we isolated NK cells from the spleens of C57BL6 and BALB/C mice and assessed their ADCC capacity in vitro using B16 melanoma and CT26 colon cancer lines as targets. Sera derived from immunized animals and programmed with SCS-873 and cRGD-dk clearly potentiated NK cell killing of CT26 and B16 cells (FIG. 6). These results were similar to those reported earlier using mAb 38C2 and the human melanoma line M21. To examine the potential of the polyclonal response to direct complement-directed cytotoxicity, we studied the lysis of radiolabeled CT26 and MS1 cells in the presence of SCS-873 programmed polyclonal sera and rabbit complement using a standard [$^{51}$Cr]-release assay. This experiment demonstrated significant CDC-based killing of CT26 cells in the presence of SCS-873-treated immune sera supporting the potential of this immunization strategy and chemical programming to direct CDC (see Supporting Information).

SUMMARY

The development of new and more effective vaccine strategies is critical for public health. Despite decades of effort, no effective vaccines are available for diseases such as HIV-1 and malaria. We believe that chemistry-based vaccine approaches have been underexplored and may provide opportunities to make inroads into intractable areas of vaccinology. In contrast to biology-based vaccine approaches, which aim to educate the immune system to create immunoglobulins of a defined specificity, the chemistry-based vaccine approach described here provides the immune system with defined specificities by coupling the biology-based induction of programmable immunoglobulins with ligand design and covalent self-assembly. The earliest related chemistry-based vaccine strategies were aimed at redirecting common natural antibody specificities such as anti-dinitrophenyl and anti-α-galactosyl antibodies to targets by decorating them with highly immunogenic antigens like dinitrobenzene and galactosyl-α(1-3)galactose. Such natural antibody specificities are typically of low affinity and to the best of our knowledge no such study has reported efficacy in a disease model. More recently, fluorescein-hapten based immunizations were proposed as an alternative to the ineffective low affinity natural antibody approach; in this strategy, induced high-affinity anti-fluorescein immunoglobulins are programmed with fluorescein conjugates. This strategy was effective in animal models of cancer but only when combined with cytokine or radiation adjuvant therapy and may suggest therapeutic limitations inherent with non-covalent approaches.

The efficacy of our chemically programmed, covalent monoclonal antibody approach has been proven in multiple animal models of disease and chemically programmed antibodies are now being evaluated in multiple clinical studies. Here, we demonstrate the efficacy of this approach as a covalent vaccine strategy. We showed that high-titer covalent antibody responses were induced in three mouse strains and that the resulting polyclonal antibody responses could be reprogrammed to target the integrins $\alpha_v\beta_3$ and $\alpha_v\beta_5$ with therapeutic effect. Unlike earlier noncovalent approaches based on natural antibodies or anti-fluorescein responses, no adjuvant therapy was required. The integrins we have targeted are of significant interest because the malignant progression of melanoma, glioma, ovarian, cervical, and breast cancer have all been strongly correlated with the level of expression of the integrin $\alpha_v\beta_3$ and in some cases with $\alpha_v\beta_5$. Additionally, these integrins are expressed on the surface of angiogenic endothelial cells and are thus targets of anti-angiogenic therapy. The studies presented here further validate the potential of targeting these receptors in melanoma and colon cancer therapy.

Figure 7:
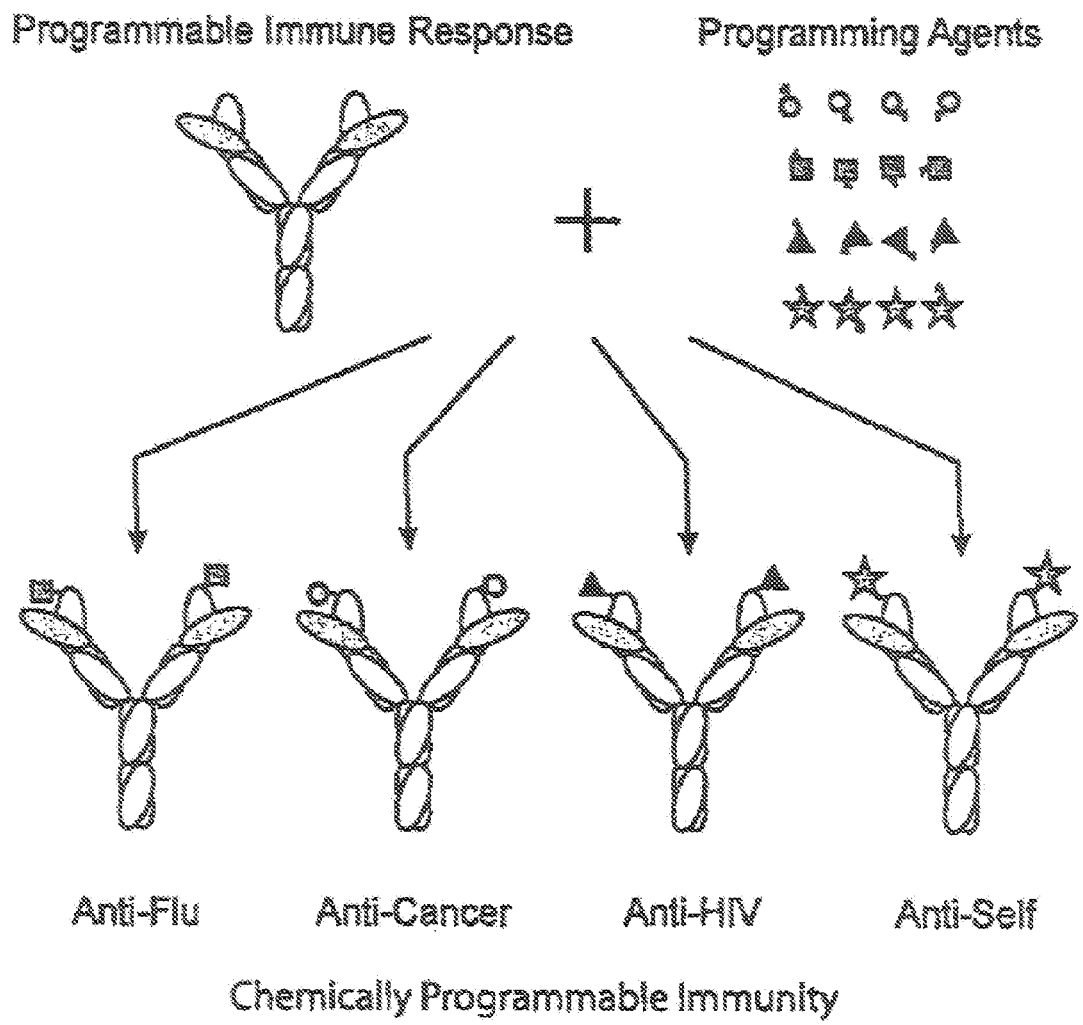
FIG. 7 illustrates the broad potential of the chemically programmable covalent vaccine strategy. With the development of a wide variety of targeting molecules (different geometric shapes as shown), chemically programmed vaccines can be created to address a number of diseases and biological threats.
Figure 8A:
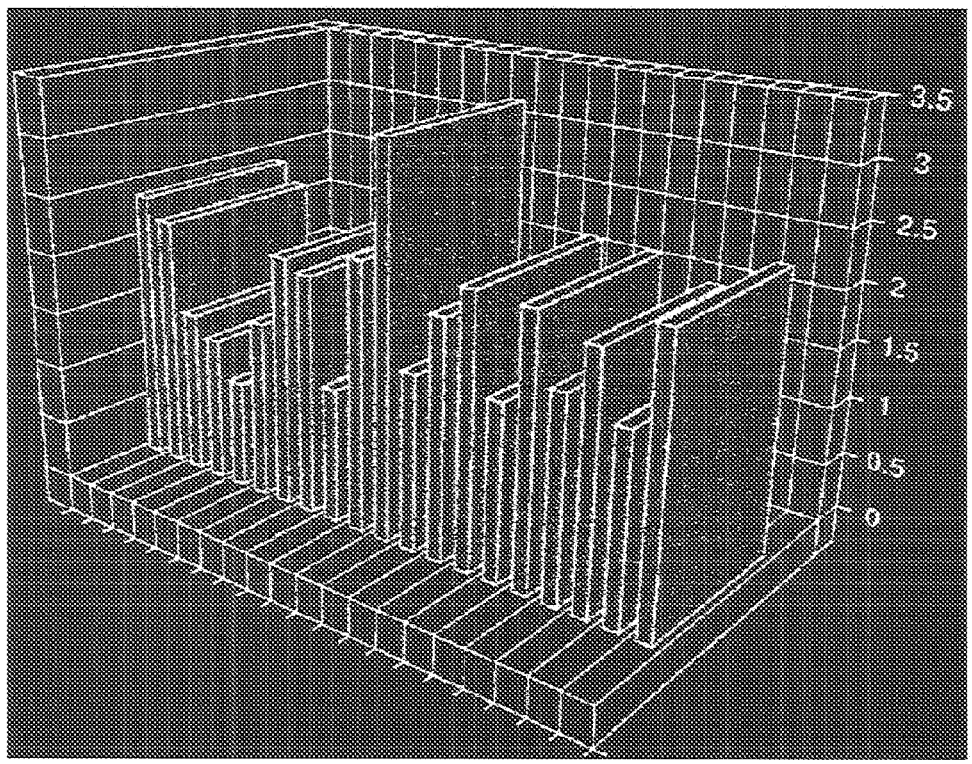
FIG. 8 illustrates monoclonal antibodies 38C2 and 33F12 form covalent acid-stable complexes with the a-JW hapten. Twenty monoclonal antibodies that bind JW-BSA with high-affinity were generated and tested (1). Binding was assessed using a a-JW hapten-binding ELISA as described in the material and methods section. The graphs showed the results for the binding ELISA (absorbance at 405 nm) without an acid wash (A) or after the acid wash (B) of the monoclonal antibodies assayed confirmed a covalent binding to a-JW hapten. Covalent binding of these antibodies was confirmed using multiple assays (1). Since covalent binding is also key to the catalytic mechanism of the Aldol reaction, these antibodies were the only catalytic antibodies of the 20 assayed.
Figure 8B:
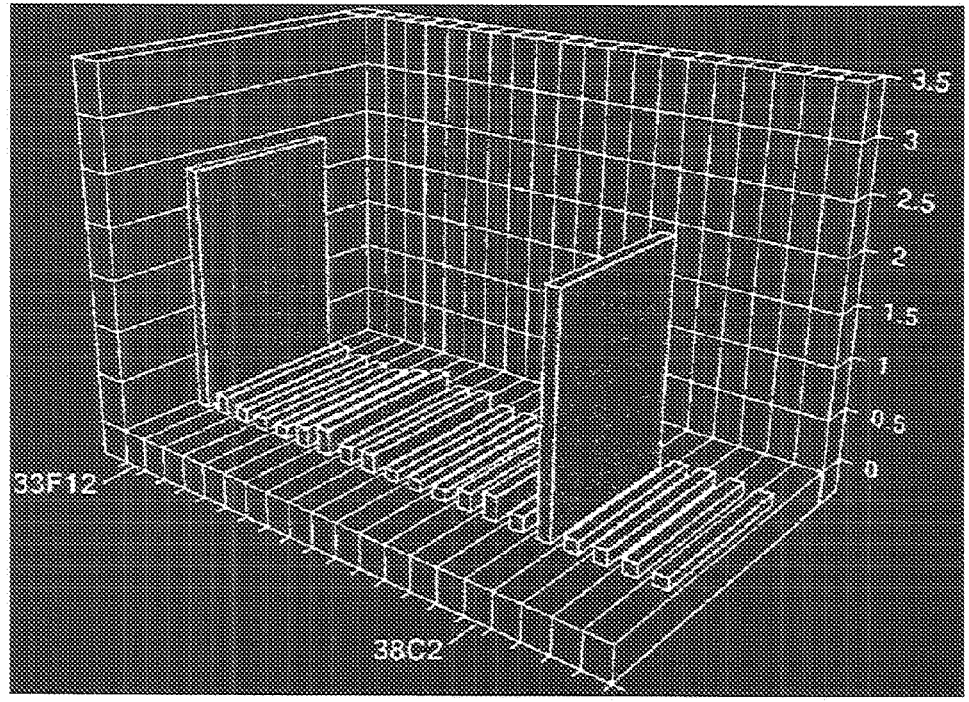
Figure 9:
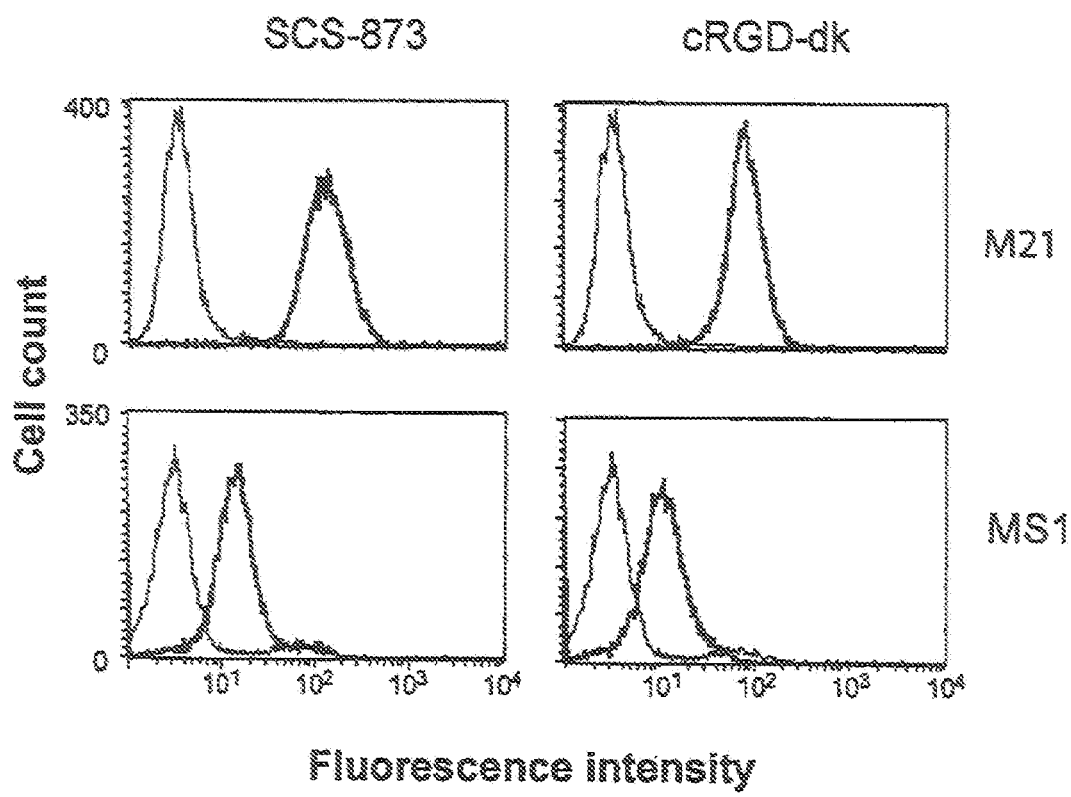
FIG. 9 illustrates adaptor validation through cp38C2 binding to integrin-expressing cells. Flow cytometry analysis of cp38C2 binding to human melanoma M21 a and mouse endothelial MSI cell lines, all of which express both integrins $a_vp3$ and $a_vPs$ on their surface, was performed as described in the Methods. Cells were stained with cp38C2 mAb (bold line) and unprogrammed 38C2 mAb (thin line). Bound antibodies were detected with FITC-conjugated donkey anti-mouse IgG.
Figure 10:
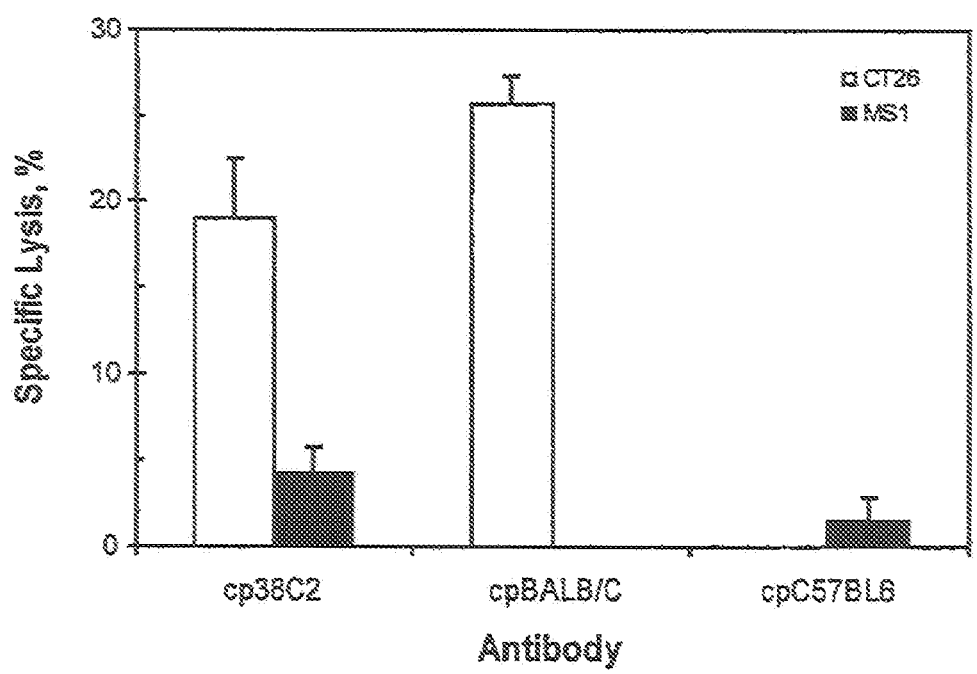
FIG. 10 illustrates tumor cell killing by redirected antibodies in the presence of complement (CDC). Lysis of radiolabeled CT26 and MSI cells in the presence of antibodies and rabbit complement was measured by a standard [$^{51}$Cr]-release assay as described in Methods (2). The values shown are means of triplicate samples (±SD).

While we focused our efforts toward programming an induced covalent antibody response against self receptors, we believe that this approach can be broadly applied to a wide variety of diseases (see, FIG. 7). The development of several ligands directed against different epitopes on a virus like HIV-1, for example, might produce programmed immunity that reduces the potential for viral escape or broadens prophylactic efficacy. A universal covalent vaccine approach might have other advantages. Recent studies have highlighted the long-lived nature of the circulating B memory cell in response to influenza. Such a long-lived covalent vaccine response might be a solution to age-related decline in humoral immunity if such a vaccine is given early in life. Furthermore, if widely adopted, universal programmable covalent polyclonal antibodies would be readily available for passive transfer to non-immunized individuals who could be provided with 'instant immunity' following administration of a designed ligand.

Orally available programming agents would provide a convenient means of directing an immune response with a compound that could both be stock-piled and administered en masse in response to a biological threat or pandemic. This approach should have considerable economic advantages as compared to classic monoclonal antibody therapy. Since this approach induces a wide variety of antibody isotypes, the full range of effector functions and valencies available to the immune system can be tapped in this approach.

It is also possible to use animal systems (e.g., transgenic animals) to produce antibodies by methods described herein, as exemplified by Kuroiwa et al. (Nat. Biotec. 27(2):173-181, 2009), herein incorporated by reference. In this paper, hyper-immunization with anthrax protective antigen triggered a hIgG-mediated humoral immune response comprising a high proportion of antigen-specific hIgG. Purified, fully human and chimeric hIgGs were highly active in an in vitro toxin neutralization assay and protective in an in vivo mouse challenge assay. The results in Kuroiwa et al. Demonstrate the feasibility of using a bovine system to produce a large volume of highly active antibodies for human therapy. Alternatively, one could use other animal systems, including murine systems, to produce polyclonal antibodies. Such antibodies could then be administered to a mammal (e.g., human) together with a targeting compound.

In Vitro programming with Aplaviroc

Figure 19:
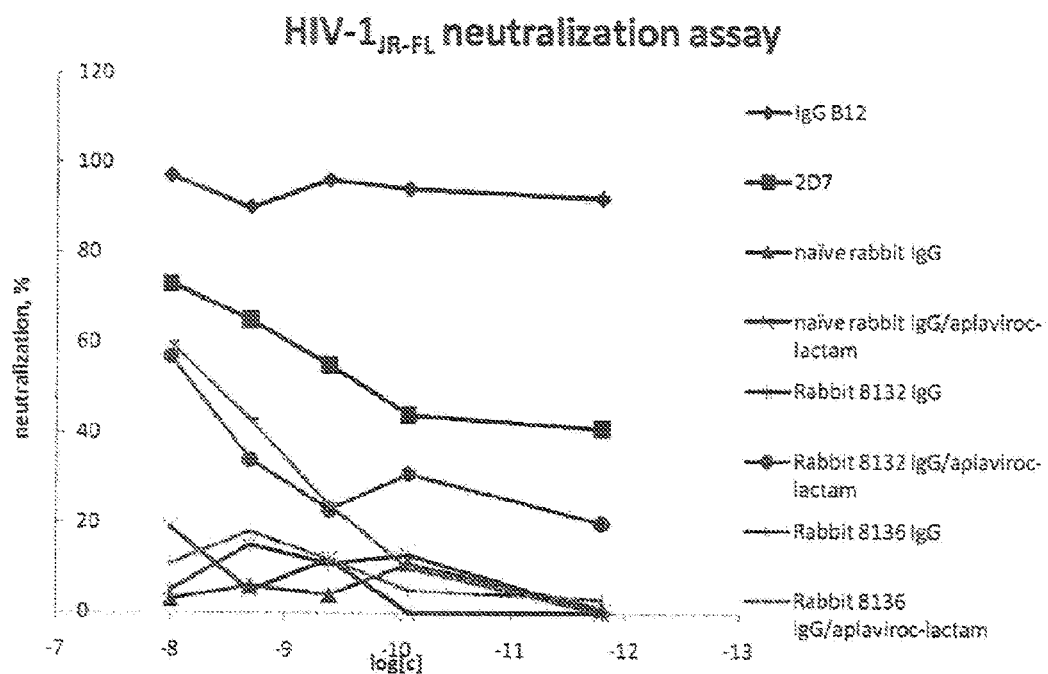
FIG. 19 illustrates in vitro programming with aplaviroc in the HIV-1$_{JR-FL}$ neutralization assay.

FIG. 19 illustrates in vitro programming with aplaviroc in the HIV-1$_{JR-FL}$ neutralization assay.

Polyclonal IgG was purified using protein A column from the naïve and immunized rabbits (#8188—naïve; #8132—diketone immunized; #8136—lactam immunized).

Purified IgG was treated with 10 eq of aplaviroc-diketone or aplaviroc-lactam for 24 h, followed by 48 h dialysis.

Aplaviroc-diketone:

The neutralization assay results are shown in FIG. 19. Rabbit 8132 was immunized with diketone; 8136—with lactam.

In Vivo programming with Aplaviroc

Figure 20:
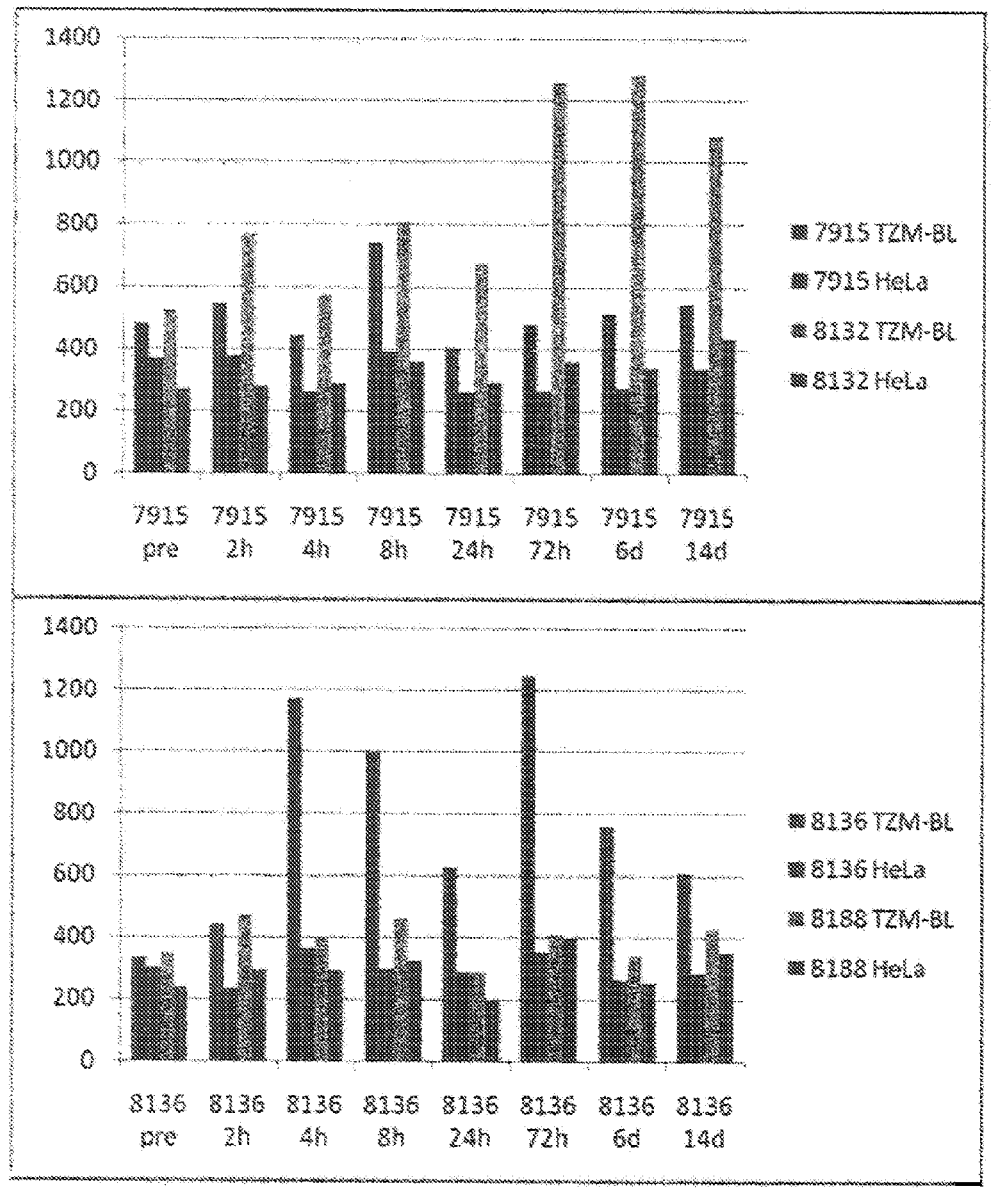
FIG. 20 illustrates the in vivo programming with aplaviroc in the HIV-1 CCCR5 binding FACS.

FIG. 20 illustrates the in vivo programming with aplaviroc in the HIV-1 CCCR5 binding FACS.

Rabbits were injected IV with 2 mg/kg dose of aplaviroc-adaptor

7915—naïve rabbit injected with diketone-aplaviroc

8132—diketone immunized rabbit injected with diketone-aplaviroc

8136—lactam immunized rabbit injected with lactam-aplaviroc

8188—naïve rabbit injected with lactam-aplaviroc

The CCR5 binding FACS results are shown in FIG. 20, in which TZM-BL-ccr5 positive cell line, HeLa-ccr5 negative.

BMS Entry Inhibitor-Programmed 38C2

Figure 21:
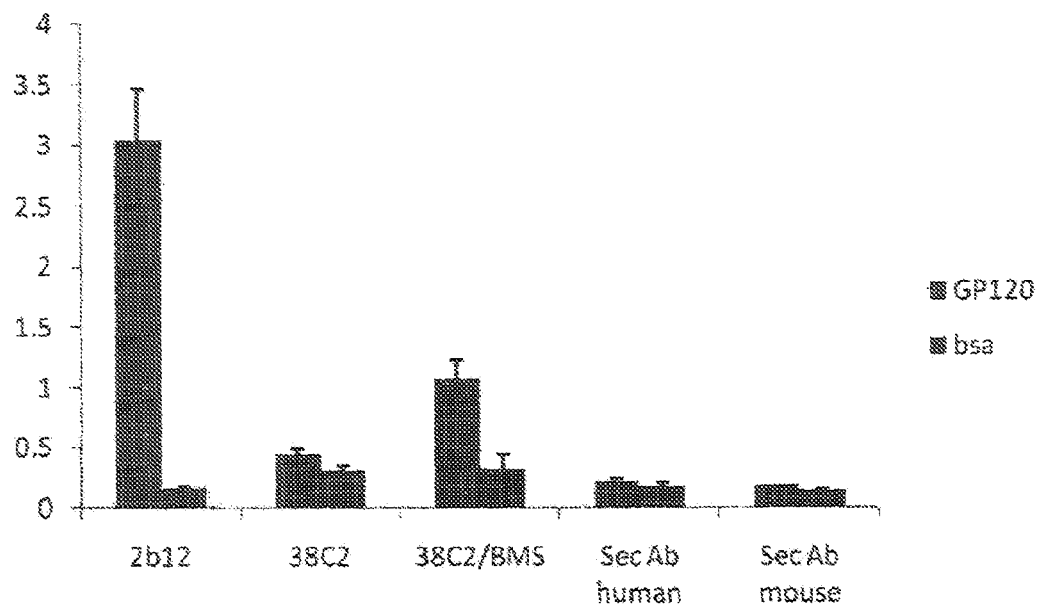
FIG. 21 illustrates the BMS entry inhibitor-programmed 38C2 in the HIV-1 assay.

38C2 was programmed with BMS-lactam (2.2 eq) and purified using desalting column followed by dialysis (48 h). No catalytic activity was observed for programmed 38C3 in methodol assay. The construct was tested in gp120 binding ELISA shown in FIG. 21. Please note some background binding of 38C2 alone.

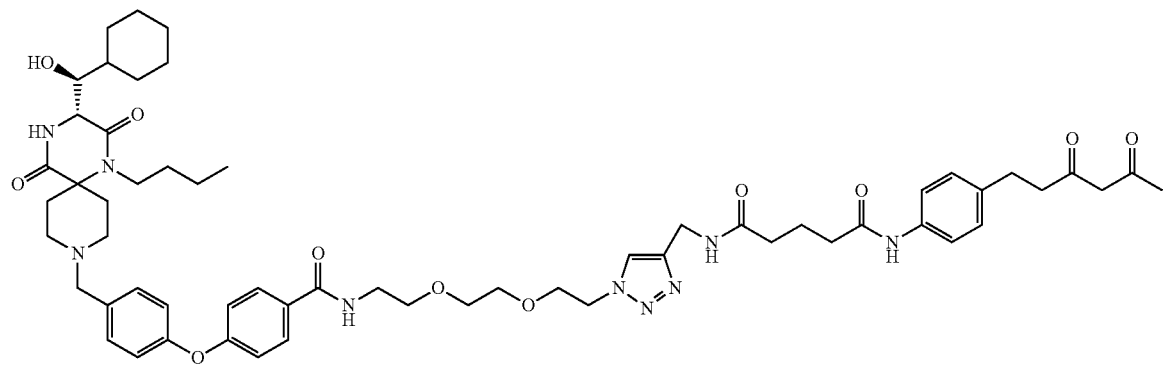 [SMILES: CCCCN1C(=O)[C@@H]([C@@H](O)C2CCCCC2)NC(=O)C12CCN(Cc1ccc(Oc3ccc(C(=O)NCCOCCOCCn4cc(CNC(=O)CCCC(=O)Nc5ccc(CCC(=O)CC(C)=O)cc5)nn4)cc3)cc1)CC2]

Aplaviroc-lactam:

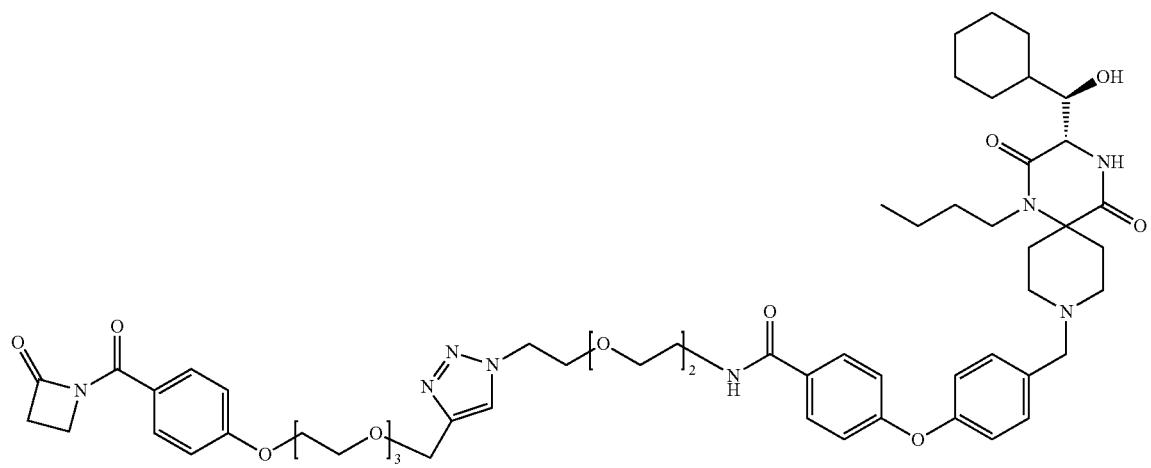

Figure 22:
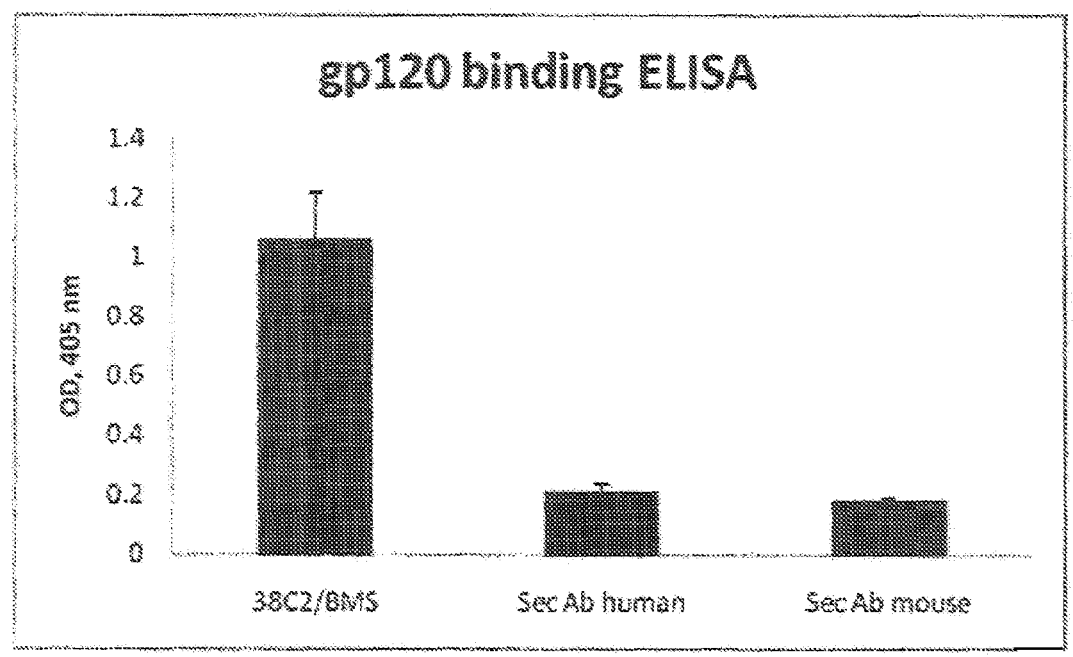
FIG. 22 illustrates the gp120 binding ELISA for aplaviroc-diketone and aplaviroc-lactam.

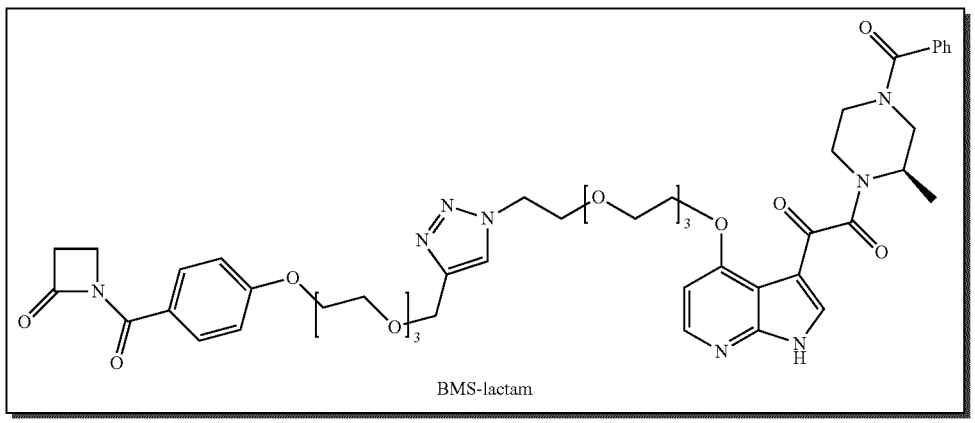
BMS-lactam
FIG. 22 illustrates the gp120 binding ELISA for 38C2/ BMS, Sec Ab human, and Sec Ab mouse.
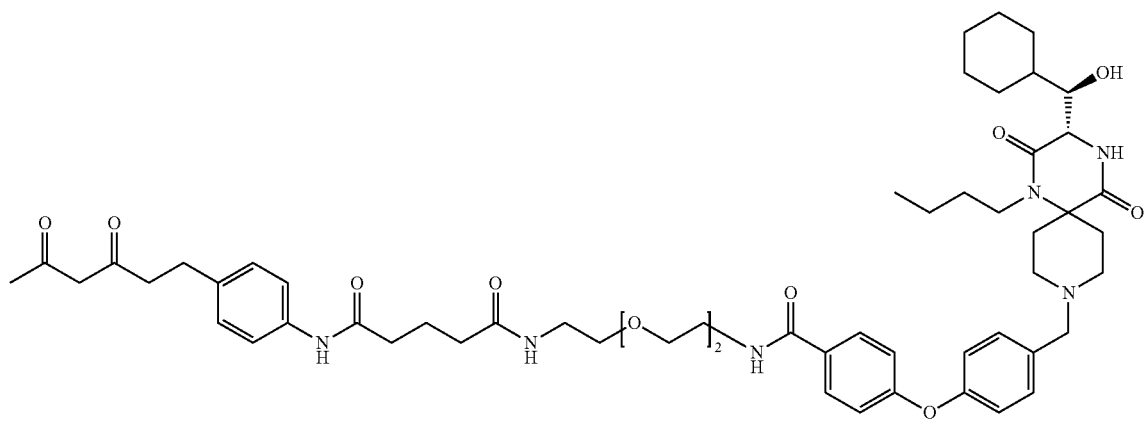
Aplaviroc-diketone:
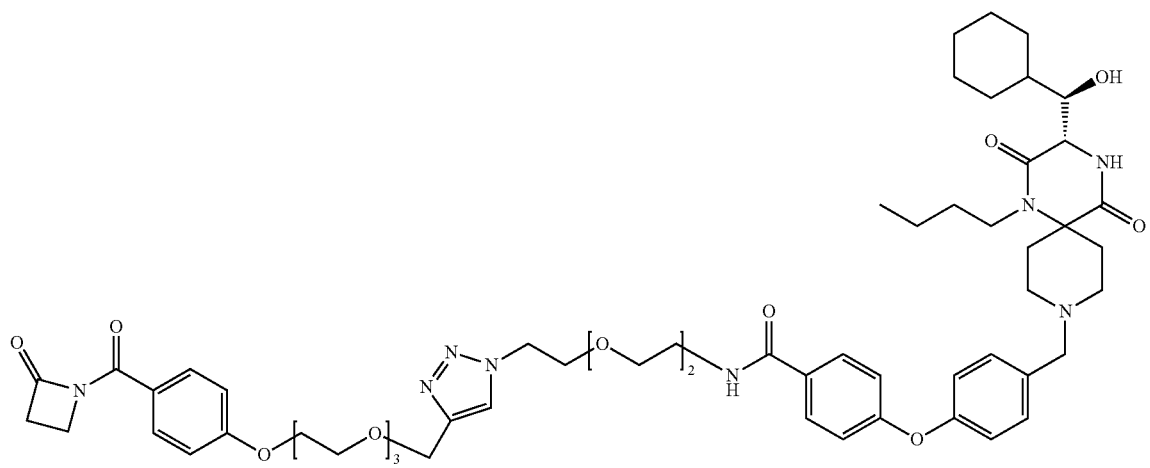

Aplaviroc-lactam:

Although the disclosure has been described with reference to the above example, it should be understood that modifications and variations are encompassed within the spirit and scope of the disclosure. Accordingly, the disclosure is limited only by the following claims.

What is claimed is:

1. The compound of formula V:

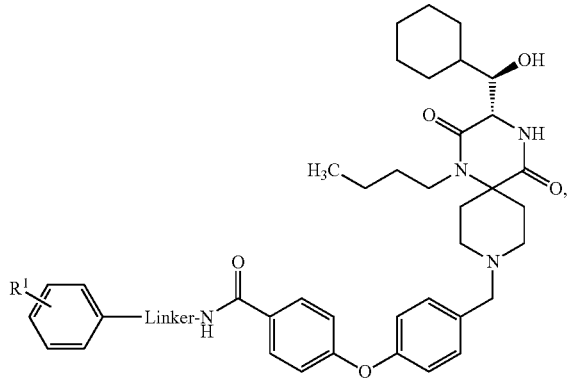

wherein $R^1$ is

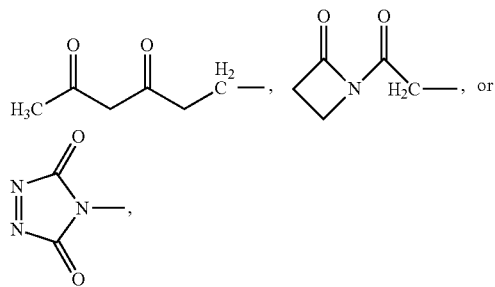

and
wherein the Linker is:
—NHC(═O)(CH$_2$)$_3$C(═O)NH—,
—NHC(═O)(CH$_2$)$_3$C(═O)NH(CH$_2$)$_3$—,
—NHC(═O)(CH$_2$)$_3$C(═O)NH(CH$_2$)$_2$(OCH$_2$CH$_2$)$_2$—,
—(CH$_2$)$_3$NHC(═O)(CH$_2$)$_3$C(═O)NH—,
—O(CH$_2$CH$_2$O)$_3$(CH$_2$)$_2$NHC(═O)(CH$_2$)$_3$C(═O)NH—,

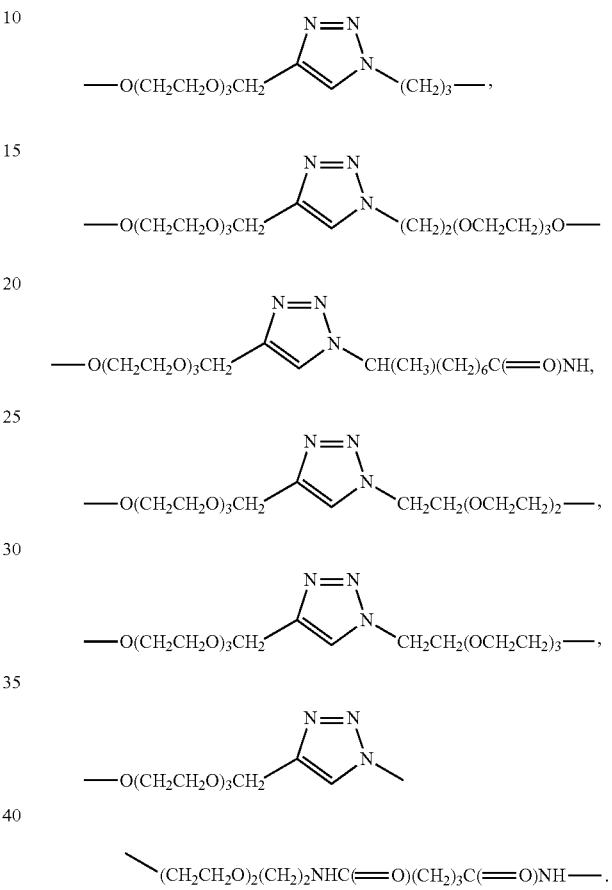

2. The compound of claim 1, wherein the compound of formula V has formula:

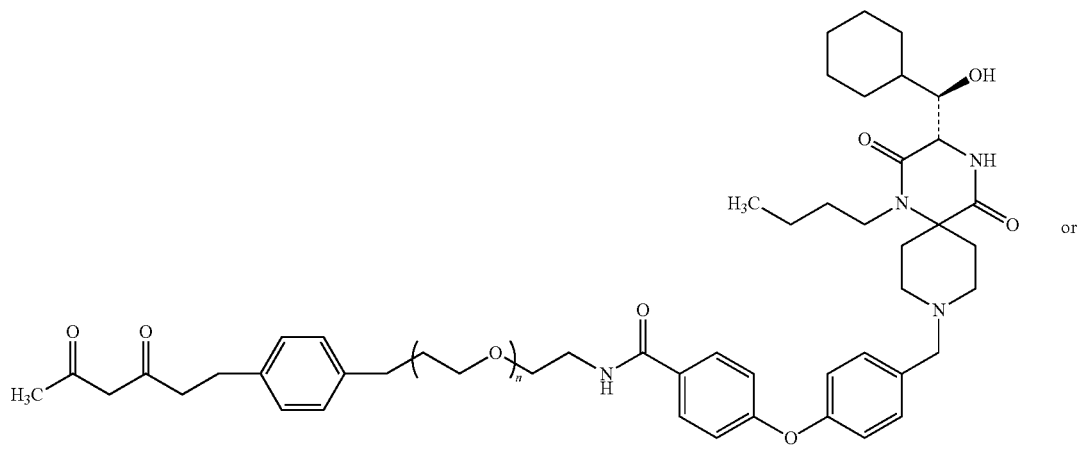

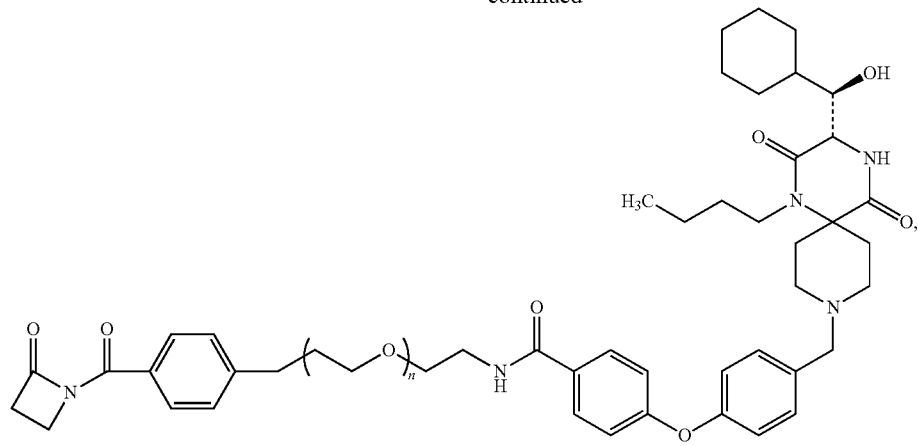
wherein each n is independently an integer from 0 to 20.
* * * * *